United States Patent
Raje et al.

(10) Patent No.: US 9,512,083 B2
(45) Date of Patent: Dec. 6, 2016

(54) HISTONE DEACETYLASE 6 SELECTIVE INHIBITORS FOR THE TREATMENT OF BONE DISEASE

(75) Inventors: Noopur Raje, Newton, MA (US); Loredana Santo, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/233,228

(22) PCT Filed: Jul. 20, 2012

(86) PCT No.: PCT/US2012/047516
§ 371 (c)(1),
(2), (4) Date: Apr. 23, 2014

(87) PCT Pub. No.: WO2013/013113
PCT Pub. Date: Jan. 24, 2013

(65) Prior Publication Data
US 2014/0378385 A1    Dec. 25, 2014

(51) Int. Cl.
| | | |
|---|---|---|
| C07D 239/42 | (2006.01) |
| A61K 45/06 | (2006.01) |
| A61K 31/505 | (2006.01) |
| C07C 259/06 | (2006.01) |
| A61K 38/05 | (2006.01) |

(52) U.S. Cl.
CPC ........... *C07D 239/42* (2013.01); *A61K 31/505* (2013.01); *A61K 38/05* (2013.01); *A61K 45/06* (2013.01); *C07C 259/06* (2013.01)

(58) Field of Classification Search
None
See application file for complete search history.

(56) References Cited

U.S. PATENT DOCUMENTS

| | | |
|---|---|---|
| 2005/0119305 A1 | 6/2005 | Naka et al. |
| 2011/0003878 A1 | 1/2011 | Vidal et al. |
| 2013/0225543 A1* | 8/2013 | Jones ................... A61K 31/165 514/171 |

FOREIGN PATENT DOCUMENTS

| | | |
|---|---|---|
| JP | 2001172245 | 6/2001 |
| JP | 2013518050 | 5/2013 |
| WO | WO 02/074298 | 9/2002 |
| WO | 2010/131922 | 11/2010 |
| WO | 2011/005688 | 1/2011 |
| WO | 2011/091213 | 7/2011 |
| WO | WO 2012/018499 | 2/2012 |

OTHER PUBLICATIONS

Schroeder, Histone Deacetylase Inhibitors Promote Osteoblast Maturation, Journal of Bone and Mineral Research, 2005, 20(12), pp. 2254-2263.*
Shapovalov, Proteasome inhibition with Bortezomib Suppresses Growth and Induces Apoptosis in Osteosarcoma, Int. J. of Cancer, 2010, 127, pp. 67-76.*
Cole, Update on the Treatment of Post-menopausal Osteoporosis, British Medical Bulletin, 2008, 86, pp. 129-143.*

(Continued)

*Primary Examiner* — San-Ming Hui
*Assistant Examiner* — Andrew Lee
(74) *Attorney, Agent, or Firm* — Fish & Richardson P.C.

(57) ABSTRACT

This invention relates to methods for treating bone disease associated with osteoclast activation using HDAC6 selective inhibitors, e.g., small molecule inhibitors such as reverse amide compounds.

6 Claims, 9 Drawing Sheets

(56) References Cited

OTHER PUBLICATIONS

Destaing, A novel Rho-mDia2-HDAC6 pathway controls podosome patterning through microtubule acetylation in osteoclasts, Journal of Cell Science, 2005, 118, pp. 2901-2911.*

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*

Anonymous, "NCT01323751 on Jul. 15, 2011: Study of ACY-1215 Alone and in Combination with Bortezomib and Dexamethasone in Multiple Myeloma," (Jul. 2011) Retrieved from Internet: URL:https://clinicaltrials.gov/archive/NCT01323751/2011_07_15 [retrieved on Feb. 23, 2015].

Kim et al., "Histone deacetylase inhibitor MS-275 stimulates bone formation in part by enhancing Dhx36-mediated TNAP transcription," Journal of Bone and Mineral Research, 26(9):2161-2173 (May 2011).

Pratap et al., "The Histone Deacetylase Inhibitor, Vorinostat, Reduces Tumor Growth at the Metastatic Bone Site and Associated Osteolysis, but Promotes Normal Bone Loss," Molecular Cancer Therapeutics, 9(12):3210-3220 (Dec. 2010).

Santo et al., "Selective Inhibition of HDAC6 with a New Prototype Inhibitor (ACY-1215) Overcomes Bortezomib Resistance in Multiple Myeloma (MM)," Blood, (Nov. 2010), $52^{nd}$ Annual Meeting of the American-Socieity-of-Hematology (ASH); Orlando, FL (Dec. 4-7, 2010), Retrieved from Internet: URL:https://ash.confex.com/ash/2010/webprogram/Paper31925.html [retrieved on Feb. 23, 2015].

Supplementary European Search Report issued in EP12814679 on Feb. 24, 2015 (12 pages).

Westendorf, J., "Histone deacetylases in control of skeletogenesis," Journal of Cellular Biochemistry, 102(2):332-340 (Jan. 2007).

International Search Report and Written Opinion mailed Dec. 13, 2012 in international application No. PCT/US2012/047516, 17 pgs.

Iaconelli et al., "HDAC6 Inhibitors Modulate Lys49 Acetylation and Membrane Localization of β-Catenin in Human iPSC-Derived Neuronal Cells," ACS Chemical Biology, 2015, 10(3):883-890.

Dai et al., "Indole amide hydroxamic acids as potent inhibitors of histone deacetylases," Bioorganic & Medicinal Chemistry Letters, 2003, 13(11):1897-1901.

Japanese Office Action in Japanese Application No. JP 2014-521813, dated Mar. 4, 2016, 7 pages (with English translation).

* cited by examiner

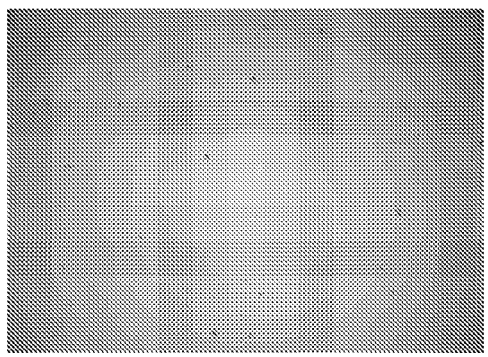
FIG. 4A — CTR alpha mem
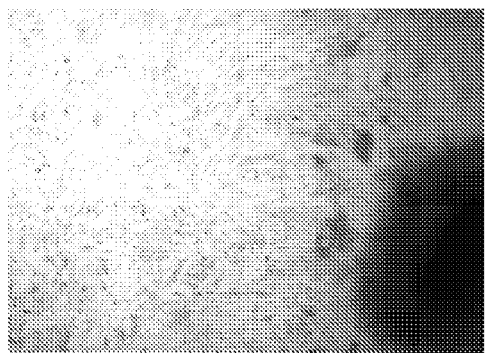
FIG. 4B — CTR OBL medium
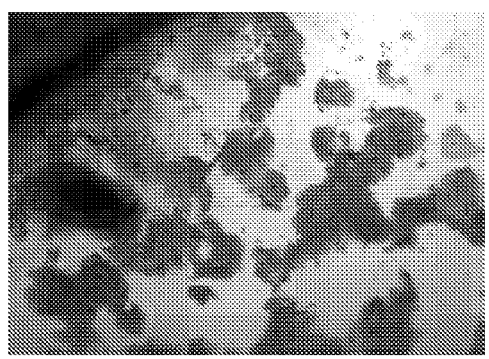
FIG. 4C — Compound A 1 µM
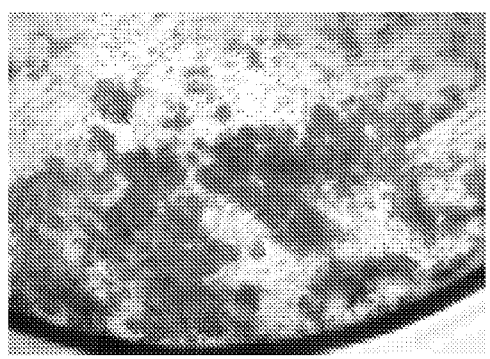
FIG. 4D — VEL 2.5 nM
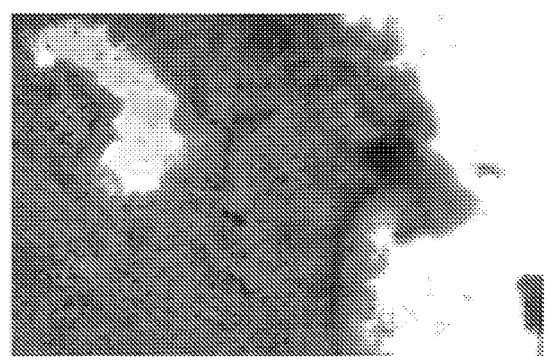
FIG. 4E — COMBO

HISTONE DEACETYLASE 6 SELECTIVE INHIBITORS FOR THE TREATMENT OF BONE DISEASE

CROSS-REFERENCE TO RELATED APPLICATION

This application is a U.S. National Phase Application under 35 U.S.C. §371 of International Patent Application No. PCT/US2012/047516, filed on Jul. 20, 2012, which claims the benefit of U.S. Provisional Patent Application Ser. No. 61/509,857, filed on Jul. 20, 2011, the entire contents of which are hereby incorporated by reference.

TECHNICAL FIELD

This invention relates to methods for treating bone disease associated with osteoclast activation using Histone Deacetylase 6 (HDAC6) selective inhibitors, e.g., reverse amide compounds, and the compounds themselves.

BACKGROUND

Normal bone physiology is a dynamic process involving a balance between bone formation (by osteoblasts) and resorption (by osteoclasts).

SUMMARY

The methods described herein are based, at least in part, on the discovery that HDAC6-selective inhibitors are bone anabolic agents, i.e., they inhibit osteoclastogenesis and activate osteoblastogenesis. Thus, these agents can be used to treat conditions associated with high levels of bone catabolism, e.g., due to increased levels or activity of osteoclasts or reduced levels or activity of osteoblasts.

Thus, in one aspect, the present invention provides methods for treating, or reducing risk of, bone disorders associated with abnormally high bone catabolism in a subject. The methods include administering to the subject a therapeutically effective amount of an HDAC6-selective inhibitor.

In another aspect, the present invention provides HDAC6-selective inhibitors, e.g., reverse amide compounds of formula I, or pharmaceutically acceptable salts, esters, or prodrugs thereof, for use in treating or reducing the risk of, a bone disorders associated with abnormally high bone catabolism in a subject.

In still another aspect, the present invention provides methods of treating, or reducing risk of, osteoporosis, osteopenia, Paget's disease, bone metastasis in breast, lung, and prostate cancers, primary tumor cell involvement in Multiple Myeloma (MM), or osteogenesis imperfecta in a subject, the methods including administering to the subject a therapeutically effective amount of 2-(diphenylamino)-N-(7-(hydroxyamino)-7-oxoheptyl)pyrimidine-5-carboxamide (Compound A):

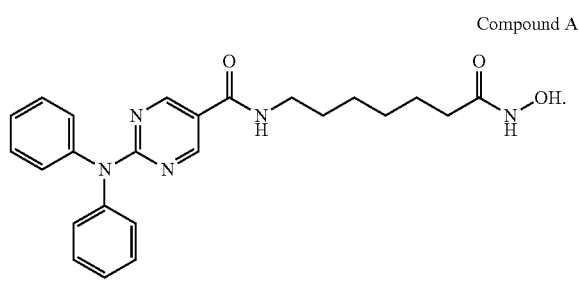 [SMILES: O=C(CCCCCCNC(=O)c1cnc(N(c2ccccc2)c2ccccc2)nc1)NO]

Compound A

In some embodiments, the HDAC6-selective inhibitors are selected from the group consisting of CAY10603; chiral 3,4-dihydroquinoxalin-2(1H)-one and piperazine-2,5-dione aryl hydroxamates; cyclic hexapeptide hydroxamic acid and analogs thereof; ISOX (tert-butyl 4-(3-(7-(hydroxyamino)-7-oxoheptyl-carbamoyl)isoxazol-5-yl)phenylcarbamate; trichostatin; tubacin; niltubacin; MAZ-1391, MAZ-1338, and MAZ-TBDPS-O-1380; tubastatin A (n-Hydroxy-4-((2-methyl-3,4-dihydro-1H-pyrido[4,3-b]-indol-5(2H)-yl) methyl)benzamide); and B4061 ((S)-[5-Acetylamino-1-(2-oxo-4-trifluoromethyl-2H-chromen-7-ylcarbamoyl)pentyl] carbamic acid tert-butyl ester, Cpd 3b).

In some embodiments, the HDAC6-selective inhibitors are reverse amide compounds, e.g., reverse amide compounds of formula I:

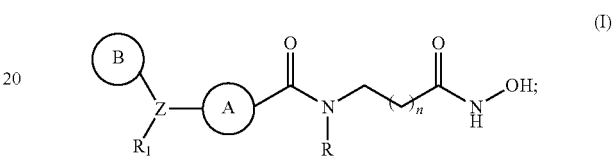

or pharmaceutically acceptable salts, esters, or prodrugs thereof,
wherein,
Z is N or CR*, wherein R* is an optionally substituted alkyl, an optionally substituted acyl, an optionally substituted aryl or an optionally substituted heteroaryl;
ring A is an optionally substituted aryl or an optionally substituted heteroaryl;
ring B is an optionally substituted aryl or an optionally substituted heteroaryl;
$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N($R_3$)($R_3$), —CH$_2$CH$_2$OH, OCH$_2$CH$_2$OH, SH, or thio alkoxy;
or ring B and $R_1$ may together with the atom to which each is attached, form an optionally substituted heterocyclic, or an optionally substituted heteroaryl;
or R* and $R_1$ together with the atom to which each is attached, may form an optionally substituted carbocyclic, optionally substituted heterocyclic, optionally substituted aryl or optionally substituted heteroaryl ring;
R is H or an optionally substituted alkyl; or R and ring A may be joined to form a fused bicyclic ring which may be optionally substituted;
each $R_2$ is independently alkyl, cycloalkyl, heterocycloalkyl, aryl, or heteroaryl, each of which is optionally substituted;
each $R_3$ is independently alkyl, cycloalkyl, heterocycloalkyl, aryl, or heteroaryl, each of which is optionally substituted;
n is 4, 5, 6, 7 or 8; and
p is 0, 1, or 2.

In some embodiments, the HDAC6-selective inhibitors are reverse amide compounds of formula IV:

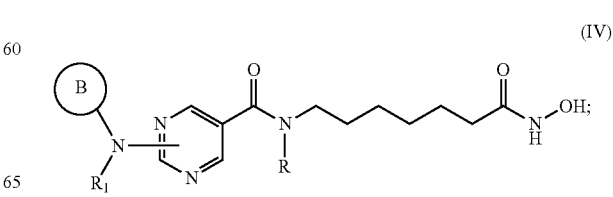

or pharmaceutically acceptable salts, esters, or prodrugs thereof, wherein, ring B is an optionally substituted aryl or an optionally substituted heteroaryl;

$R_1$ is H, alkyl, haloalkyl, alkenyl, aryl, arylalkyl, heteroaryl, heterocyclic, or carbocyclic, each of which may be optionally substituted;

or ring B and $R_1$ may together with the atom to which each is attached, form an optionally substituted heterocyclic, or an optionally substituted heteroaryl, and R is H or an optionally substituted alkyl; or R and the 1,3-pyrimidinyl ring may be joined to form a fused bicyclic ring which may be optionally substituted.

In some embodiments, ring B is phenyl, pyridinyl, pyrimidinyl, or pyrazinyl; each of which may be optionally substituted.

In some embodiments, ring B is substituted by alkyl, aryl, aralkyl, haloalkyl, halo, OH, $NH_2$, CN, or $NO_2$.

In some embodiments, $R_1$ is H, alkyl, aryl, arylalkyl, or heteroaryl, each of which may be optionally substituted. In some embodiments, $R_1$ is substituted by OH or halo, e.g., by OH.

In some embodiments, the ring formed by ring B and $R_1$ is piperidine, pyrrolidine, tetrahydroquinoline, morpholine, piperazine, tetrahydro-triazolo pyrazine, diazepane, each of which is optionally substituted.

In some embodiments, the HDAC6-selective inhibitors are reverse amide compounds of formula IVa:

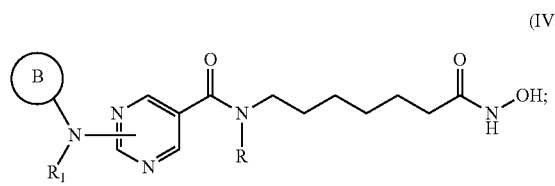

(IVa)

or pharmaceutically acceptable salts, esters, or prodrugs thereof, wherein,

B is phenyl, pyridinyl, pyrimidinyl, or pyrazinyl; each of which may be optionally substituted by $C_{1-8}$-alkyl, $C_{1-8}$-alkoxy, $C_{6-10}$-aryl, halo-$C_{1-8}$-alkyl, halo, OH, $NH_2$, CN, or $NO_2$;

$R_1$ is phenyl, pyridinyl, pyrimidinyl, or pyrazinyl; each of which may be optionally substituted by $C_{1-8}$-alkyl, $C_{1-8}$-alkoxy, $C_{6-10}$-aryl, halo-$C_{1-8}$-alkyl, halo, OH, $NH_2$, CN, or $NO_2$;

and

R is H or $C_{1-8}$-alkyl.

In an embodiment of formula IVa, $R_1$ is substituted by OH or halo. In still another embodiment, B is phenyl, pyridinyl, or pyrimidinyl, each of which may be optionally substituted by $C_{1-8}$-alkyl, halo, or $C_{1-8}$-alkoxy. In yet another embodiment, $R_1$ is phenyl, pyridinyl, or pyrimidinyl, each of which may be optionally substituted by $C_{1-8}$-alkyl, halo, or $C_{1-8}$-alkoxy.

In some embodiments, the HDAC6-selective inhibitor is 2-(diphenylamino)-N-(7-(hydroxyamino)-7-oxoheptyl)pyrimidine-5-carboxamide (Compound A):

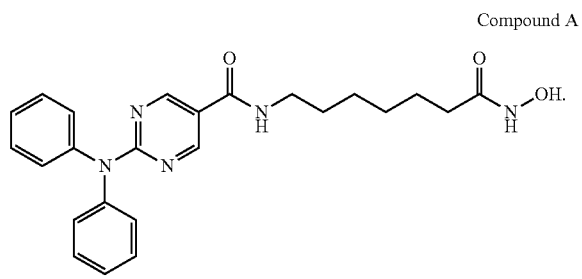 [SMILES: O=C(CCCCCCNC(=O)c1cnc(N(c2ccccc2)c2ccccc2)nc1)NO]

Compound A

In some embodiments, the abnormally high bone catabolism is associated with increased osteoclastogenesis in the subject, decreased osteoblastogenesis in the subject, increased osteoclast activity in the subject, decreased osteoblast activity in the subject, an imbalance of osteoclastogenesis and osteoblastogenesis in the subject, or an imbalance of osteoclast and osteoblast activity in the subject.

In some embodiments, the bone disorder is selected from the group consisting of osteoporosis; osteopenia, Paget's disease; bone metastasis in breast, lung, and prostate cancers; primary tumor cell involvement in Multiple Myeloma (MM); and osteogenesis imperfecta.

In some embodiments, the methods further include administering an additional active agent selected from the group consisting of bisphosphates, RANK ligands, VELCADE® (bortezomib), Carfilzomib, REVLIMID® (lenalidomide), and Pomalidomide.

In some embodiments, the bone disorder is associated with primary tumor involvement in MM, and the method further comprises administering VELCADE (bortezomib), Carfilzomib, REVLIMID® (lenalidomide), and Pomalidomide.

In some embodiments, the bone disorder is associated with primary tumor involvement in MM, and the method further comprises administering a therapeutically effective amount of VELCADE (bortezomib).

In some embodiments, the bone disorder is osteoporosis, and the methods further include administering a bisphosphate, e.g., actonel.

The disclosure of U.S. patent application Ser. No. 13/010, 974, titled "Reverse Amide Compounds as Protein Deacetylase Inhibitors and Methods of Use Thereof, published as U.S. Patent Application 2011/0300134, is incorporated herein by reference in its entirety.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 4A-E are a set of five images showing that Compound A alone and in combination with bortezomib increases calcium deposits, stained with Alizarin red (dark gray; red in original).

DETAILED DESCRIPTION

Figure 1A:
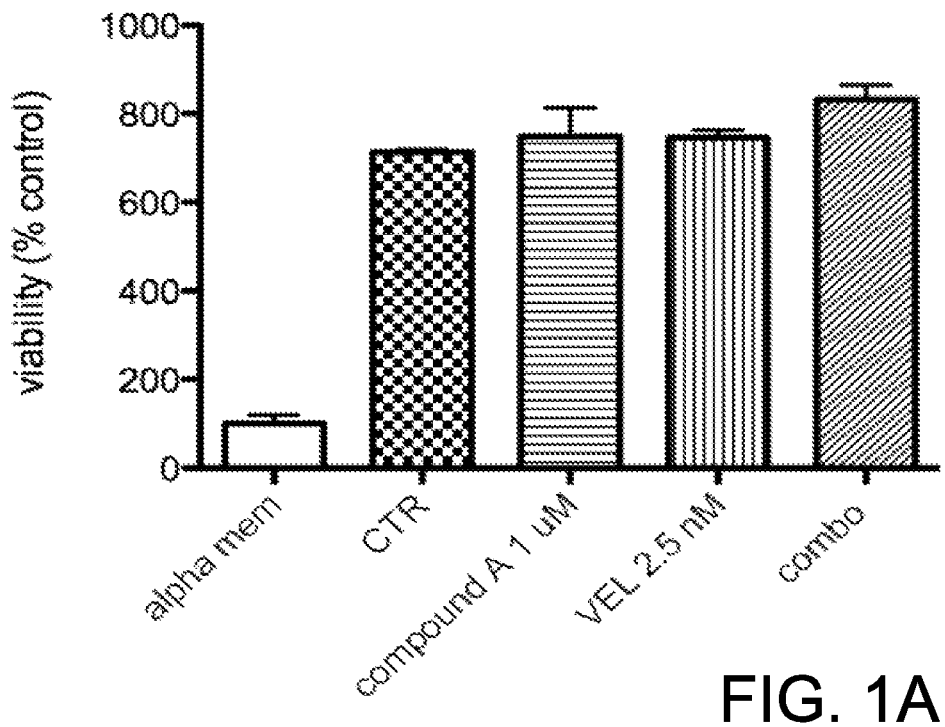
FIGS. 1A-D are bar graphs showing that Compound A alone and in combination with bortezomib (VEL) does not affect the viability of osteoblasts (OBLs) (1A and 1C, AlamarBlue) and increases OBLs function (1B and 1D, alkaline phosphatase (ALP) activity).
Figure 1B:
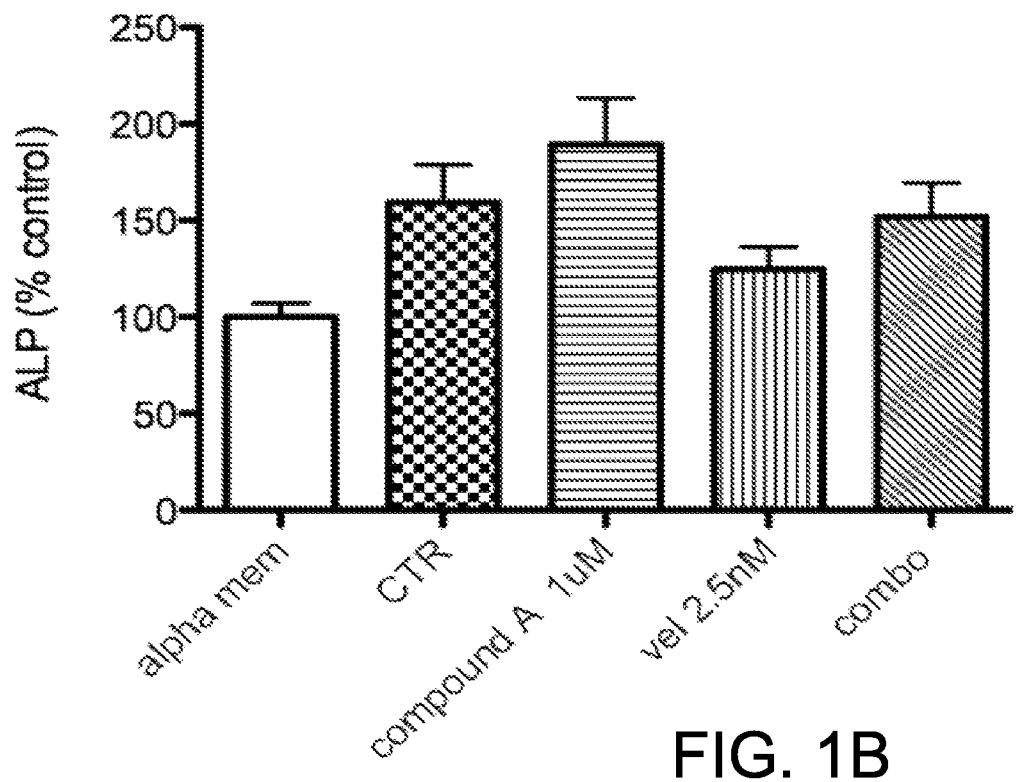

Under normal physiologic conditions, the dynamic activity of osteoclasts (OCLs) and osteoblasts (OBLs) results in balanced bone resorption and formation maintaining bone homeostasis. In catabolic disease states, the balance is tilted towards excessive bone resorption, e.g., because of increased osteoclastic activity or reduced osteoblastic activity or both, resulting in osteolytic bone disease. In some conditions, osteoblasts are markedly suppressed and very little if any osteoblastic activity is noted. As described herein, HDAC6-selective inhibitors are bone anabolic agents and thus shift the balance back towards normal.

Methods of Treatment

Disclosed herein are methods for treating disorders associated with excessive bone catabolism (resorption), whether as a result of excessive OCL activity, reduced OBL activity, or both. The methods can include selection of a subject, e.g., selecting a subject for treatment according to a method described herein, e.g., by identifying a subject who has, or is at risk of developing, a disorder associated with excessive bone resorption as described herein.

As used in this context, to "treat" means to ameliorate at least one symptom of the disorder associated with excessive bone resorption. Often, these disorders result in a loss of bone density; thus, a treatment can inhibit further loss in bone density, can result in an increase in bone density, and can cause a return or approach to normal bone density.

An "effective amount" is an amount sufficient to effect beneficial or desired results. For example, a therapeutic amount is one that treats the disorder or achieves a desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including, but not limited to, the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The term "subject" as used herein refers to a mammal. A subject therefore refers to, for example, dogs, cats, horses, cows, pigs, guinea pigs, and the like. The subject can be a human. When the subject is a human, the subject may be referred to herein as a patient.

Dosage, toxicity, and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are typically preferred. While compounds that exhibit toxic side effects may be used, care should be taken to design a delivery system that targets such compounds to the site of affected tissue to minimize potential damage to uninfected cells and, thereby, reduce side effects.

The data obtained from cell culture assays and animal studies can be used in formulating a range of dosages for use in humans. The dosage of such compounds lies preferably within a range of circulating concentrations that include the ED50 with little or no toxicity. The dosage may vary within this range depending upon the dosage form employed and the route of administration utilized. For any compound used in the methods of the inventions described herein, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

In some embodiments, the disorder is selected from the group consisting of osteoporosis; osteopenia, Paget's disease; bone metastasis in breast, lung, and prostate cancers; primary tumor cell involvement in Multiple Myeloma (MM); and osteogenesis imperfecta. Generally, the methods include administering a therapeutically effective amount of an HDAC6-selective inhibitor as described herein, e.g., a compound of formula I, e.g., Compound A, to a subject who is in need of, or who has been determined to be in need of, such treatment.

Osteoporosis

In some embodiments, the disorder associated with excessive bone catabolism is osteoporosis, which is the thinning of bone tissue and loss of bone density over time. A subject is determined to have or be at risk of developing osteoporosis based on methods known in the art. For example, risk can be determined based on the presence of one or more risk factors, e.g., gender (increased risk for females); age (increased risk over age 50 for women or age 70 for men); ethnicity (increased risk for Caucasians and Asians); bone structure and body weight (increased risk for those with small bones and thin frames); family history; prior history of broken bones; menopause/hysterectomy; and medications (e.g., glucocorticoid therapy and androgen deprivation therapy increase risk). Additional factors that increase risk include alcohol intake; smoking; low body mass index; poor nutrition; vitamin D deficiency; eating disorders (e.g., anorexia nervosa, bulimia); insufficient exercise; low dietary calcium intake; and frequent falls. Osteoporosis can also be associated with (e.g., increased risk of developing osteoporosis is associated with) conditions including lupus, rheumatoid arthritis; primary/secondary hypogonadism or low testosterone levels in men; celiac disease; inflammatory bowel disease (IBD) (including different forms of IBD, such as Crohn's disease and ulcerative colitis); weight loss surgeries (such as gastric bypass surgery); diabetes; hyperparathyroidism; hyperthyroidism; amenorrhea; leukemia/lymphoma; sickle cell disease; chronic diseases that reduce mobility (such as stroke, Parkinson's disease, and multiple sclerosis (MS); AIDS/HIV; ankylosing spondylitis; blood and bone marrow disorders; breast cancer and hormone therapies for breast cancer; chronic obstructive pulmonary disease (COPD), including emphysema; Cushing's syndrome; depression; female athlete triad (includes loss of menstrual periods, an eating disorder and excessive exercise); gastrectomy; gastrointestinal bypass procedures; kidney disease that is chronic and long lasting; liver disease that is severe, including biliary cirrhosis; malabsorption syndromes, including celiac disease; multiple myeloma; organ transplants; polio and post-polio syndrome; poor diet, including malnutrition; premature menopause; prostate cancer and hormone therapies for prostate cancer; rheumatoid arthritis; scoliosis; spinal cord injuries; stroke; thalassemia; thyrotoxicosis; and weight loss.

In some embodiments, the methods include diagnosis risk or presence of osteoporosis based on bone mineral density (BMD). A number of methods for determining BMD are known in the art, including DXA (dual-energy X-ray absorptiometry); pDXA (peripheral DXA); SXA (single-energy X-ray absorptiometry); DPA (dual photon absorptiometry); SPA (single photon absorptiometry); QCT (Quantitative Computed Tomography); and QUS (Quantitative Ultrasound). Most use densitometry to measure BMD.

As noted in Table 1 below, osteoporosis is diagnosed when a person's BMD is equal to or more than 2.5 standard deviations below this reference measurement. Osteopenia is diagnosed when the measurement is between 1 and 2.5 standard deviations below the young adult reference measurement.

TABLE 1

| Status | Hip BMD |
| --- | --- |
| Normal | T-score of −1 or above |
| Osteopenia | T-score lower than −1 and greater than −2.5 |
| Osteoporosis | T-score of −2.5 or lower |
| Severe osteoporosis | T-score of −2.5 or lower, and presence of at least one fragility fracture |

In some embodiments, the methods include determining a subject's BMD, and if the subject's BMD indicates that the subject has osteopenia, osteoporosis, or severe osteoporosis, then administering an HDAC6 inhibitor as described herein, e.g., a compound of formula I, e.g., Compound A, to the subject.

The methods can further include monitoring the subject (e.g., by evaluating frequency of fractures, presence of bone lesions, bone density or bone morphology, e.g., using x-ray or other imaging methods) at selected intervals, e.g., a month, three months, six months, or a year after initiation of the treatment, and selected intervals thereafter, e.g., every month, every three months, every six months, or every year thereafter. An increase in bone density, normal bone morphology, or decrease in frequency of fractures or bone lesions, indicates that the treatment is effective.

For example, the methods can further include monitoring the subject by repeating the BMD test at selected intervals, e.g., a month, three months, six months, or a year after initiation of the treatment, and selected intervals thereafter, e.g., every month, every three months, every six months, or every year thereafter. An increase in the T score indicates that the subject's bone density is increasing, e.g., that the treatment is effective.

Paget's Disease

Also known as osteitis deformans, Paget's Disease is a chronic condition that causes abnormal bone growth. Osteoclasts are more active than osteoblasts, deranging the bone remodeling process, resulting in bone that is brittle, enlarged and susceptible to fracture, deformation, arthritis, and nerve compression. Paget's disease can appear in any bone, but typically affects the spine, pelvis, long bones of the limbs, and skull. Risk factors include family history. Diagnosis is made based on the presence of characteristic findings on x-ray, with confirmation by the presence of elevated levels of serum alkaline phosphatase, bone biopsy, and/or bone imaging studies.

The methods can further include monitoring the subject (e.g., by evaluating frequency of fractures, presence of bone lesions, bone density or bone morphology, e.g., using x-ray or other imaging methods) at selected intervals, e.g., a month, three months, six months, or a year after initiation of the treatment, and selected intervals thereafter, e.g., every month, every three months, every six months, or every year thereafter. An increase in bone density, normal bone morphology, or decrease in frequency of fractures or bone lesions, indicates that the treatment is effective.

Metastatic Bone Disease

Metastatic bone disease (MBD) in advanced-stage cancer is largely driven by homotypic and heterotypic cellular interactions between invading tumor cells, osteoblasts and osteoclasts. Osteoclast-mediated bone degradation and subsequent bone loss and/or osteosclerotic lesions result.

The methods described herein can include identifying a subject who has bone lesions associated with MBD, and administering an HDAC6 inhibitor as described herein, e.g., a reverse amide, e.g., a compound of formula I, e.g., Compound A. The presence of bone lesions in a subject with MBD can be detected using methods known in the art, e.g., x-ray.

The methods can further include monitoring the subject (e.g., by evaluating frequency of fractures, presence of bone lesions, bone density or bone morphology, e.g., using x-ray or other imaging methods) at selected intervals, e.g., a month, three months, six months, or a year after initiation of the treatment, and selected intervals thereafter, e.g., every month, every three months, every six months, or every year thereafter. An increase in bone density, normal bone morphology, or decrease in frequency of fractures or bone lesions, indicates that the treatment is effective.

Bone Disease in Multiple Myeloma

Multiple myeloma (MM) is a plasma cell malignancy characterized by a high capacity to induce osteolytic bone lesions. MM remains an incurable disease despite recent advances with novel therapies, such as immunomodulatory drugs and proteosome inhibitors. These agents have shown marked antitumor activity, however the number of patients with relapsed disease remains high (Kyle and Rajkumar, Blood. 111:2962-72 (2008)). 70-80% of patients develop osteolytic bone lesions associated with increased morbidity and mortality resulting in consequent pathologic fractures, vertebral collapse and disability (Schroeder and Westendorf, J Bone Mine Res. 20:2254-63 (2005)).

The methods described herein can include identifying a subject who has osteolytic bone lesions associated with MM, and administering an HDAC6 inhibitor as described herein, e.g., a reverse amide, e.g., a compound of formula I, e.g., Compound A. The presence of osteolytic bone lesions in a subject with MM can be detected using methods known in the art, e.g., x-ray or other imaging methods. Symptoms of bone lesions include bone pain in the back or chest, or less commonly, the arms and legs.

The methods can further include monitoring the subject (e.g., by evaluating frequency of fractures, presence of bone lesions, bone density or bone morphology, e.g., using x-ray or other imaging methods) at selected intervals, e.g., a month, three months, six months, or a year after initiation of the treatment, and selected intervals thereafter, e.g., every month, every three months, every six months, or every year thereafter. An increase in bone density, normal bone morphology, or decrease in frequency of fractures or bone lesions, indicates that the treatment is effective.

Osteogenesis Imperfecta

Osteogenesis Imperfecta (OI) is a rare heritable condition characterized by bone fragility and reduced bone mass. OI is classified types OI-I to VII, and most cases are associated with mutations in one of the two genes encoding type I collagen. In other cases of OI, mutations are present in CRTAP, a cartilage-related protein, or 3-prolyl-hydroxylase (P3H1). The disease is characterized by increased bone turnover rate due to repair activity triggered to replace weak tissue. Disuse bone loss further often compounds the decrease in bone mass. Diagnosis of OI can be made using methods known in the art, e.g., the presence of blue sclera, multiple bone fractures, and early hearing loss, and confirmed by genetic testing or a skin punch biopsy. The presence of areas of low bone density in a subject with OI can be detected using methods known in the art, e.g., x-ray or other imaging methods. The present methods can be used to reduce osteoclast-mediated bone resorption, and so tilt the remodeling balance towards an increase in bone mass. Thus the methods can include identifying a subject with OI, and administering a therapeutically effective amount of an HDAC6-selective inhibitor, e.g., a compound of formula I, e.g., Compound A.

The methods can further include monitoring the subject (e.g., by evaluating frequency of fractures, bone density or bone morphology, e.g., using x-ray or other imaging methods) at selected intervals, e.g., a month, three months, six months, or a year after initiation of the treatment, and selected intervals thereafter, e.g., every month, every three months, every six months, or every year thereafter. An increase in bone density, normal bone morphology, or decrease in frequency of fractures indicates that the treatment is effective.

HDAC6 Inhibitors

The methods described herein include the administration of effective amounts of HDAC6-selective inhibitors. As used herein, HDAC6-selective inhibitors include compounds, e.g., small molecules, e.g., compounds of Formula I, which inhibit HDAC6 at lower concentrations than other HDACs, e.g., HDAC1. In particular, HDAC6-selective inhibitors demonstrate an inhibition of HDAC6 that is at least five times greater than inhibition of Class I HDACs (HDAC1, 2, or 3), or any of HDAC4, 5, 7, 8, 9, 10, or 11. "HDAC6-selective inhibitors" do not include pan-HDAC inhibitors or non-HDAC6-selective inhibitors such as JNJ-26481585, trichostatin A, NVP-LAQ824, panobinostat, ITF2357, sodium butyrate, vorinostat (Zolinza, suberoylanilide hydroxamic acid, SAHA)), LBH589 (panobinostat), valproic acid (VPA), MS-275 (entinostat), resminostat, AR-42, SB939, CHR-2845, CHR-3996, romidepsin (Istodax, Depsipeptide), givinostat, and belinostat; see, e.g., Table 2 of McGee-Lawrence and Westendorf, Gene 474:1-11 (2011), incorporated by reference herein.

A number of HDAC6-selective inhibitors are known in the art, including reverse amides as described herein; CAY10603 (Kozikowski et al., J. Med. Chem. 51:4370-4373 (2008)); chiral 3,4-dihydroquinoxalin-2(1H)-one and piperazine-2,5-dione aryl hydroxamates (Smil et al., Bioorganic & Medicinal Chemistry Letters, 19(3): 688-692 (2009); cyclic hexapeptide hydroxamic acid and analogs thereof (Jose et al., Bioorganic & Medicinal Chemistry, 12 (6):1351-1356 (2004); ISOX (tert-butyl 4-(3-(7-(hydroxyamino)-7-oxoheptyl-carbamoyl)isoxazol-5-yl)phenylcarbamate, Butler et al., J. Am. Chem. Soc. 132: 10842-10846 (2010)); trichostatin; tubacin; niltubacin; MAZ-1391, MAZ-1338, and MAZ-TBDPS-O-1380 (Cabrero et al., 17(8):3435-3445 (2006); tubastatin A (n-Hydroxy-4-((2-methyl-3,4-dihydro-1H-pyrido[4,3-b]-indol-5(2H)-yl)methyl)benzamide); B4061 ((S)-[5-Acetylamino-1-(2-oxo-4-trifluoromethyl-2H-chromen-7-ylcarbamoyl)pentyl]carbamic acid tert-butyl ester, Cpd 3b). In preferred embodiments, the HDAC6-selective inhibitors are reverse amides.

Reverse Amides

In some embodiments, the methods include the administration of a reverse amide compound of formula I:

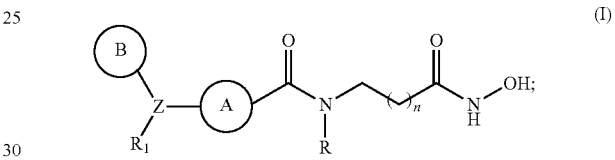

or a pharmaceutically acceptable salt, ester or prodrug thereof, wherein,

Z is N or CR*, wherein R* is an optionally substituted alkyl, an optionally substituted acyl, an optionally substituted aryl or an optionally substituted heteroaryl;

ring A is an optionally substituted aryl or an optionally substituted heteroaryl;

ring B is an optionally substituted aryl or an optionally substituted heteroaryl;

$R_1$ is (i) H, alkyl, haloalkyl, alkenyl, aryl, arylalkyl, heteroaryl, heterocyclic, carbocyclic, C(O)—$R_2$, C(O)O—$R_2$, or S(O)$_p$, each of which may be optionally substituted; or (ii) when Z is CR*, $R_1$ may be optionally substituted branched alkyl, OR$_3$, or N(R$_3$)(R$_3$), —CH$_2$CH$_2$OH, OCH$_2$CH$_2$OH, SH, or thio alkoxy;

or ring B and $R_1$ may together with the atom to which each is attached, form an optionally substituted heterocyclic, or an optionally substituted heteroaryl;

or R* and $R_1$ together with the atom to which each is attached, may form an optionally substituted carbocyclic, optionally substituted heterocyclic, optionally substituted aryl or optionally substituted heteroaryl ring;

R is H or an optionally substituted alkyl; or R and ring A may be joined to form a fused bicyclic ring which may be optionally substituted;

each $R_2$ is independently alkyl, cycloalkyl, heterocycloalkyl, aryl, or heteroaryl, each of which is optionally substituted;

each $R_3$ is independently alkyl, cycloalkyl, heterocycloalkyl, aryl, or heteroaryl, each of which is optionally substituted;

n is 4, 5, 6, 7 or 8; and p is 0, 1, or 2.

In one embodiment, the ring A is phenyl, naphthyl, anthracenyl, pyridinyl, pyrimidinyl, pyrazinyl, indolyl, imidazolyl, oxazolyl, furyl, thienyl, thiazolyl, triazolyl, isoxazolyl, quinolinyl, pyrrolyl, pyrazolyl, or 5,6,7,8-tetrahydroisoquinoline; each of which may be optionally substituted.

In another embodiment, the ring B is phenyl, naphthyl, anthracenyl, pyridinyl, pyrimidinyl, pyrazinyl, indolyl, imidazolyl, oxazolyl, furyl, thienyl, thiazolyl, triazolyl, isoxazolyl, quinolinyl, pyrrolyl, pyrazolyl, or 5,6,7,8-tetrahydroisoquinoline; each of which may be optionally substituted.

In certain embodiments, $R_1$ is H, optionally substituted alkyl, optionally substituted aryl, or optionally substituted heteroaryl, or $R_1$ is OH or alkoxy.

In a further embodiment, $R_1$ is H, methyl, ethyl, propyl, i-propyl, butyl, i-butyl, t-butyl, pentyl, hexyl, phenyl, naphthyl, pyridinyl, OH, $OCH_3$, $OCH_2CH_3$, O—Pr, O-iPr, O-Bu, O-sBu, or O-tBu; each of which may be optionally substituted.

In various embodiments, $R_1$ is OH, alkoxy, $NH_2$, NH(alkyl), N(alkyl)(alkyl), NH-aryl, NH-heteroaryl, N(aryl)(aryl), N(aryl)(heteroaryl), or N(heteroaryl)(heteroaryl).

In other embodiments, the carbonyl and the Z group attached to ring A are disposed para to each other.

In other embodiments, the carbonyl and Z group attached to ring A are disposed meta to each other.

In another embodiment, the carbonyl and the Z group attached to ring A are disposed ortho to each other.

In one embodiment, the invention provides a compound formula II:

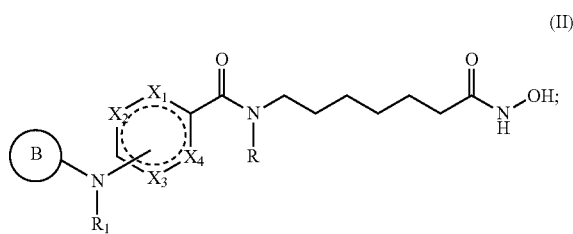

(II)

or a pharmaceutically acceptable salt, ester or prodrug thereof,
wherein,
each of $X_1$, $X_2$, $X_3$, or $X_4$ is independently N, CR', O, S, NCR', CR'CR', OCR', SCR', or absent, or $X_1$ or $X_4$ may be joined with R to form a bicyclic ring; wherein up to three of $X_1$, $X_2$, $X_3$, or $X_4$ may be N;
ring B is an optionally substituted aryl or an optionally substituted heteroaryl;
$R_1$ is H, alkyl, haloalkyl, alkenyl, aryl, arylalkyl, heteroaryl, heterocyclic, carbocyclic, C(O)—$R_2$, or C(O)O—$R_2$, each of which may be optionally substituted;
R is H or an optionally substituted alkyl; or R and $X_1$ or $X_4$ may be joined to form a fused bicyclic ring which may be optionally substituted;
each R' is independently H, optionally substituted alkyl, halo, OH, $NH_2$, NHR'', haloalkyl, CN, $N_3$, $NO_2$;
R'' is H or alkyl; and
$R_2$ is alkyl, cycloalkyl, heterocycloalkyl, aryl, or heteroaryl, each of which is optionally substituted.

In certain embodiments, $X_1$, $X_2$, $X_3$, and $X_4$ are all CR'.
In other embodiments, $X_2$ and $X_3$, are N and $X_1$ and $X_4$ are CR'.
In another embodiment, $X_2$ and $X_3$, are CR' and $X_1$ and $X_4$ are N.
In still other embodiments, $X_2$, is N; $X_3$ is S, N or O; $X_1$ is CR' and $X_4$ is absent.

In one embodiment, ring B is phenyl, pyridinyl, pyrimidinyl, or pyrazinyl; each of which may be optionally substituted.

In a further embodiment, ring B is substituted by alkyl, aryl, heteroaryl, cycloalkyl, heterocycloalkyl, aralkyl, haloalkyl, hal, OH, $NH_2$, NHR'', CN, $N_3$, or $NO_2$.

In certain embodiments, $R_1$ is H, alkyl, aryl, arylalkyl, or heteroaryl, each of which may be optionally substituted.

In another embodiment, the invention provides a compound of formula III:

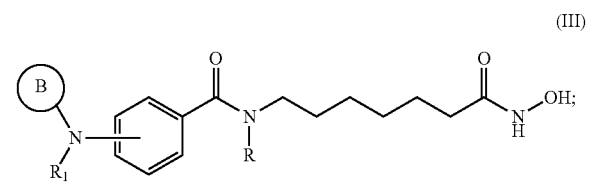

(III)

or a pharmaceutically acceptable salt, ester or prodrug thereof,
wherein,
ring B is an optionally substituted aryl or an optionally substituted heteroaryl;
$R_1$ is H, alkyl, haloalkyl, alkenyl, aryl, arylalkyl, heteroaryl, heterocyclic, carbocyclic, C(O)—$R_2$, or C(O)O—$R_2$, each of which may be optionally substituted;
$R_2$ is optionally substituted heteroaryl, and
R is H or an optionally substituted alkyl; or R and the phenyl ring may be joined to form a fused [6,5] bicyclic ring which may be optionally substituted.

In one embodiment, ring B is phenyl, pyridinyl, pyrimidinyl, or pyrazinyl; each of which may be optionally substituted.

In a further embodiment, ring B is substituted by alkyl, aryl, aralkyl, haloalkyl, hal, OH, $NH_2$, CN, or $NO_2$.

In other embodiments, $R_1$ is H, alkyl, aryl, arylalkyl, heteroaryl, C(O)—$R_2$, or C(O)O—$R_2$, each of which may be optionally substituted.

In various embodiments, $R_2$ is optionally substituted pyridinyl.

In another embodiment, the invention provides a compound of formula IV:

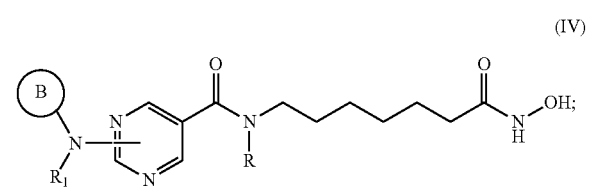

(IV)

or a pharmaceutically acceptable salt, ester or prodrug thereof,
wherein,
ring B is an optionally substituted aryl or an optionally substituted heteroaryl;
$R_1$ is H, alkyl, haloalkyl, alkenyl, aryl, arylalkyl, heteroaryl, heterocyclic, or carbocyclic, each of which may be optionally substituted;
or ring B and $R_1$ may together with the atom to which each is attached, form an optionally substituted heterocyclic, or an optionally substituted heteroaryl, and R is H or an optionally substituted alkyl; or R and the 1,3-pyrimidinyl ring may be joined to form a fused bicyclic ring which may be optionally substituted.

In certain embodiments, ring B is phenyl, pyridinyl, pyrimidinyl, or pyrazinyl; each of which may be optionally substituted.

In a further embodiment, ring B is substituted by alkyl, aryl, aralkyl, haloalkyl, halo, OH, $NH_2$, CN, or $NO_2$.

In other embodiments, $R_1$ is H, alkyl, aryl, arylalkyl, or heteroaryl, each of which may be optionally substituted.

In another embodiment, $R_1$ is substituted by OH or halo.

In another embodiment, the invention provides a compound of formula IVa:

(IVa)

$$\text{[chemical structure]}$$

or a pharmaceutically acceptable salt, ester or prodrug thereof,
wherein,
B is phenyl, pyridinyl, pyrimidinyl, or pyrazinyl; each of which may be optionally substituted by $C_{1-8}$-alkyl, $C_{1-8}$-alkoxy, $C_{6-10}$-aryl, halo-$C_{1-8}$-alkyl, halo, OH, $NH_2$, CN, or $NO_2$;

$R_1$ is phenyl, pyridinyl, pyrimidinyl, or pyrazinyl; each of which may be optionally substituted by $C_{1-8}$-alkyl, $C_{1-8}$-alkoxy, $C_{6-10}$-aryl, halo-$C_{1-8}$-alkyl, halo, OH, $NH_2$, CN, or $NO_2$;
and
R is H or $C_{1-8}$-alkyl.

In an embodiment of formula IVa, $R_1$ is substituted by OH or halo. In still another embodiment, B is phenyl, pyridinyl, or pyrimidinyl, each of which may be optionally substituted by $C_{1-8}$-alkyl, halo, or $C_{1-8}$-alkoxy. In yet another embodiment, $R_1$ is phenyl, pyridinyl, or pyrimidinyl, each of which may be optionally substituted by $C_{1-8}$-alkyl, halo, or $C_{1-8}$-alkoxy.

In certain embodiments, the ring formed by ring B and $R_1$ is piperidine, pyrrolidine, tetrahydroquinoline, morpholine, piperazine, tetrahydro-triazolo pyrazine, or diazepane, each of which is optionally substituted.

In another embodiment, the invention provides a compound of formula V:

(V)

$$\text{[chemical structure]}$$

or a pharmaceutically acceptable salt, ester or prodrug thereof,
wherein,
each of $X_1$, $X_2$, or $X_3$ is independently N or CR';
ring B is an optionally substituted aryl or an optionally substituted heteroaryl;

$R_1$ is H, alkyl, haloalkyl, alkenyl, aryl, arylalkyl, heteroaryl, heterocyclic, or carbocyclic, each of which may be optionally substituted;

each $R_A$ and $R_B$ is independently H, $NH(R_C)$, $N(R_C)(R_C)$, $N(R_C)CO(R_C)$, $CO_2H$, $C(O)R_C$, $C(O)OR_C$, $C(O)NH_2$, $C(O)NH(R_C)$, $C(O)N(R_C)(R_C)$, $SO_2R_C$, $SOR_C$, $SR_C$, alkyl, aryl, arylalkyl, alkoxy, heteroaryl, heterocyclic, and carbocyclic, each of which may be further substituted; or $R_A$ and $R_B$ together with the carbon to which they are attached form a carbonyl;

each $R_C$ is independently H, alkyl, alkenyl, aryl, heteroaryl, cycloalkyl, or heterocyclic, each of which may be further substituted;

R' is H, optionally substituted alkyl, halo, OH, $NH_2$, NHR", haloalkyl, CN, $N_3$, $NO_2$;
R" is H or alkyl; and
m is 1 or 2.

In a related embodiment, the invention provides a compound of formula Va:

(Va)

$$\text{[chemical structure]}$$

or a pharmaceutically acceptable salt, ester or prodrug thereof,
wherein,
each of $X_1$, $X_2$, or $X_3$ is independently N or CR';
ring B is an optionally substituted aryl or an optionally substituted heteroaryl;

$R_1$ is H, alkyl, haloalkyl, alkenyl, aryl, arylalkyl, heteroaryl, heterocyclic, or carbocyclic, each of which may be optionally substituted;

each $R_A$ and $R_B$ is independently H, $NH(R_C)$, $N(R_C)(R_C)$, $N(R_C)CO(R_C)$, $CO_2H$, $C(O)R_C$, $C(O)OR_C$, $C(O)NH_2$, $C(O)NH(R_C)$, $C(O)N(R_C)(R_C)$, $SO_2R_C$, $SOR_C$, $SR_C$, alkyl, aryl, arylalkyl, alkoxy, heteroaryl, heterocyclic, and carbocyclic, each of which may be further substituted; or $R_A$ and $R_B$ together with the carbon to which they are attached form a carbonyl;

each $R_C$ is independently H, alkyl, alkenyl, aryl, heteroaryl, cycloalkyl, or heterocyclic, each of which may be further substituted;

R' is H, optionally substituted alkyl, halo, OH, $NH_2$, NHR", haloalkyl, CN, $N_3$, $NO_2$;
R" is H or alkyl; and
m is 1 or 2.

In one embodiment, $X_1$, $X_2$, and $X_3$, are all independently CR'.

In another embodiment, ring B is phenyl, pyridinyl, pyrimidinyl, or pyrazinyl; each of which may be optionally substituted.

In a further embodiment, ring B is substituted by alkyl, aryl, heteroaryl, cycloalkyl, heterocycloalkyl, aralkyl, haloalkyl, halo, OH, $NH_2$, NHR", CN, $N_3$, or $NO_2$.

In certain embodiments, $R_1$ is H, alkyl, aryl, arylalkyl, or heteroaryl, each of which may be optionally substituted.

In another embodiment, the invention provides a compound of formula VI:

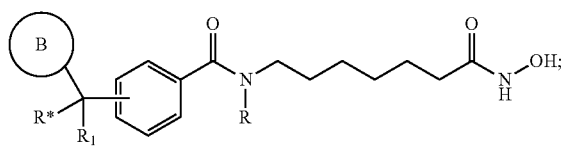

(VI)

or a pharmaceutically acceptable salt, ester or prodrug thereof,
wherein,
ring B is an optionally substituted aryl or an optionally substituted heteroaryl;
R* is an optionally substituted alkyl, an optionally substituted aryl or an optionally substituted heteroaryl;
$R_1$ is H, alkyl, aryl, arylalkyl, heteroaryl, heterocyclic, carbocyclic, OH, alkoxy, $NH_2$, NH(alkyl), or N(alkyl)(alkyl);
or R* and $R_1$ together with the atom to which each is attached, may form an optionally substituted carbocyclic, optionally substituted heterocyclic, optionally substituted aryl or optionally substituted heteroaryl ring; and
R is H or an optionally substituted alkyl.

In one embodiment, ring B is phenyl, pyridinyl, pyrimidinyl, pyrazinyl, or thiazole; each of which may be optionally substituted.

In another embodiment, R* is methyl, trifluoromethyl, phenyl, pyridinyl, pyrimidinyl, pyrazinyl, or thiazole; each of which may be optionally substituted.

In certain embodiments, $R_1$ is OH, methoxy, or ethoxy.

In various embodiments, ring B and R* are each independently substituted with one or more of alkyl, halogen, or $C(O)NR_XR_Y$, wherein $R_X$ is H or alkyl, and $R_Y$ is H or alkyl.

In other embodiments, ring B and R* are each independently substituted with one or more of methyl, F, or $C(O)N(Me)_2$.

In another aspect, the invention provides a pharmaceutical composition comprising a compound of formula I, or a pharmaceutically acceptable ester, salt, or prodrug thereof, together with a pharmaceutically acceptable carrier.

Representative reverse amide inhibitor compounds of the invention include, but are not limited to, the following compounds of Table 2 below. Table 2 illustrates the inhibitory activity against HDAC6 and HDAC3 for the selected representative reverse amide inhibitor compounds of the invention. HDAC enzyme assays were performed as described below. A lower $IC_{50}$ (nM) for HDAC6 compared to HDAC3 indicates that the inhibitor compound is HDAC6-selective.

TABLE 2

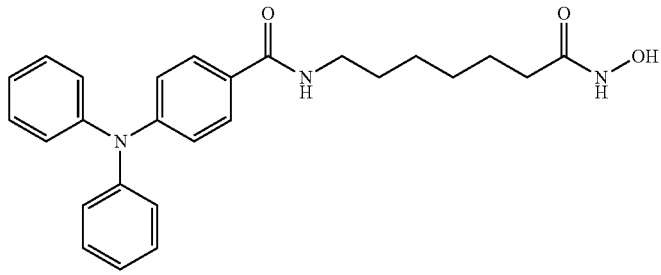

4-(diphenylamino)-N-(7-(hydroxyamino)-7-oxoheptyl)benzamide
$IC_{50}$(nM) HDAC6 = 18 HDAC3 = 316

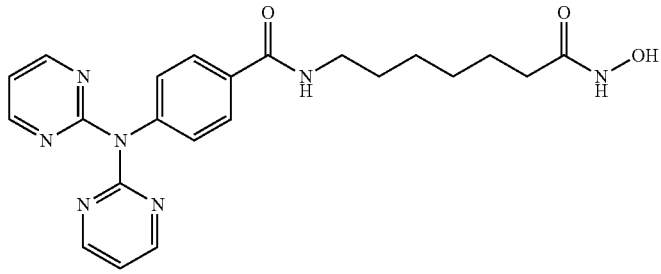

4-(dipyrimidin-2-ylamino)-N-(7-(hydroxyamino)-7-oxoheptyl)benzamide
$IC_{50}$(nM) HDAC6 = 174 HDAC3 = 1089

TABLE 2-continued
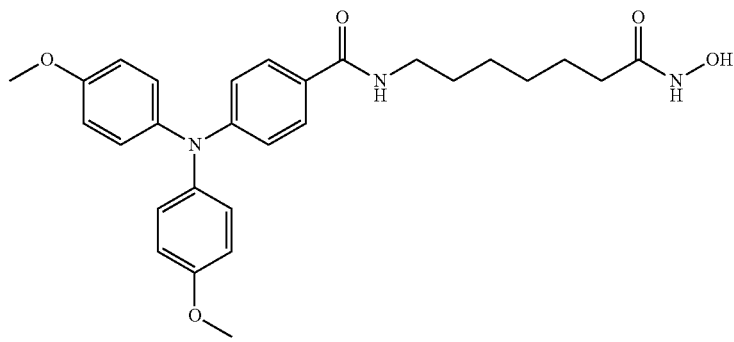
4-(bis(4-methoxyphenyl)amino)-N-(7-
(hydroxyamino)-7-oxoheptyl)benzamide
IC$_{50}$(nM) HDAC6 = 200  HDAC3 = 2001
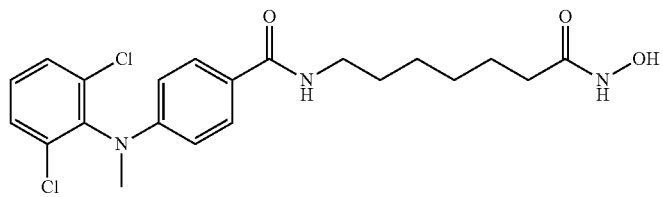
4-((2,6-dichlorophenyl)(methyl)amino)-N-(7-
(hydroxyamino)-7-oxoheptyl)benzamide
IC$_{50}$(nM) HDAC6 = 3  HDAC3 = 29
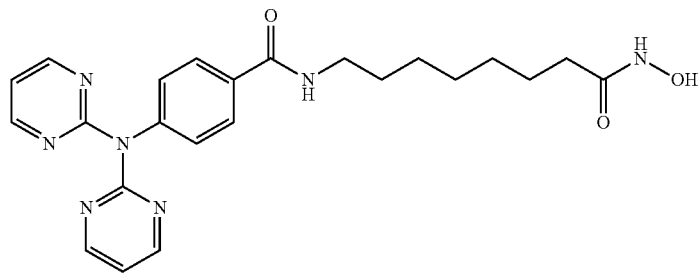
4-(dipyrimidin-2-ylamino)-N-(8-
(hydroxyamino)-8-oxooctyl)benzamide
IC$_{50}$(nM) HDAC6 = 110  HDAC3 = 208
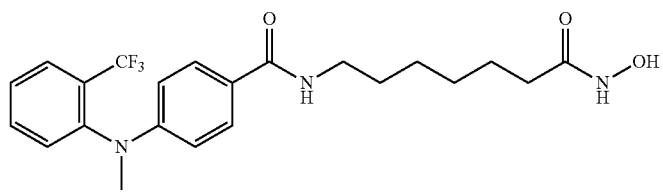
N-(7-(hydroxyamino)-7-oxoheptyl)-4-
(methyl(2-(trifluoromethyl)phenyl)
amino)benzamide
IC$_{50}$(nM) HDAC6 = 3  HDAC3 = 36

TABLE 2-continued

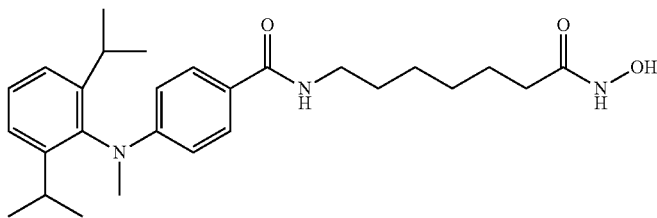

4-((2,6-diisopropylphenyl)(methyl)amino)-N-
(7-(hydroxyamino)-7-oxoheptyl)benzamide
IC$_{50}$(nM) HDAC6 = 45 HDAC3 = 1074

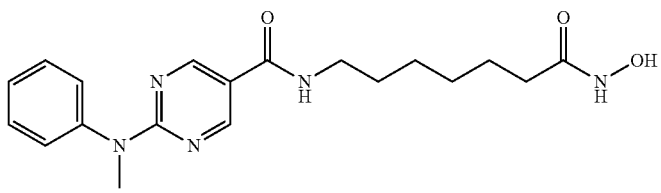

N-(7-(hydroxyamino)-7-oxoheptyl)-2-
(methyl(phenyl)amino)pyrimidine-5-
carboxamide
IC$_{50}$(nM) HDAC6 = 6 HDAC3 = 47

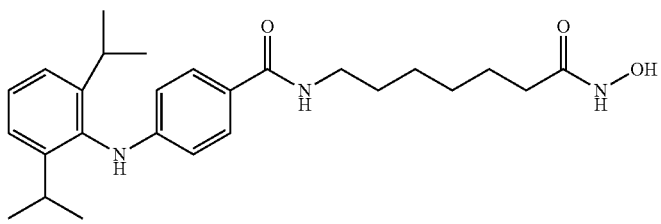

4-(2,6-diisopropylphenylamino)-N-(7-
(hydroxyamino)-7-oxoheptyl)benzamide
IC$_{50}$(nM) HDAC6 = 20 HDAC3 = 369

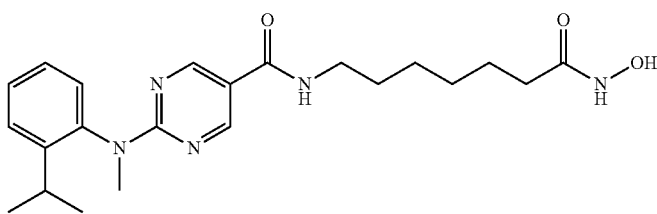

N-(7-(hydroxyamino)-7-oxoheptyl)-2-((2-
isopropylphenyl)(methyl)amino)pyrimidine-
5-carboxamide
IC$_{50}$(nM) HDAC6 = 7 HDAC3 = 73

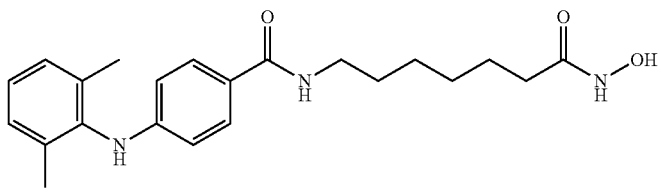

4-(2,6-dimethylphenylamino)-N-(7-
(hydroxyamino)-7-oxoheptyl)benzamide
IC$_{50}$(nM) HDAC6 = 3 HDAC3 = 59

TABLE 2-continued

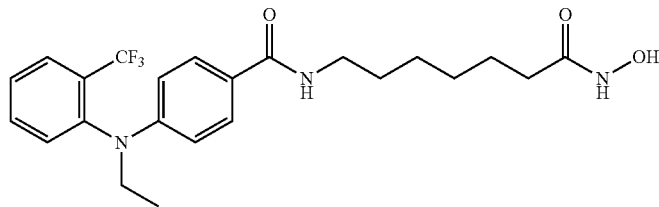

4-(ethyl(2-(trifluoromethyl)phenyl)amino)-N-
(7-(hydroxyamino)-7-oxoheptyl)benzamide
IC$_{50}$(nM) HDAC6 = 5 HDAC3 = 46

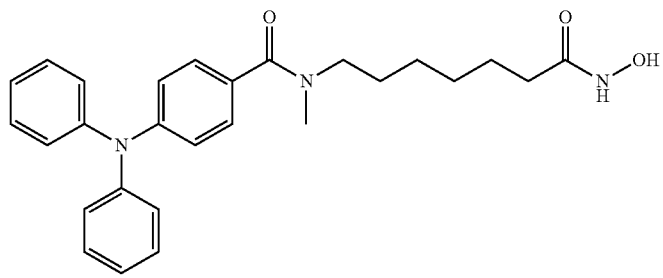

4-(diphenylamino)-N-(7-(hydroxyamino)-7-
oxoheptyl)-N-methylbenzamide
IC$_{50}$(nM) HDAC6 = 82 HDAC3 = 313

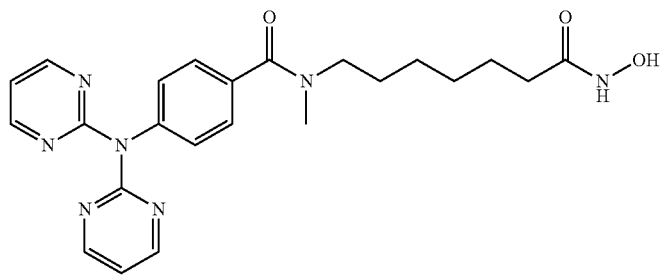

4-(dipyrimidin-2-ylamino)-N-(7-
(hydroxyamino)-7-oxoheptyl)-N-
methylbenzamide
IC$_{50}$(nM) HDAC6 = 198 HDAC3 = 1237

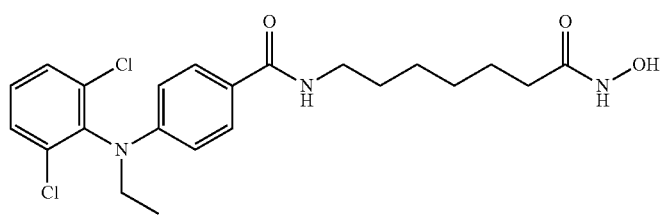

4-((2,6-dichlorophenyl)(ethyl)amino)-N-(7-
(hydroxyamino)-7-oxoheptyl)benzamide
IC$_{50}$(nM) HDAC6 = 8 HDAC3 = 71

TABLE 2-continued

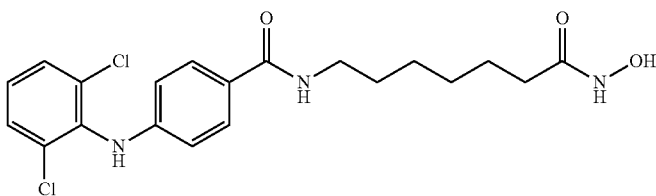

4-(2,6-dichlorophenylamino)-N-(7-
(hydroxyamino)-7-oxoheptyl)benzamide
IC$_{50}$(nM) HDAC6 = 3 HDAC3 = 28

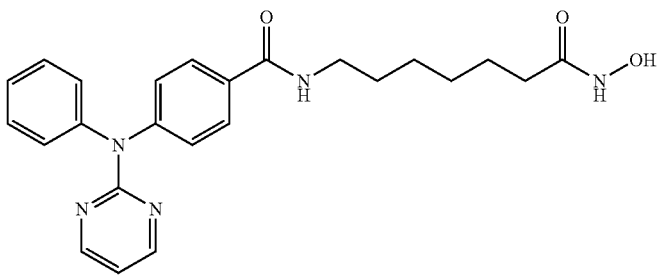

N-(7-(hydroxyamino)-7-oxoheptyl)-4-
(phenyl(pyrimidin-2-yl)amino)benzamide
IC$_{50}$(nM) HDAC6 = 3 HDAC3 = 65

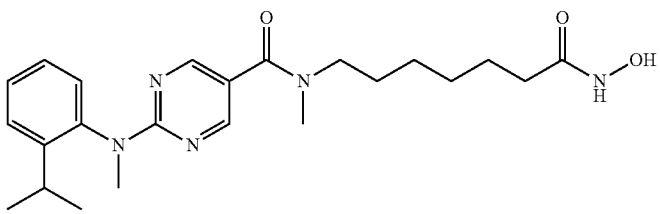

N-(7-(hydroxyamino)-7-oxoheptyl)-2-((2-
isopropylphenyl)(methyl)amino)-N-
methylpyrimidine-5-carboxamide
IC$_{50}$(nM) HDAC6 = 50 HDAC3 = 642

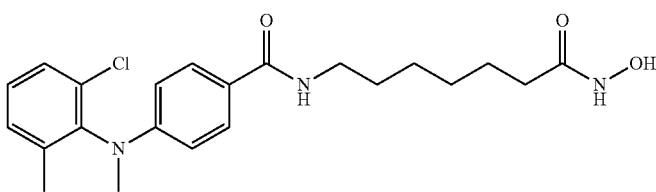

4-((2-chloro-6-methylphenyl)(methyl)amino)-
N-(7-(hydroxyamino)-7-oxoheptyl)benzamide
IC$_{50}$(nM) HDAC6 = 4 HDAC3 = 58

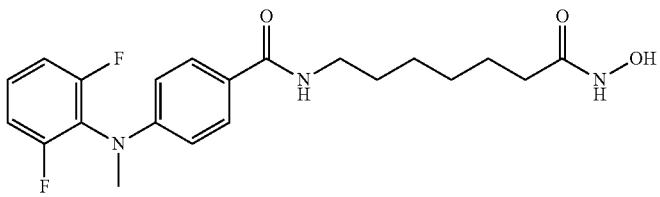

4-((2,6-difluorophenyl)(methyl)amino)-N-(7-
(hydroxyamino)-7-oxoheptyl)benzamide
IC$_{50}$(nM) HDAC6 = 2 HDAC3 = 17

TABLE 2-continued

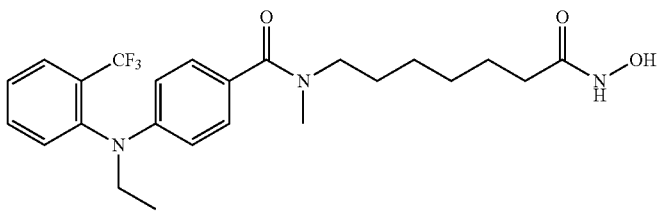

4-(ethyl(2-(trifluoromethyl)phenyl)amino)-N-
(7-(hydroxyamino)-7-oxoheptyl)-N-
methylbenzamide
IC$_{50}$(nM) HDAC6 = 39 HDAC3 = 58

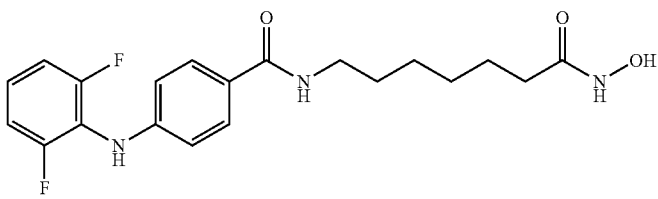

4-(2,6-(difluorophenylamino)-N-(7-
(hydroxyamino)-7-oxoheptyl)benzamide
IC$_{50}$(nM) HDAC6 = 3 HDAC3 = 25

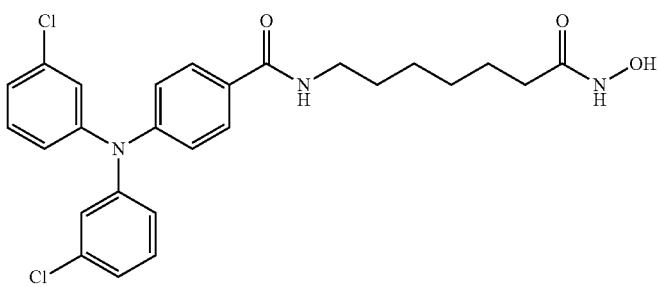

4-(bis(3-chlorophenyl)amino)-N-(7-
(hydroxyamino)-7-oxoheptyl)benzamide
IC$_{50}$(nM) HDAC6 = 858 HDAC3 = 11813

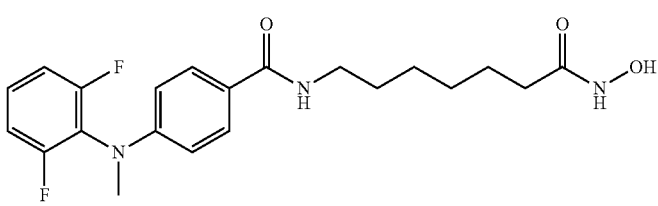

7-(4-((2,6-difluorophenyl)(methyl)
amino)benzylamino)-N-hydroxy heptanamide
IC$_{50}$(nM) HDAC6 = 121 HDAC3 = 67

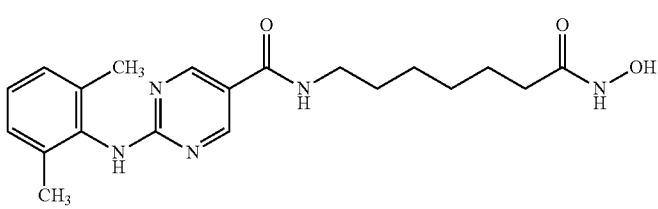

2-(2,6-dimethylphenylamino)-N-(7-
(hydroxyamino)-7-oxoheptyl)pyrimidine-5-
carboxamide
IC$_{50}$(nM) HDAC6 = 33 HDAC3 = 505

TABLE 2-continued

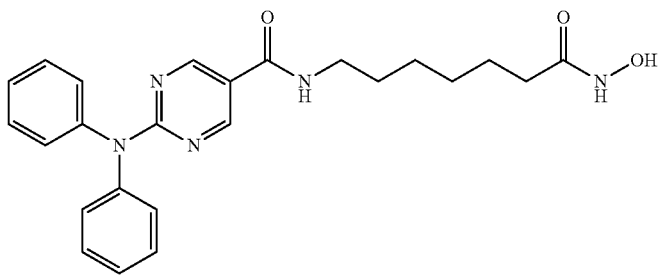

2-(diphenylamino)-N-(7-(hydroxyamino)-7-
oxoheptyl)pyrimidine-5-carboxamide
IC$_{50}$(nM) HDAC6 = 10 HDAC3 = 84

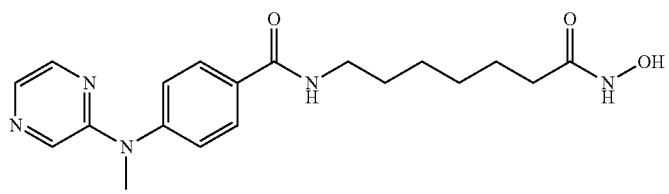

N-(7-(hydroxyamino)-7-oxoheptyl)-4-
(methyl(pyrazin-2-yl)amino)benzamide
IC$_{50}$(nM) HDAC6 = 21 HDAC3 = 93

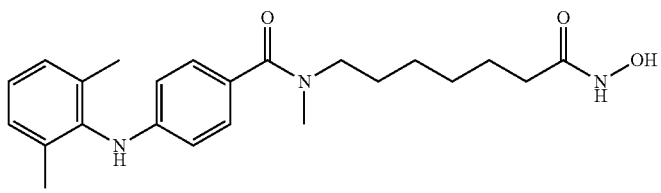

4-(2,6-dimethylphenylamino)-N-(7-
(hydroxyamino)-7-oxoheptyl)-N-
methylbenzamide
IC$_{50}$(nM) HDAC6 = 7 HDAC3 = 304

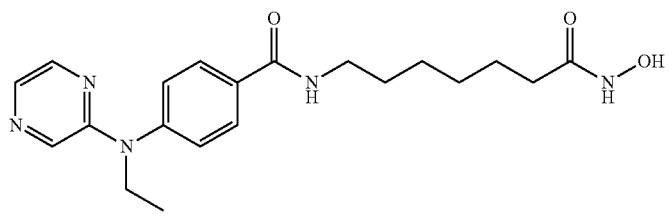

4-(ethyl(pyrazin-2-yl)amino)-N-(7-
(hydroxyamino)-7-oxoheptyl)benzamide
IC$_{50}$(nM) HDAC6 = 11 HDAC3 = 93

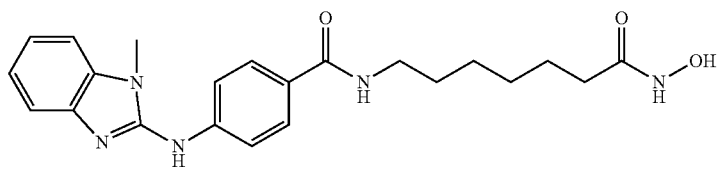

N-(7-(hydroxyamino)-7-oxoheptyl)-4-(1-
methyl-1H-benzo[d]imidazol-2-
ylamino)benzamide
IC$_{50}$(nM) HDAC6 = 9 HDAC3 = 57

TABLE 2-continued

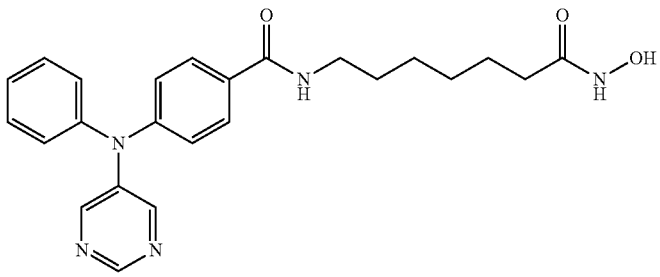

N-(7-(hydroxyamino)-7-oxoheptyl)-4-
(phenyl(pyrimidin-5-yl)amino)benzamide
IC$_{50}$(nM) HDAC6 = 12 HDAC3 = 92

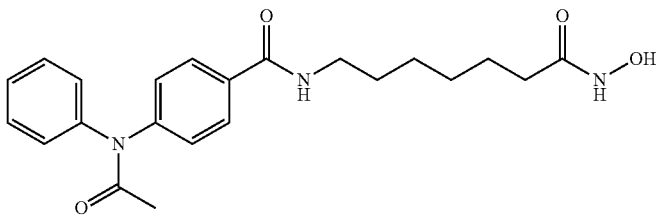

N-(7-(hydroxyamino)-7-oxoheptyl)-4-(N-
phenylacetamido)benzamide
IC$_{50}$(nM) HDAC6 = 3 HDAC3 = 67

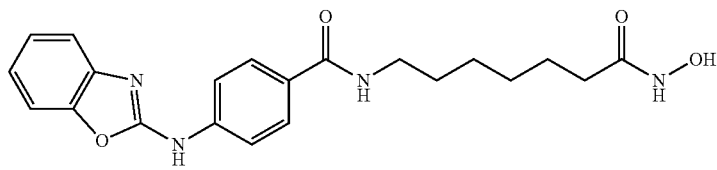

4-(benzo[d]oxazol-2-ylamino)-N-(7-
(hydroxyamino)-7-oxoheptyl)benzamide
IC$_{50}$(nM) HDAC6 = 3 HDAC3 = 22

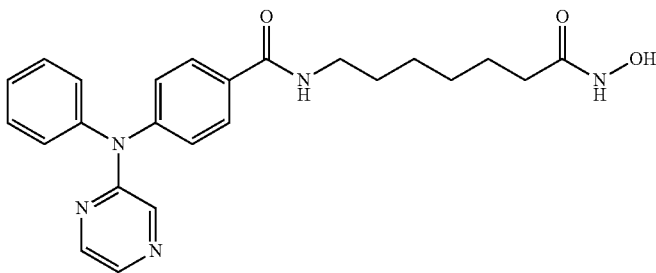

N-(7-(hydroxyamino)-7-oxoheptyl)-4-
(phenyl(pyrazin-2-yl)amino)benzamide
IC$_{50}$(nM) HDAC6 = 14 HDAC3 = 64

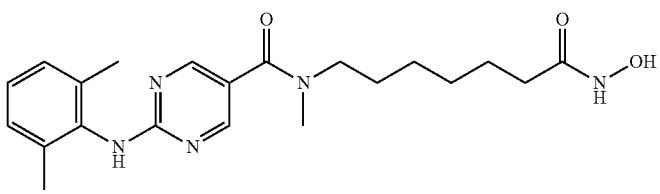

2-(2,6-dimethylphenylamino)-N-(7-
(hydroxyamino)-7-oxoheptyl)-N-
methylpyrimidine-5-carboxamide
IC$_{50}$(nM) HDAC6 = 33 HDAC3 = 387

TABLE 2-continued
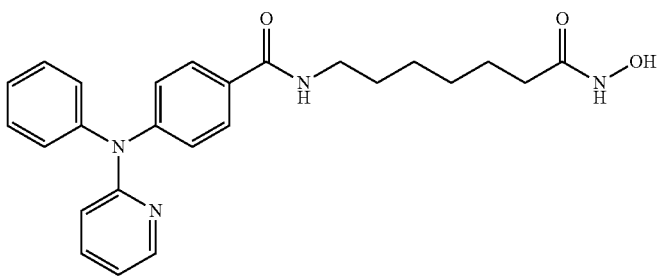
N-(7-(hydroxyamino)-7-oxoheptyl)-4-
(phenyl(pyridin-2-yl)amino)benzamide
$IC_{50}$(nM) HDAC6 = 14 HDAC3 = 61
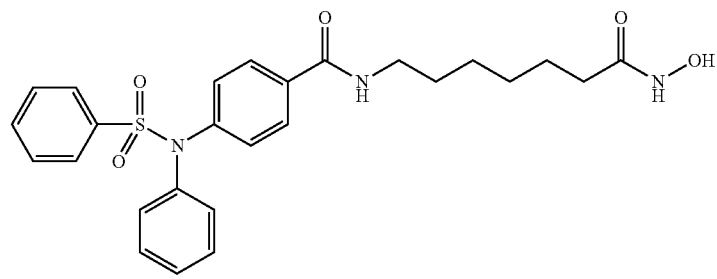
N-(7-(hydroxyamino)-7-oxoheptyl)-4-(N-
phenylphenylsulfonamido)benzamide
$IC_{50}$(nM) HDAC6 = 15 HDAC3 = 84
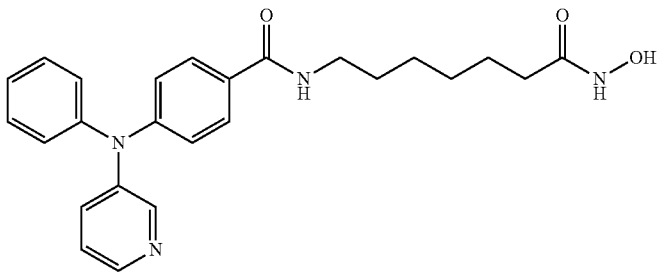
N-(7-(hydroxyamino)-7-oxoheptyl)-4-
(phenyl(pyridin-3-yl)amino)benzamide
$IC_{50}$(nM) HDAC6 = 21 HDAC3 = 66
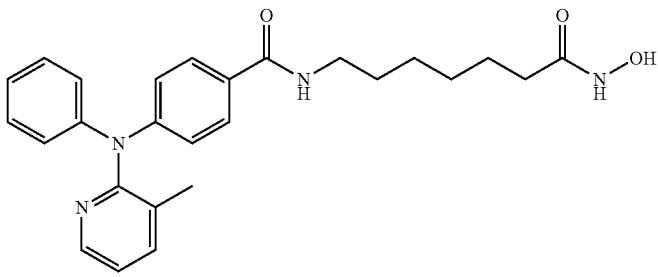
N-(7-(hydroxyamino)-7-oxoheptyl)-4-((3-
methylpyridin-2-yl)(phenyl)amino)benzamide
$IC_{50}$(nM) HDAC6 = 20 HDAC3 = 69

TABLE 2-continued

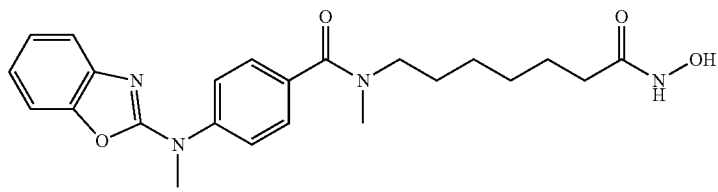

4-(benzo[d]oxazol-2-yl(methyl)amino)-N-(7-
(hydroxyamino)-7-oxoheptyl)-N-
methylbenzamide
IC$_{50}$(nM) HDAC6 = 107 HDAC3 = 294

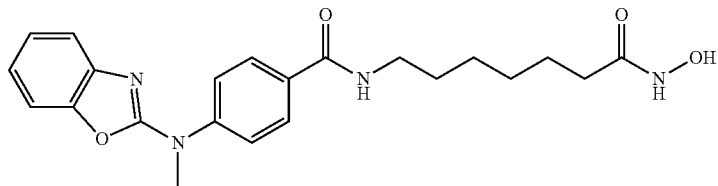

4-(benzo[d]oxazol-2-yl(methyl)amino)-N-(7-
(hydroxyamino)-7-oxoheptyl)benzamide
IC$_{50}$(nM) HDAC6 = 11 HDAC3 = 83

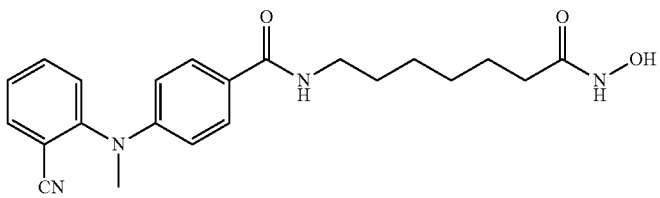

4-((2-cyanophenyl)(methyl)amino)-N-(7-
(hydroxyamino)-7-oxoheptyl)benzamide
IC$_{50}$(nM) HDAC6 = 4 HDAC3 = 23

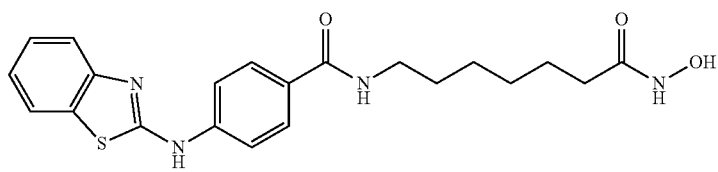

4-(benzo[d]oxazol-2-ylamino)-N-(7-
(hydroxyamino)-7-oxoheptyl)benzamide
IC$_{50}$(nM) HDAC6 = 12 HDAC3 = 22

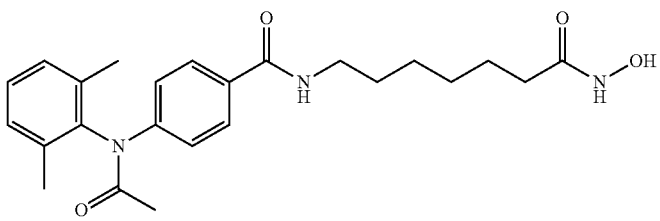

4-(N-(2,6-dimethylphenyl)acetamido)-N-(7-
(hydroxyamino)-7-oxoheptyl)benzamide
IC$_{50}$(nM) HDAC6 = 22 HDAC3 = 198

TABLE 2-continued

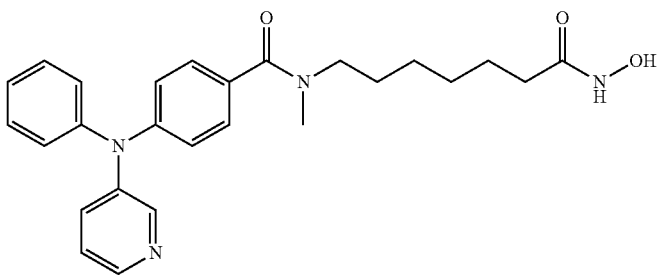

N-(7-(hydroxyamino)-7-oxoheptyl)-N-methyl-
4-(phenyl(pyridin-3-yl)amino)benzamide
IC$_{50}$(nM) HDAC6 = 64 HDAC3 = 85

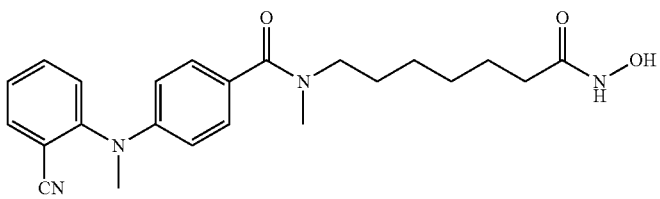

4-((2-cyanophenyl)(methyl)amino)-N-(7-
(hydroxyamino)-7-oxoheptyl)-N-
methylbenzamide
IC$_{50}$(nM) HDAC6 = 35 HDAC3 = 135

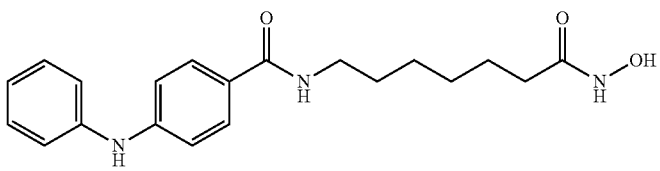

N-(7-(hydroxyamino)-7-oxoheptyl)-4-
(phenylamino)benzamide
IC$_{50}$(nM) HDAC6 = 7 HDAC3 = 16

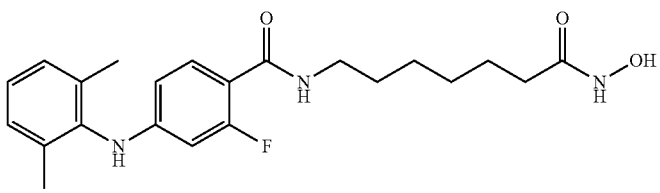

4-(2,6-dimethylphenylamino)-2-fluoro-N-(7-
(hydroxyamino)-7-oxoheptyl)benzamide
IC$_{50}$(nM) HDAC6 = 3 HDAC3 = 95

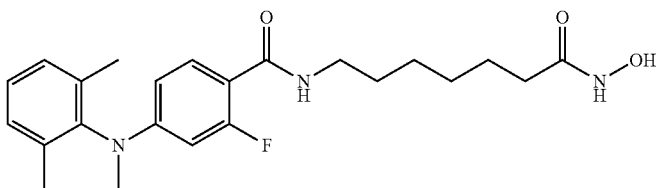

4-((2,6-dimethylphenyl)(methyl)amino)-2-
fluoro-N-(7-(hydroxyamino)-7-
oxoheptyl)benzamide
IC$_{50}$(nM) HDAC6 = 5 HDAC3 = 107

TABLE 2-continued

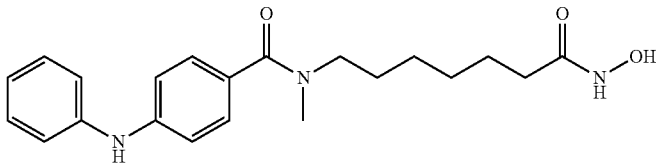

N-(7-(hydroxyamino)-7-oxoheptyl)-4-
methyl-4-(phenylamino)benzamide
IC$_{50}$(nM) HDAC6 = 11 HDAC3 = 50

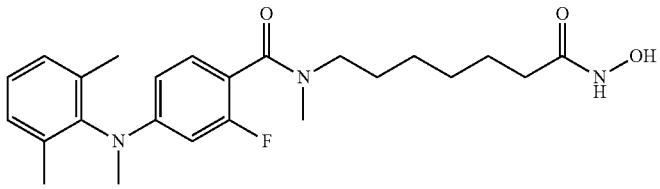

4-((2,6-dimethylphenyl)(methyl)amino)-2-
fluoro-N-(7-(hydroxyamino)-7-oxoheptyl)-N-
methylbenzamide
IC$_{50}$(nM) HDAC6 = 9 HDAC3 = 148

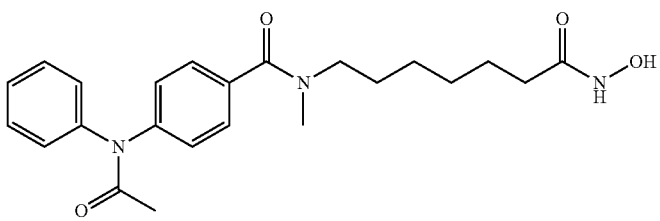

N-(7-(hydroxyamino)-7-oxoheptyl)-N-
methyl-4-(N-phenylacetamido)benzamide
IC$_{50}$(nM) HDAC6 = 37 HDAC3 = 493

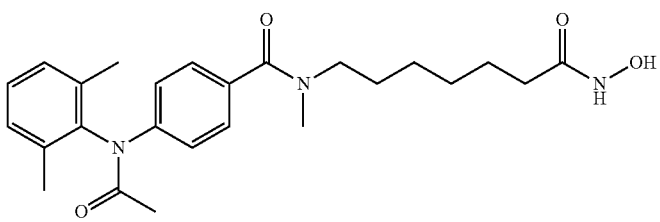

4-(N-(2,6-dimethylphenyl)acetamido)-N-(7-
(hydroxyamino)-7-oxoheptyl)-N-
methylbenzamide
IC$_{50}$(nM) HDAC6 = 25 HDAC3 = 528

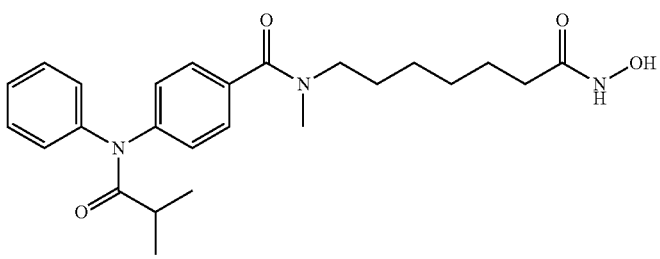

N-(7-(hydroxyamino)-7-oxoheptyl)-N-
methyl-4-(N-phenylisobutyramido)
benzamide
IC$_{50}$(nM) HDAC6 = 67 HDAC3 = 533

TABLE 2-continued

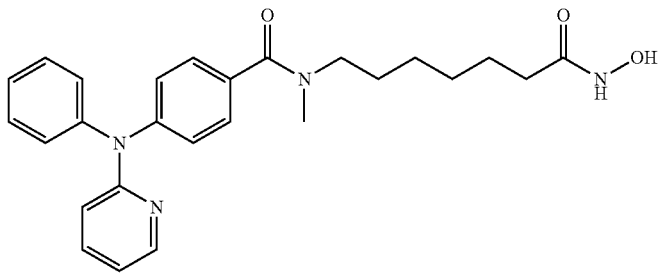

N-(7-(hydroxyamino)-7-oxoheptyl)-N-methyl-
4-(phenyl(pyridin-2-yl)amino)benzamide
IC$_{50}$(nM) HDAC6 = 15 HDAC3 = 100

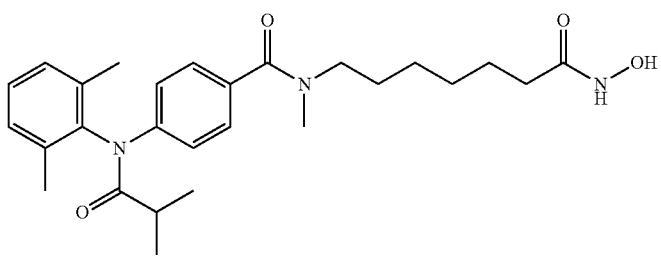

4-(N-(2,6-dimethylphenyl)isobutyramido)-N-
(7-(hydroxyamino)-7-oxoheptyl)-N-
methylbenzamide
IC$_{50}$(nM) HDAC6 = 37 HDAC3 = 386

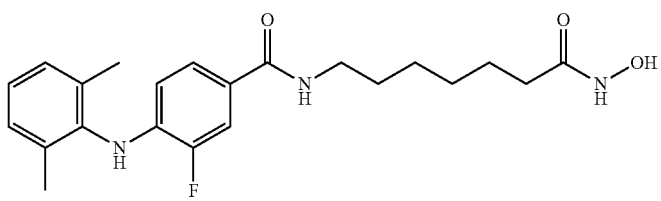

4-(2,6-dimethylphenylamino)-3-fluoro-N-(7-
(hydroxyamino)-7-oxoheptyl)benzamide
IC$_{50}$(nM) HDAC6 = 4 HDAC3 = 80

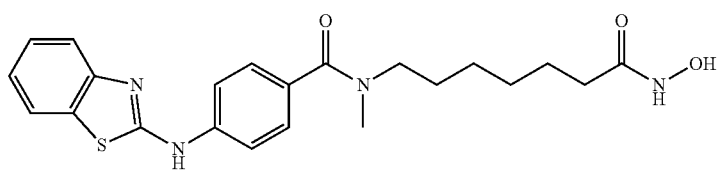

4-(benzo[d]thiazol-2-ylamino)-N-(7-
(hydroxyamino)-7-oxoheptyl)-N-
methylbenzamide
IC$_{50}$(nM) HDAC6 = 20 HDAC3 = 43

TABLE 2-continued

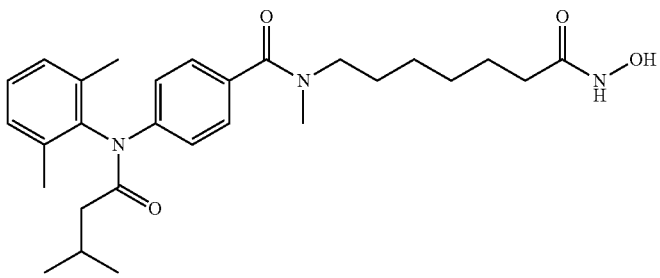

4-(N-(2,6-dimethylphenyl)-3-
methylbutanamido)-N-(7-(hydroxyamino)-7-
oxoheptyl)-N-methylbenzamide
IC$_{50}$(nM) HDAC6 = 66 HDAC3 = 558

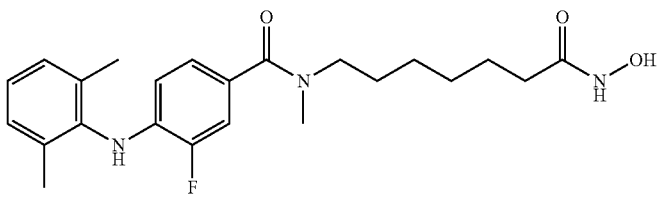

4-(2,6-dimethylphenylamino)-3-fluoro-N-(7-
(hydroxyamino)-7-oxoheptyl)-N-
methylbenzamide
IC$_{50}$(nM) HDAC6 = 12 HDAC3 = 204

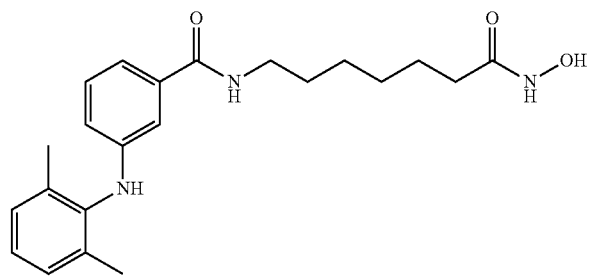

3-(2,6-dimethylphenylamino)-N-(7-
(hydroxyamino)-7-oxoheptyl)benzamide
IC$_{50}$(nM) HDAC6 = 10 HDAC3 = 54

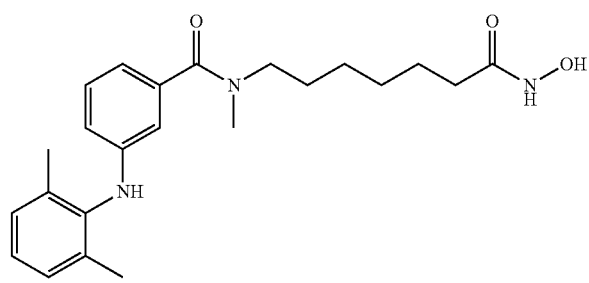

3-(2,6-dimethylphenylamino)-N-(7-
(hydroxyamino)-7-oxoheptyl)-N-
methylbenzamide
IC$_{50}$(nM) HDAC6 = 27 HDAC3 = 186

TABLE 2-continued

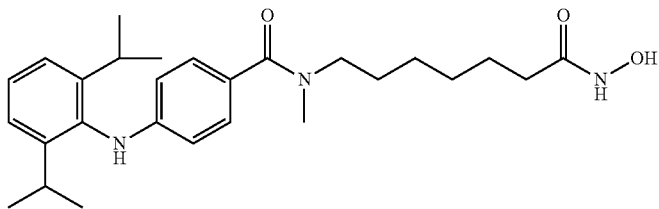

4-(2,6-diisopropylphenylamino)-N-(7-
(hydroxyamino)-7-oxoheptyl)-N-
methylbenzamide
IC$_{50}$(nM) HDAC6 = 109 HDAC3 = 925

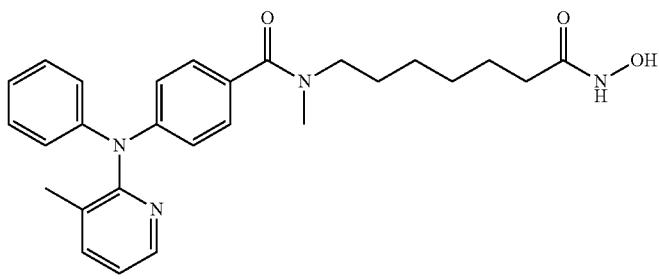

N-(7-(hydroxyamino)-7-oxoheptyl)-N-
methyl-4-((3-methylpyridin-2-
yl)phenyl)amino)benzamide
IC$_{50}$(nM) HDAC6 = 27 HDAC3 = 186

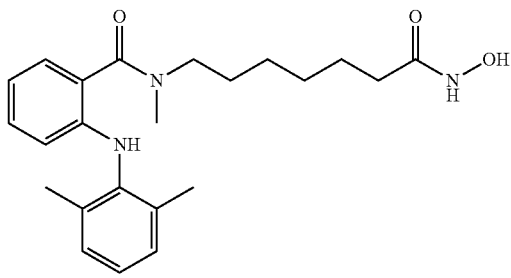

2-(2,6-dimethylphenylamino)-N-(7-
(hydroxyamino)-7-oxoheptyl)-N-
methylbenzamide
IC$_{50}$(nM) HDAC6 = 48 HDAC3 = 242

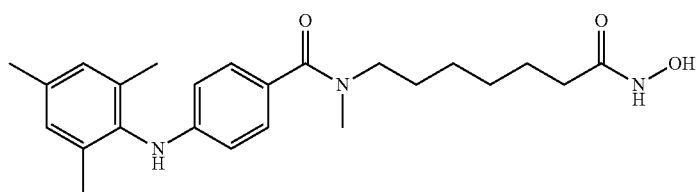

N-(7-(hydroxyamino)-7-oxoheptyl)-4-
(mesitylamino)-N-methylbenzamide
IC$_{50}$(nM) HDAC6 = 35 HDAC3 = 347

TABLE 2-continued

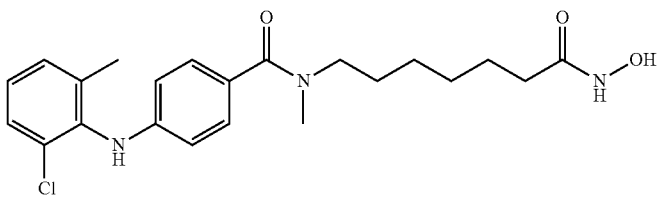

4-(2-chloro-6-methylphenylamino)-N-(7-
(hydroxyamino)-7-oxoheptyl)-N-
methylbenzamide
IC$_{50}$(nM) HDAC6 = 11 HDAC3 = 132

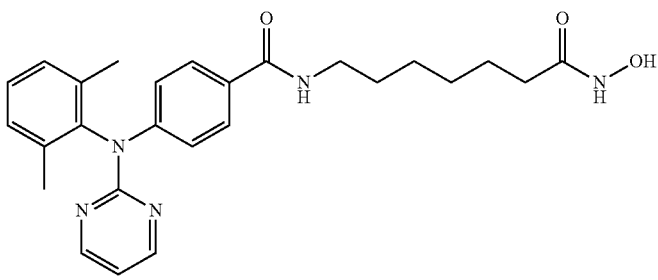

4-((2,6-dimethylphenyl)(pyrimidin-2-
yl)amino)-N-(7-(hydroxyamino)-7-
oxoheptyl)benzamide
IC$_{50}$(nM) HDAC6 = 4 HDAC3 = 85

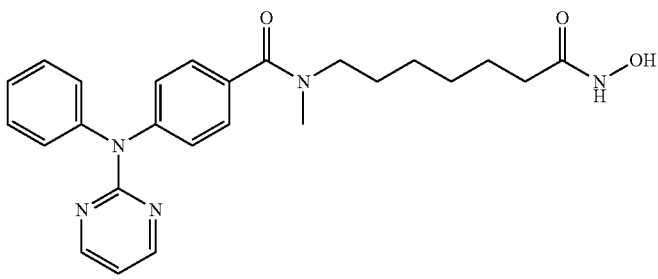

N-(7-(hydroxyamino)-7-oxoheptyl)-N-methyl-
4-(phenyl(pyrimidin-2-yl)amino)benzamide
IC$_{50}$(nM) HDAC6 = 18 HDAC3 = 170

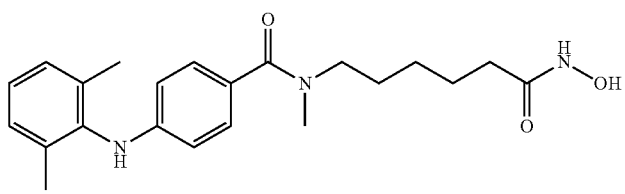

4-(2,6-dimethylphenylamino)-N-(6-
(hydroxyamino)-6-oxoheptyl)-N-
methylbenzamide
IC$_{50}$(nM) HDAC6 = 46 HDAC3 = 304

TABLE 2-continued

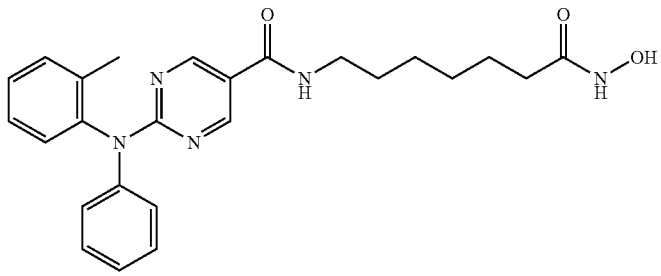

N-(7-(hydroxyamino)-7-oxoheptyl)-2-
(phenyl(o-tolyl)amino)pyrimidine-5-
carboxamide
IC$_{50}$(nM) HDAC6 = 9 HDAC3 = 144

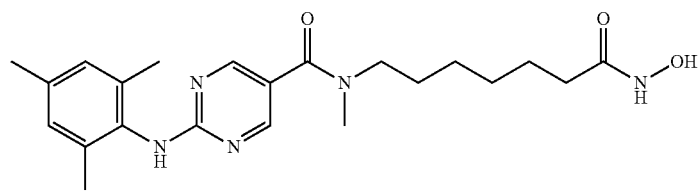

N-(7-(hydroxyamino)-7-oxoheptyl)-2-
(mesitylamino)-N-methylpyrimidine-5-
carboxamide
IC$_{50}$(nM) HDAC6 = 38 HDAC3 = 478

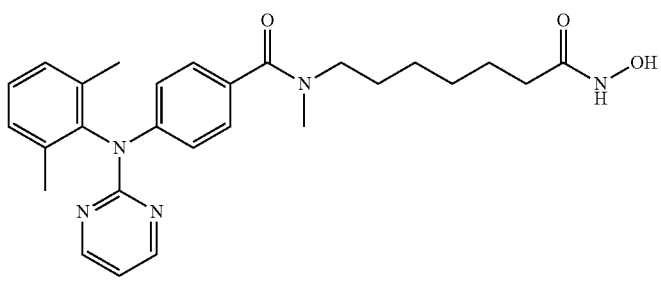

4-((2,6-dimethylphenyl)(pyrimidin-2-yl)amino)-
N-(7-(hydroxyamino)-7-oxoheptyl)-N-
methylbenzamide
IC$_{50}$(nM) HDAC6 = 24 HDAC3 = 297

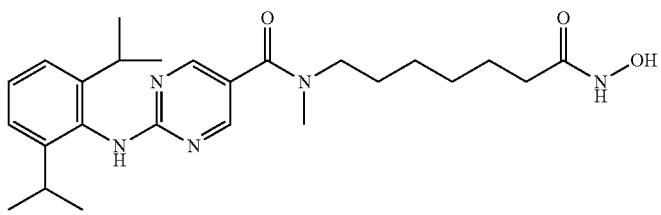

2-(2,6-diisopropylphenylamino)-N-(7-
(hydroxyamino)-7-oxoheptyl)-N-
methylpyrimidine-5-carboxamide
IC$_{50}$(nM) HDAC6 = 51 HDAC3 = 421

TABLE 2-continued
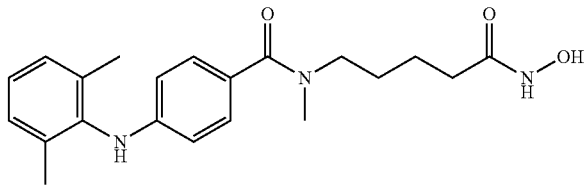
4-(2,6-dimethylphenylamino)-N-(5-
(hydroxyamino)-5-oxopentyl)-N-
methylbenzamide
IC$_{50}$(nM) HDAC6 = 363 HDAC3 = 2066
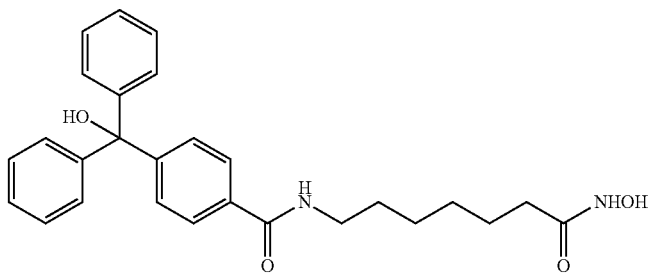
N-(7-(hydroxyamino)-7-oxoheptyl)-4-
(hydroxydiphenylmethyl)benzamide
IC$_{50}$(nM) HDAC6 = 10 HDAC3 = 160
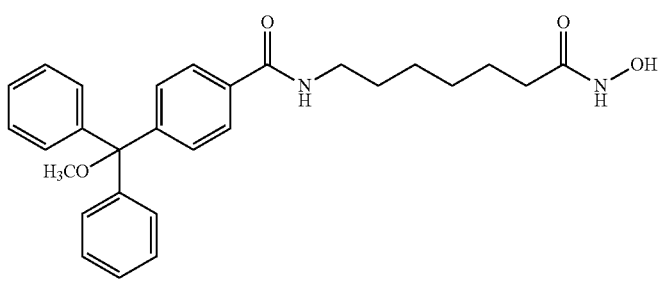
N-(7-(hydroxyamino)-7-oxoheptyl)-4-
(methoxydiphenylmethyl)benzamide
IC$_{50}$(nM) HDAC6 = 7 HDAC3 = 243
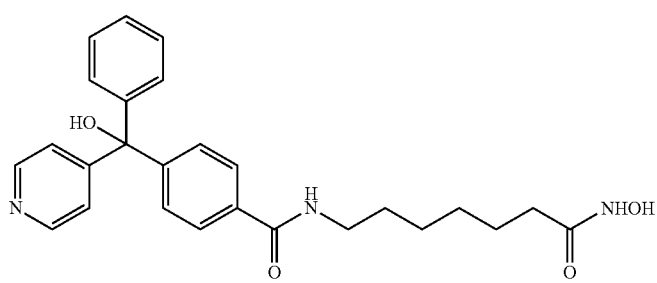
4-(hydroxy(phenyl)(pyridin-4-yl)methyl)-N-
(7-(hydroxyamino)-7-oxoheptyl)benzamide
IC$_{50}$(nM) HDAC6 = 4 HDAC3 = 78

TABLE 2-continued

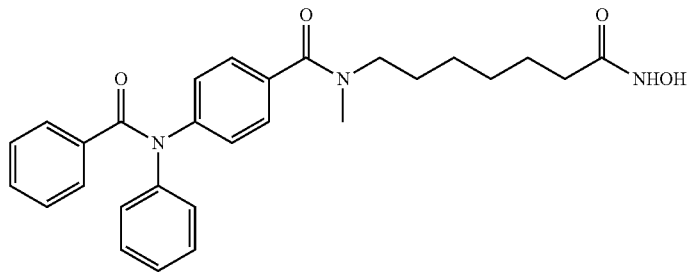

N-(7-(hydroxyamino)-7-oxoheptyl)-N-methyl-
4-(N-phenylbenzamido)benzamide
IC$_{50}$(nM) HDAC6 = 27 HDAC3 = 378

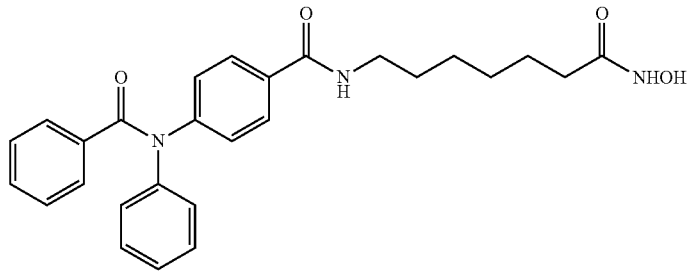

N-(4-(7-(hydroxyamino)-7-
oxoheptylcarbamoyl)phenyl)-N-
phenylbenzamide
IC$_{50}$(nM) HDAC6 = 2 HDAC3 = 67

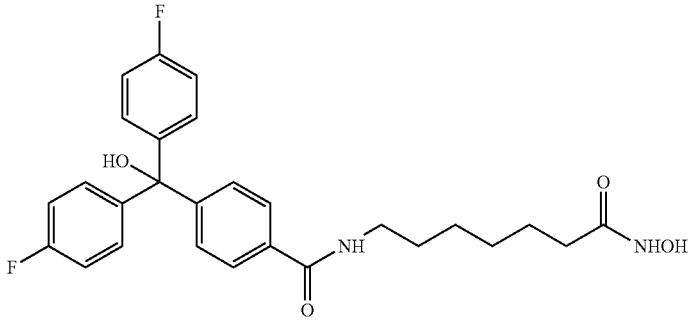

4-(bis(4-fluorophenyl)(hydroxy)methyl)-N-(7-
(hydroxyamino)-7-oxoheptyl)benzamide
IC$_{50}$(nM) HDAC6 = 3 HDAC3 = 121

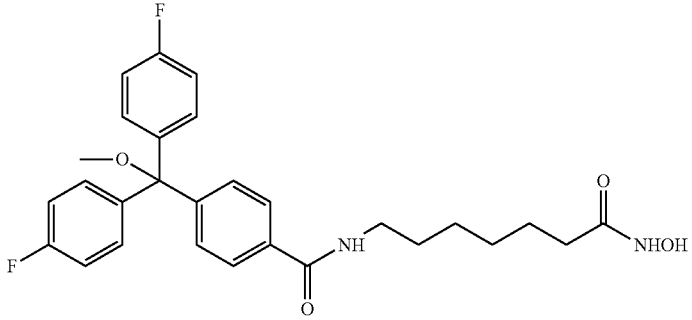

4-(bis(4-fluorophenyl)(methoxy)methyl)-N-
(7-(hydroxyamino)-7-oxoheptyl)benzamide
IC$_{50}$(nM) HDAC6 = 13 HDAC3 = 1225

TABLE 2-continued

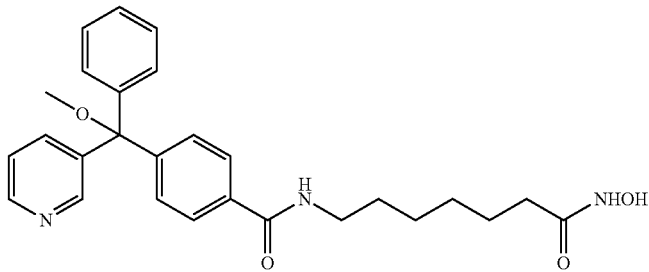

N-(7-(hydroxyamino)-7-oxoheptyl)-4-
(methoxy(phenyl)(pyridin-3-
yl)methyl)benzamide
IC$_{50}$(nM) HDAC6 = 3 HDAC3 = 73

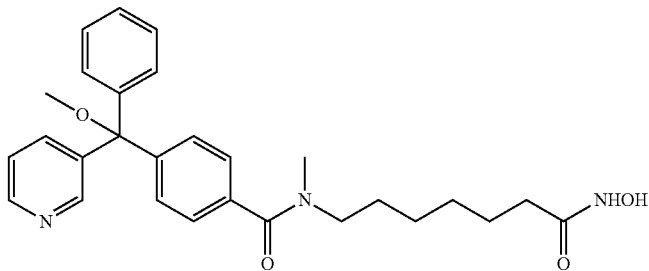

N-(7-(hydroxyamino)-7-oxoheptyl)-4-
(methoxy(phenyl)(pyridin-3-yl)methyl)-N-
methylbenzamide
IC$_{50}$(nM) HDAC6 = 19 HDAC3 = 319

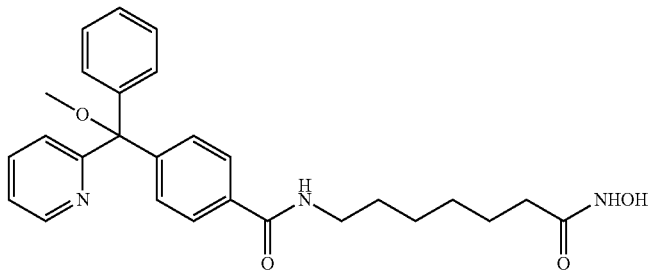

N-(7-(hydroxyamino)-7-oxoheptyl)-4-
(methoxy(phenyl)(pyridin-2-yl)methyl)
benzamide
IC$_{50}$(nM) HDAC6 = 3 HDAC3 = 130

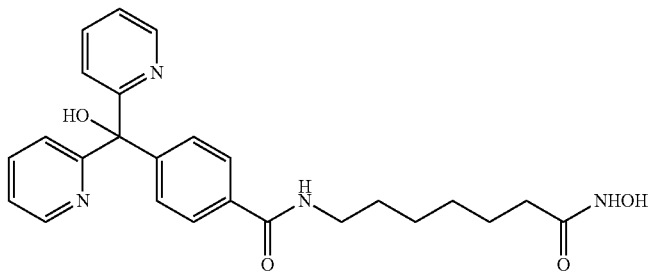

N-(7-(hydroxyamino)-7-oxoheptyl)-4-
(hydroxydipyridin-2-ylmethyl)benzamide
IC$_{50}$(nM) HDAC6 = 4 HDAC3 = 123

TABLE 2-continued

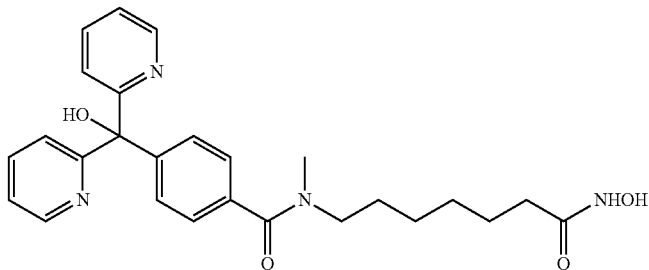

N-(7-(hydroxyamino)-7-oxoheptyl)-4-
(hydroxydipyridin-2-ylmethyl)-N-methyl-
benzamide
IC$_{50}$(nM) HDAC6 = 36 HDAC3 = 550

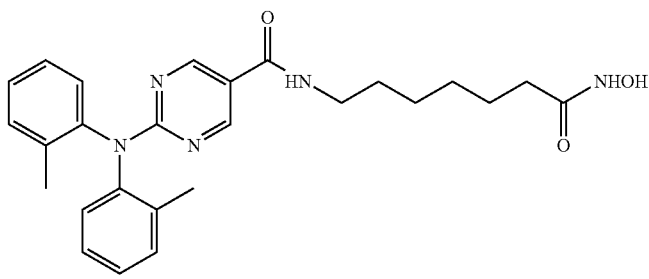

2-(di-o-tolylamino)-N-(7-(hydroxyamino)-7-
oxoheptyl)pyrimidine-5-carboxamide
IC$_{50}$(nM) HDAC6 = 9 HDAC3 = 138

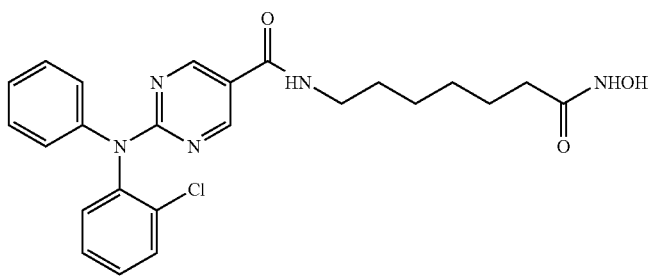

2-((2-chlorophenyl)(phenyl)amino)-N-(7-
(hydroxyamino)-7-oxoheptyl)pyrimidine-5-
carboxamide
IC$_{50}$(nM) HDAC6 = 4 HDAC3 = 76

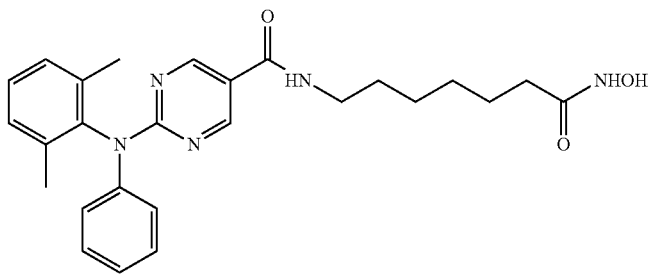

2-((2,6-dimethylphenyl)(phenyl)amino)-N-(7-
(hydroxyamino)-7-oxoheptyl)pyrimidine-5-
carboxamide
IC$_{50}$(nM) HDAC6 = 5 HDAC3 = 137

TABLE 2-continued

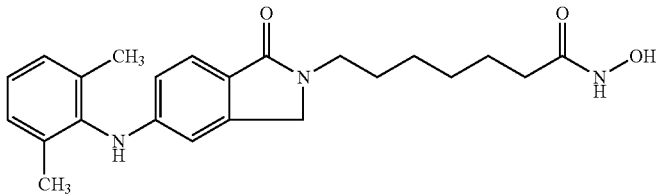

7-(5-(2,6-dimethylphenylamino)-1-
oxoisoindolin-2-yl)-N-hydroxyheptanamide
IC$_{50}$(nM) HDAC6 = 3 HDAC3 = 37

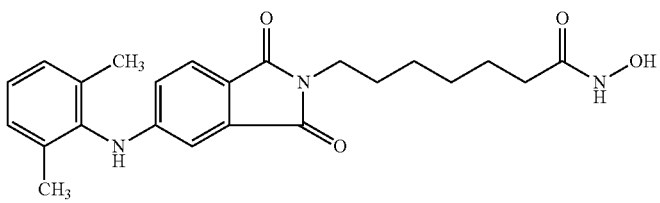

7-(5-(2,6-dimethylphenylamino)-1,3-
dioxoisoindolin-2-yl)-N-hydroxyheptanamide
IC$_{50}$(nM) HDAC6 = TBD HDAC3 = TBD

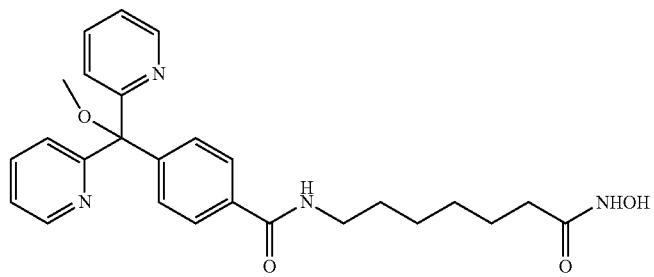

N-(7-(hydroxyamino)-7-oxoheptyl)-4-
(methoxydipyridin-2-ylmethyl)benzamide
IC$_{50}$(nM) HDAC6 = TBD HDAC3 = TBD

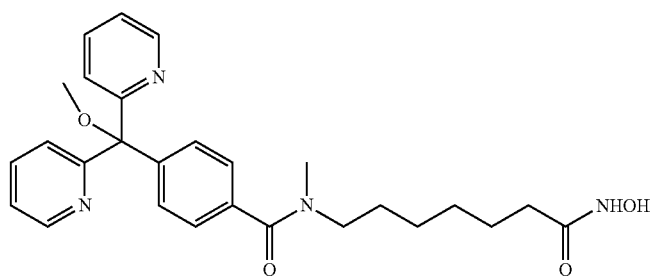

N-(7-(hydroxyamino)-7-oxoheptyl)-4-
(methoxydipyridin-2-ylmethyl)-N-
methylbenzamide
IC$_{50}$(nM) HDAC6 = TBD HDAC3 = TBD TABLE 2-continued

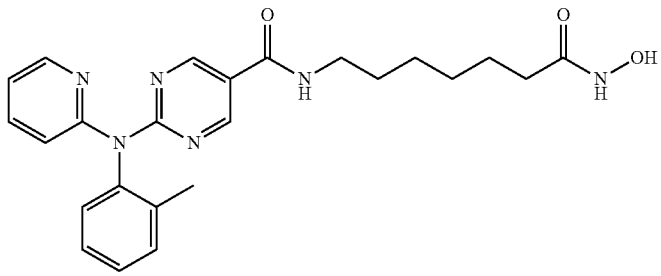

N-(7-(hydroxyamino)-7-oxoheptyl)-2-(pyridin-
2-yl(o-tolyl)amino)pyrimidine-5-carboxamide
IC$_{50}$(nM) HDAC6 = TBD HDAC3 = TBD

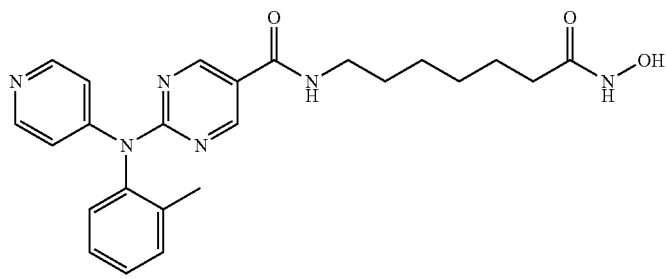

N-(7-(hydroxyamino)-7-oxoheptyl)-2-
(pyridin-4-yl(o-tolyl)amino)pyrimidine-5-
carboxamide
IC$_{50}$(nM) HDAC6 = TBD HDAC3 = TBD

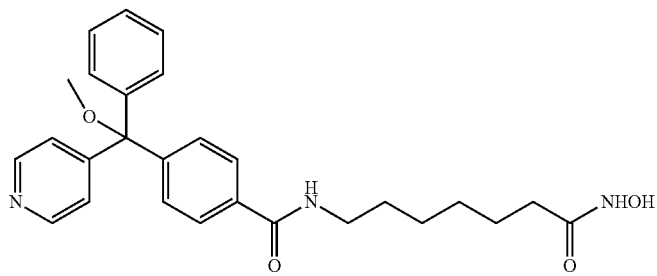

N-(7-(hydroxyamino)-7-oxoheptyl)-4-
(methoxy(phenyl)(pyridin-4-
yl)methyl)benzamide
IC$_{50}$(nM) HDAC6 = 3 HDAC3 = 78

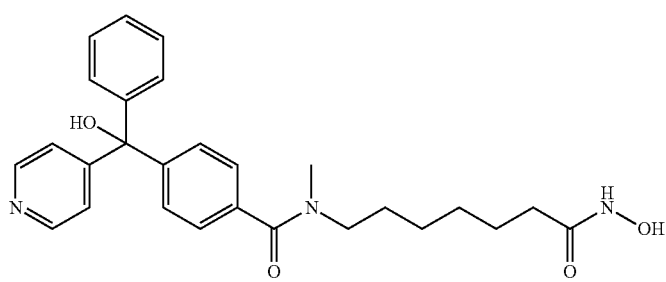

4-(hydroxy(phenyl)(pyridin-4-yl)methyl)-N-
(7-(hydroxyamino)-7-oxoheptyl)-N-
methylbenzamide
IC$_{50}$(nM) HDAC6 = 18 HDAC3 = 221

TABLE 2-continued
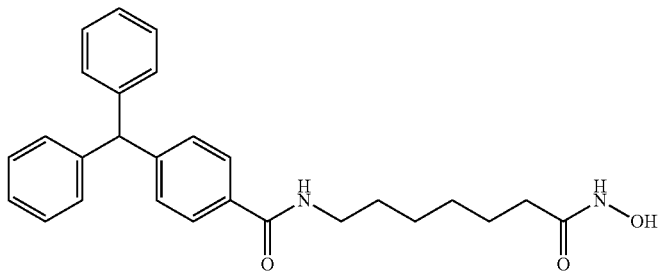
4-benzhydryl-N-(7-(hydroxyamino)-7-
oxoheptyl)benzamide
IC$_{50}$(nM) HDAC6 = 22 HDAC3 = 370
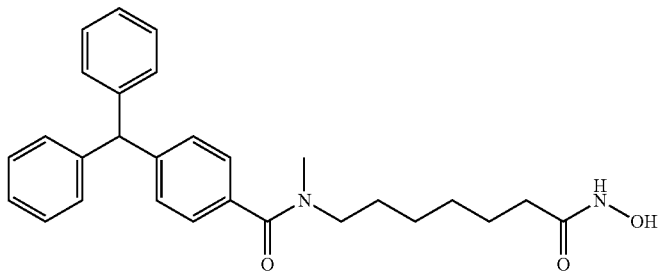
4-benzhydryl-N-(7-(hydroxyamino)-7-
oxoheptyl)-N-methylbenzamide
IC$_{50}$(nM) HDAC6 = 47 HDAC3 = 544
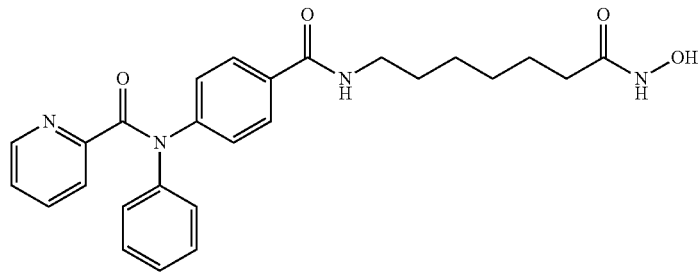
N-(4-(7-(hydroxyamino)-7-oxoheptyl
carbamoyl)phenyl)-N-phenylpicolinamide
IC$_{50}$(nM) HDAC6 = 5 HDAC3 = 68
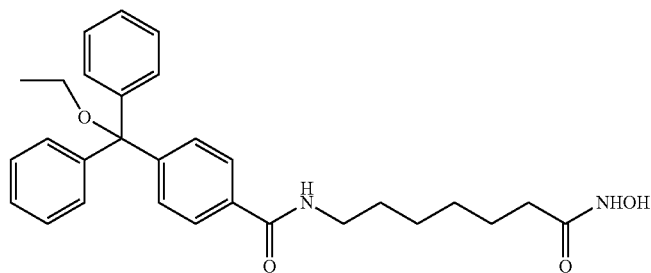
4-(ethoxydiphenylmethyl)-N-(7-
(hydroxyamino)-7-oxoheptyl)benzamide
IC$_{50}$(nM) HDAC6 = 13 HDAC3 = 705

TABLE 2-continued

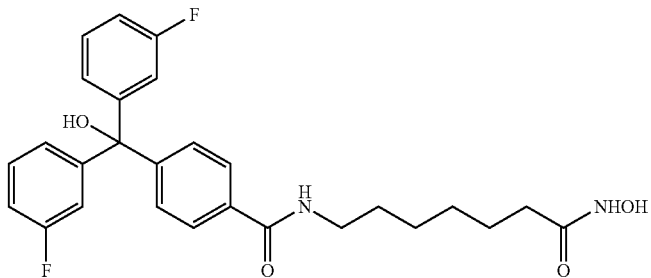

4-(bis(3-fluorophenyl)(hydroxy)methyl)-N-(7-
(hydroxyamino)-7-oxoheptyl)benzamide
IC$_{50}$(nM) HDAC6 = 5 HDAC3 = 186

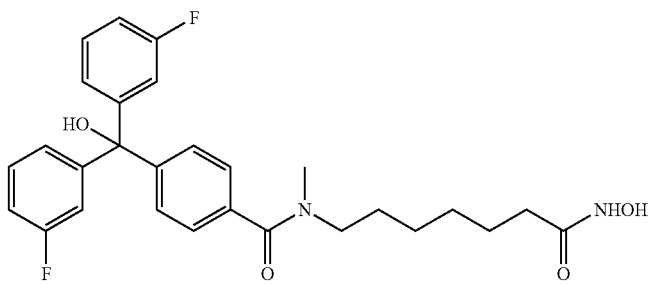

4-(bis(3-fluorophenyl)(hydroxy)methyl)-N-
(7-(hydroxyamino)-7-oxoheptyl)-N-
methylbenzamide
IC$_{50}$(nM) HDAC6 = 10 HDAC3 = 319

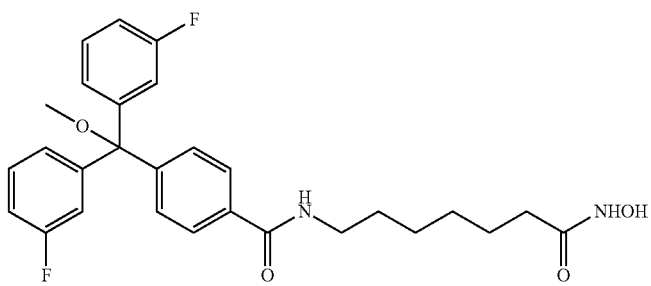

4-(bis(3-fluorophenyl)(methoxy)methyl)-N-(7-
(hydroxyamino)-7-oxoheptyl)benzamide
IC$_{50}$(nM) HDAC6 = 15 HDAC3 = 1261

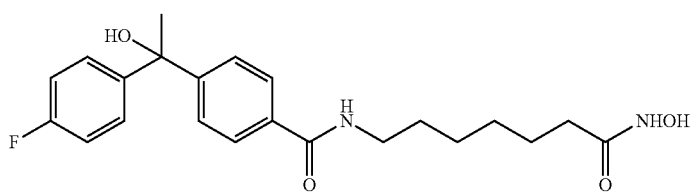

4-(1-(4-fluorophenyl)-1-hydroxyethyl)-N-(7-
(hydroxyamino)-7-oxoheptyl)benzamide
IC$_{50}$(nM) HDAC6 = 3 HDAC3 = 42

TABLE 2-continued
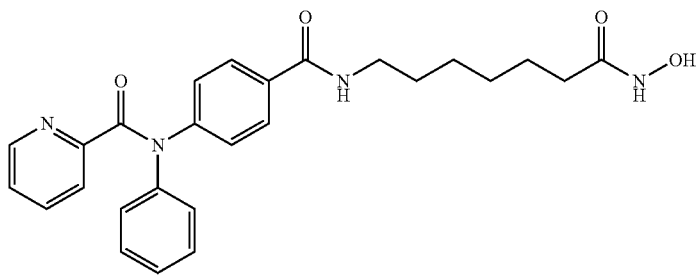
N-(4-(7-(hydroxyamino)-7-oxoheptyl
carbamoyl)phenyl)-N-phenylpicolinamide
IC$_{50}$(nM) HDAC6 = 5 HDAC3 = 68
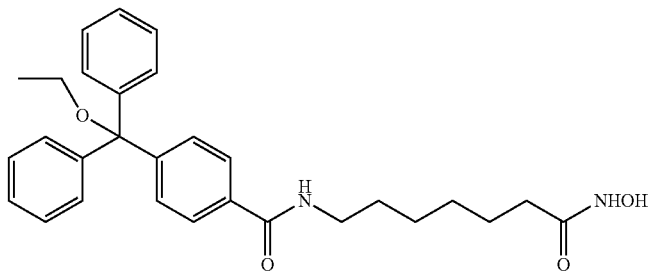
4-(ethoxydiphenylmethyl)-N-(7-
(hydroxyamino)-7-oxoheptyl)benzamide
IC$_{50}$(nM) HDAC6 = 13 HDAC3 = 705
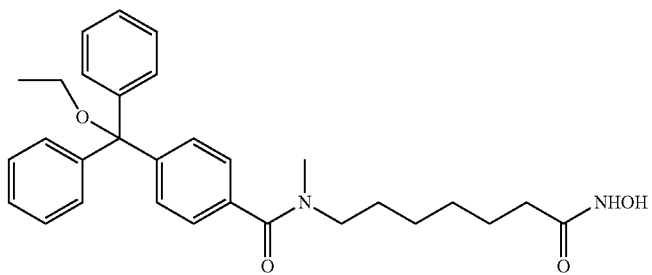
4-(ethoxydiphenylmethyl)-N-(7-(hydroxy-
amino)-7-oxoheptyl)-N-methylbenzamide
IC$_{50}$(nM) HDAC6 = 36 HDAC3 = 899
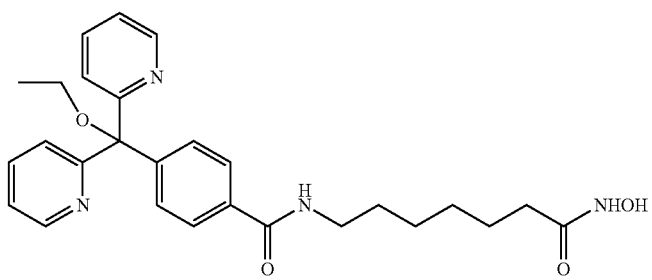
4-(ethoxydipyridin-2-ylmethyl)-N-(7-
(hydroxyamino)-7-oxoheptyl)benzamide
IC$_{50}$(nM) HDAC6 = 6 HDAC3 = 138

TABLE 2-continued

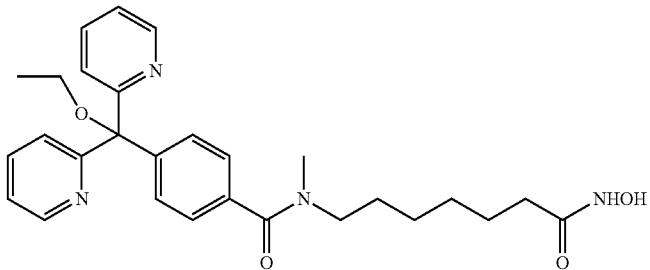

4-(ethoxydipyridin-2-ylmethyl)-N-(7-(hydroxy-
amino)-7-oxoheptyl)-N-methylbenzamide
IC$_{50}$(nM) HDAC6 = 45 HDAC3 = 443

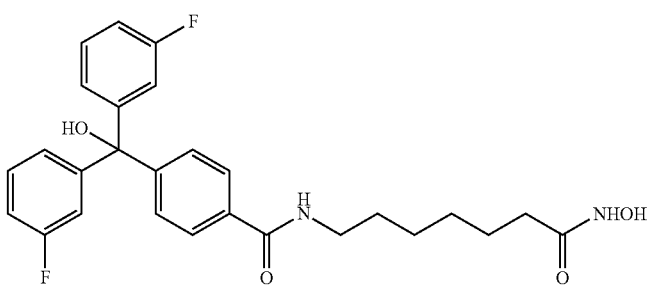

4-(bis(3-fluorophenyl)(hydroxy)methyl)-N-
(7-(hydroxyamino)-7-oxoheptyl)benzamide
IC$_{50}$(nM) HDAC6 = 5 HDAC3 = 186

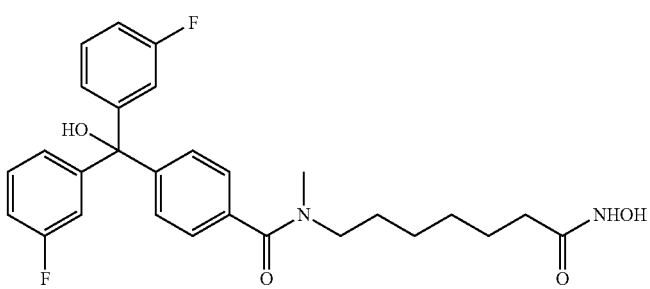

4-(bis(3-fluorophenyl)(hydroxy)methyl)-N-(7-
(hydroxyamino)-7-oxoheptyl)-N-methyl-
benzamide
IC$_{50}$(nM) HDAC6 = 10 HDAC3 = 319

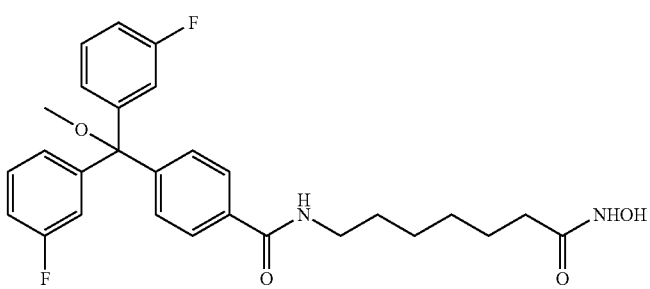

4-(bis(3-fluorophenyl)(methoxy)methyl)-N-
(7-(hydroxyamino)-7-oxoheptyl)benzamide
IC$_{50}$(nM) HDAC6 = 15 HDAC3 = 1281

TABLE 2-continued

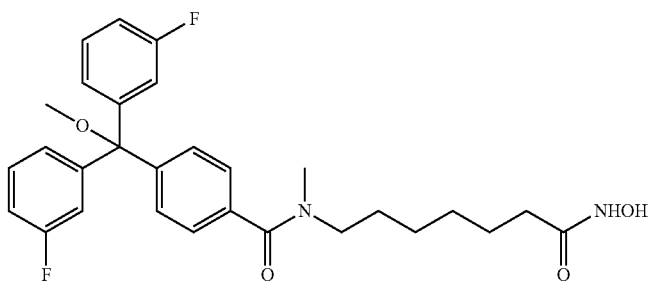

4-(bis(3-fluorophenyl)(methoxy)methyl)-N-(7-
(hydroxyamino)-7-oxoheptyl)-N-methyl-
benzamide
IC$_{50}$(nM) HDAC6 = 47 HDAC3 = 805

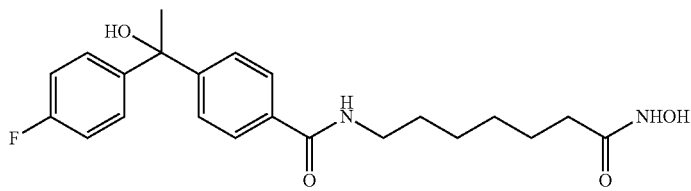

4-(1-(4-fluorophenyl)-1-hydroxyethyl)-N-(7-
(hydroxyamino)-7-oxoheptyl)benzamide
IC$_{50}$(nM) HDAC6 = 3 HDAC3 = 42

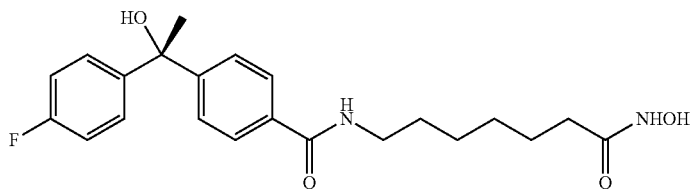

4-(1-(4-fluorophenyl)-1-hydroxyethyl)-N-(7-
(hydroxyamino)-7-oxoheptyl)benzamide
IC$_{50}$(nM) HDAC6 = 3 HDAC3 = 30

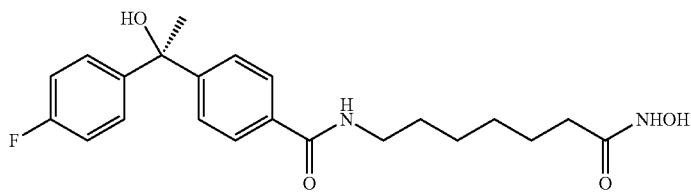

4-(1-(4-fluorophenyl)-1-hydroxyethyl)-N-(7-
(hydroxyamino)-7-oxoheptyl)benzamide
IC$_{50}$(nM) HDAC6 = 3 HDAC3 = 37

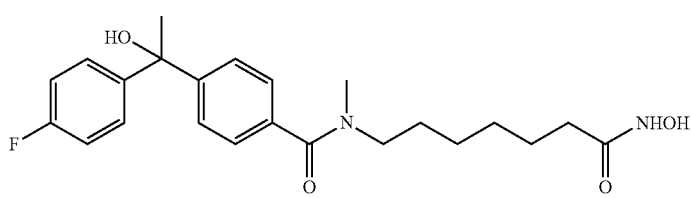

4-(1-(4-fluorophenyl)-1-hydroxyethyl)-N-(7-
(hydroxyamino)-7-oxoheptyl)-N-methyl-
benzamide
IC$_{50}$(nM) HDAC6 = 23 HDAC3 = 243

TABLE 2-continued

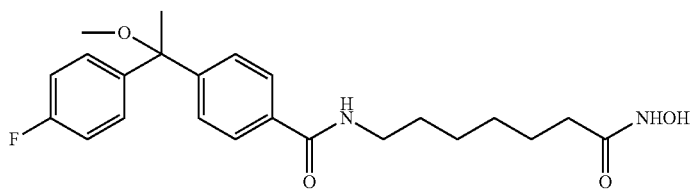

4-(1-(4-fluorophenyl)-1-methoxyethyl)-N-(7-
(hydroxyamino)-7-oxoheptyl)benzamide
IC$_{50}$(nM) HDAC6 = 3 HDAC3 = 28

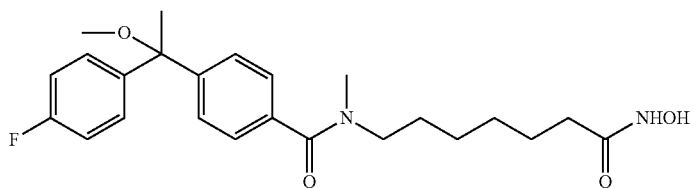

4-(1-(4-fluorophenyl)-1-hydroxyethyl)-N-(7-
(hydroxyamino)-7-oxoheptyl)-N-methyl-
benzamide
IC$_{50}$(nM) HDAC6 = 17 HDAC3 = 187

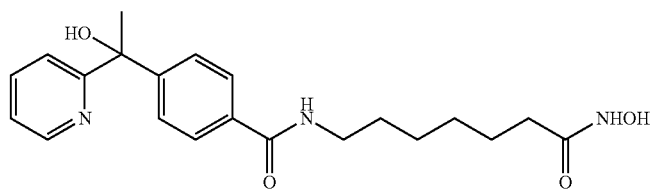

4-(1-hydroxy-1-(pyridin-2-yl)ethyl)-N-(7-
(hydroxyamino)-7-oxoheptyl)benzamide
IC$_{50}$(nM) HDAC6 = 7 HDAC3 = 134

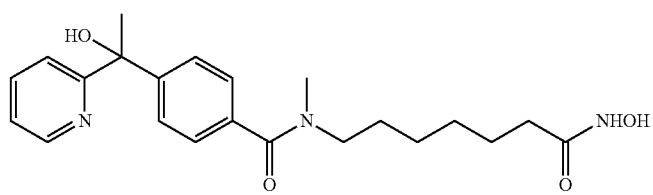

4-(1-hydroxy-1-(pyridin-2-yl)ethyl)-N-(7-
(hydroxyamino)-7-oxoheptyl)-N-methyl-
benzamide
IC$_{50}$(nM) HDAC6 = 36 HDAC3 = 501

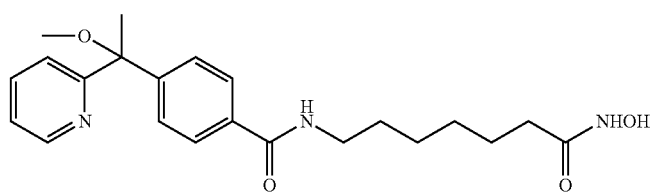

N-(7-(hydroxyamino)-7-oxoheptyl)-4-(1-
methoxy-1-(pyridin-2-yl)ethyl)benzamide
IC$_{50}$(nM) HDAC6 = 4 HDAC3 = 53

TABLE 2-continued

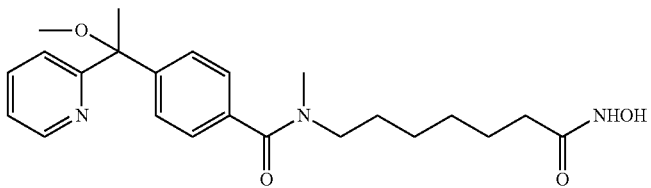

N-(7-(hydroxyamino)-7-oxoheptyl)-4-(1-
methoxy-1-(pyridin-2-yl)ethyl)-N-
methylbenzamide
IC$_{50}$(nM) HDAC6 = 42 HDAC3 = 433

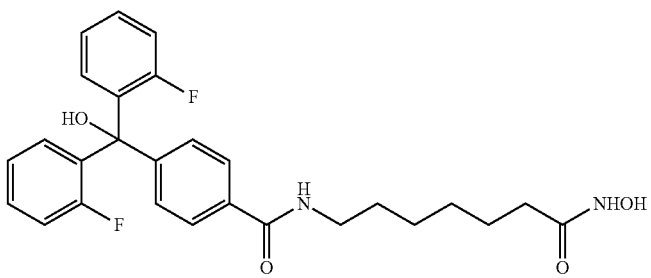

4-(bis(2-fluorophenyl)(hydroxy)methyl)-N-
(7-(hydroxyamino)-7-oxoheptyl)benzamide
IC$_{50}$(nM) HDAC6 = 3 HDAC3 = 74

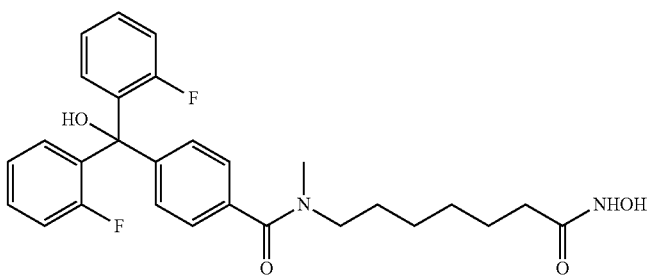

4-(bis(2-fluorophenyl)(hydroxy)methyl)-N-(7-
(hydroxyamino)-7-oxoheptyl)-N-methyl-
benzamide
IC$_{50}$(nM) HDAC6 = 9 HDAC3 = 132

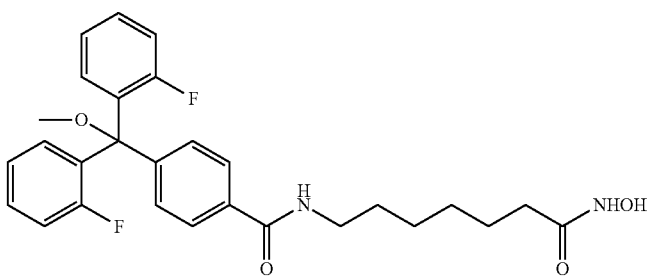

4-(bis(2-fluorophenyl)(methoxy)methyl)-N-
(7-(hydroxyamino)-7-oxoheptyl)benzamide
IC$_{50}$(nM) HDAC6 = 6 HDAC3 = 184

TABLE 2-continued
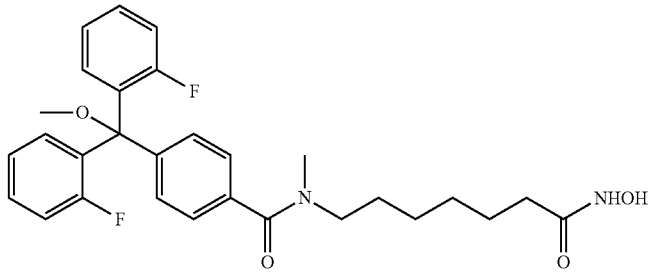
4-(bis(2-fluorophenyl)(methoxy)methyl)-N-(7-(hydroxyamino)-7-oxoheptyl)-N-methyl-benzamide
IC$_{50}$(nM) HDAC6 = 17 HDAC3 = 396
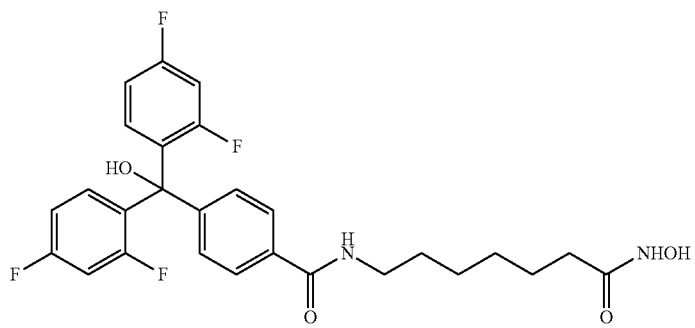
4-(bis(2,4-difluorophenyl)(hydroxy)methyl)-N-(7-(hydroxyamino)-7-oxoheptyl)benzamide
IC$_{50}$(nM) HDAC6 = 5 HDAC3 = 137
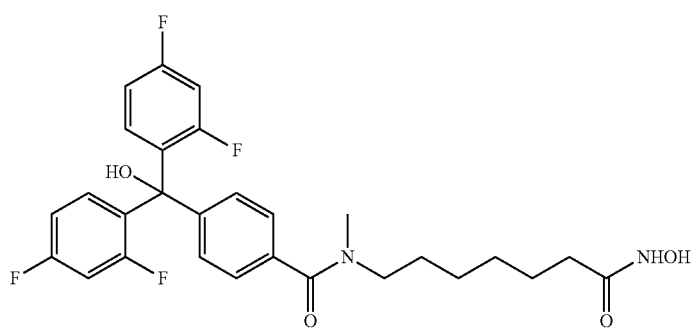
4-(bis(2,4-difluorophenyl)(hydroxy)methyl)-N-(7-(hydroxyamino)-7-oxoheptyl)-N-methylbenzamide
IC$_{50}$(nM) HDAC6 = 13 HDAC3 = 172

TABLE 2-continued

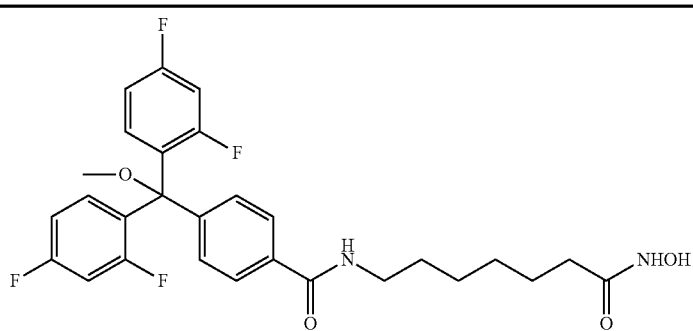

4-(bis(2,4-difluorophenyl)(methoxy)methyl)-
N-(7-(hydroxyamino)-7-oxoheptyl)benzamide
$IC_{50}$(nM) HDAC6 = 20 HDAC3 = 495

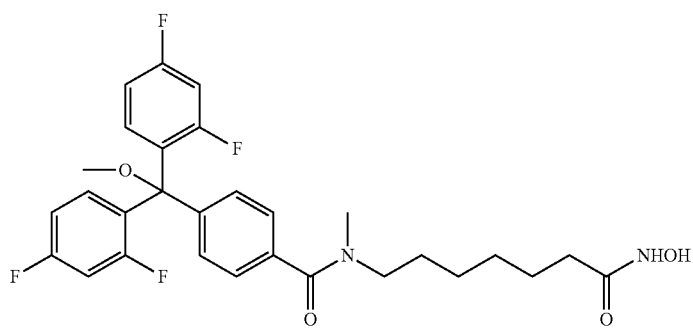

4-(bis(2,4-difluorophenyl)(methoxy)methyl)-N-
(7-(hydroxyamino)-7-oxoheptyl)-N-
methylbenzamide
$IC_{50}$(nM) HDAC6 = 26 HDAC3 = 1335

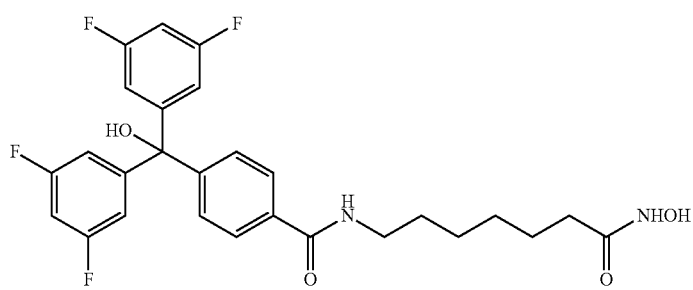

4-(bis(3,5-difluorophenyl)(hydroxy)methyl)-
N-(7-(hydroxyamino)-7-oxoheptyl)benzamide
$IC_{50}$(nM) HDAC6 = 4 HDAC3 = 208

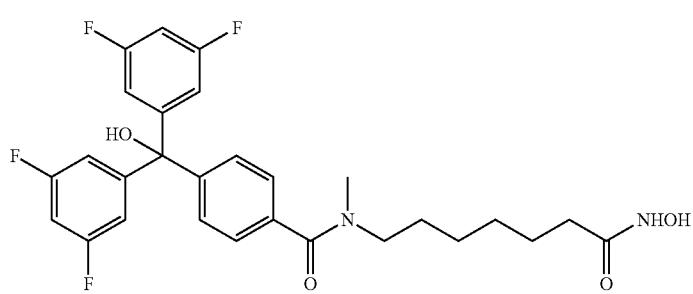

4-(bis(3,5-difluorophenyl)(hydroxy)methyl)-N-
(7-(hydroxyamino)-7-oxoheptyl)-N-
methylbenzamide
$IC_{50}$(nM) HDAC6 = 15 HDAC3 = 186

TABLE 2-continued
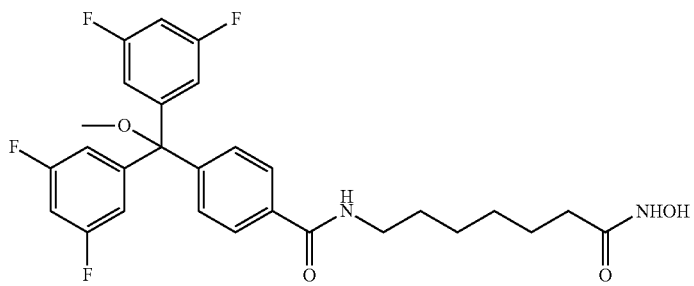
4-(bis(3,5-difluorophenyl)(methoxy)methyl)-
N-(7-(hydroxyamino)-7-oxoheptyl)benzamide
IC$_{50}$(nM) HDAC6 = 20 HDAC3 = 679
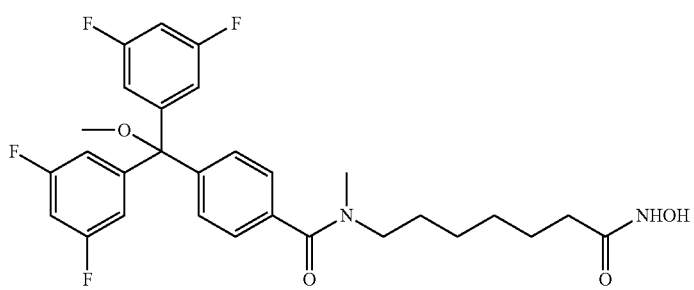
4-(bis(3,5-difluorophenyl)(methoxy)methyl)-N-
(7-(hydroxyamino)-7-oxoheptyl)-N-
methylbenzamide
IC$_{50}$(nM) HDAC6 = 17 HDAC3 = 873
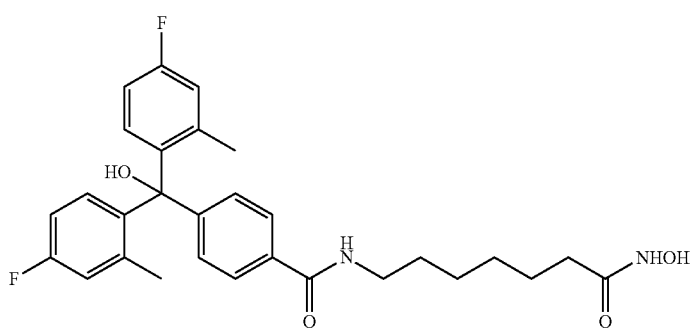
4-(bis(4-fluoro-2-methylphenyl)
(hydroxy)methyl)-N-(7-(hydroxyamino)-7-
oxoheptyl)benzamide
IC$_{50}$(nM) HDAC6 = 59 HDAC3 = 854

TABLE 2-continued

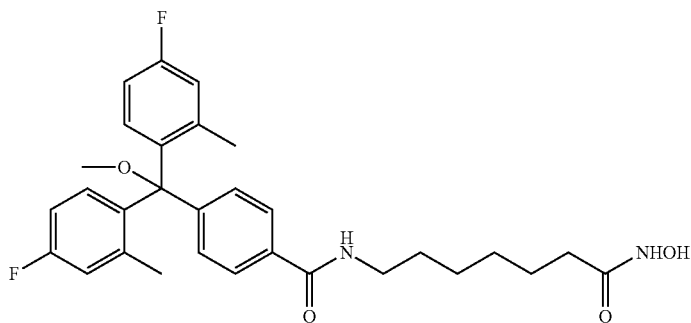

4-(bis(4-fluoro-2-methylphenyl)(methoxy)
methyl)-N-(7-(hydroxyamino)-7-oxoheptyl)
benzamide
IC$_{50}$(nM) HDAC6 = 127 HDAC3 = 2361

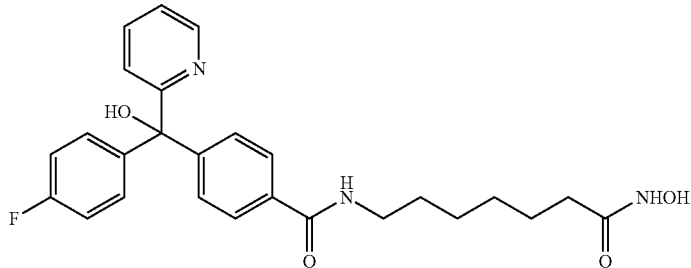

4-((4-fluorophenyl)(hydroxy)(pyridin-2-
yl)methyl-N-(7-(hydroxyamino)-7-
oxoheptyl)benzamide
IC$_{50}$(nM) HDAC6 = 3 HDAC3 = 80

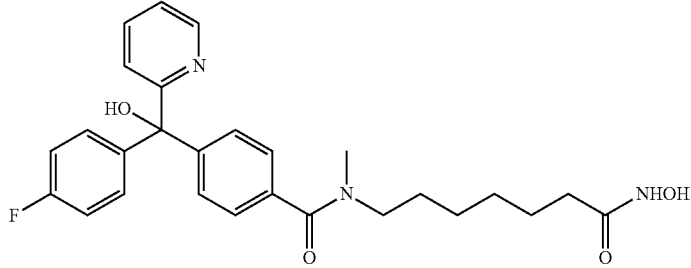

4-((4-fluorophenyl)(hydroxy)(pyridin-2-
yl)methyl-N-(7-(hydroxyamino)-7-oxoheptyl)-
N-methylbenzamide
IC$_{50}$(nM) HDAC6 = 24 HDAC3 = 284

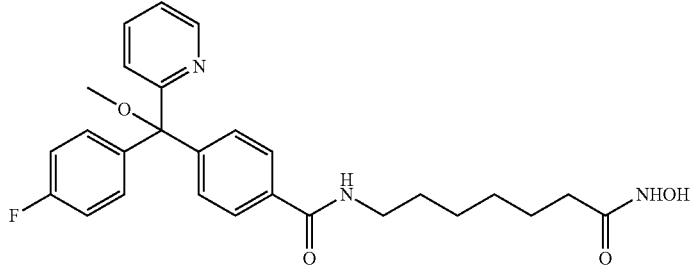

4-((4-fluorophenyl)(methoxy)(pyridin-2-
yl)methyl-N-(7-(hydroxyamino)-7-
oxoheptyl)benzamide
IC$_{50}$(nM) HDAC6 = 3 HDAC3 = 80

TABLE 2-continued

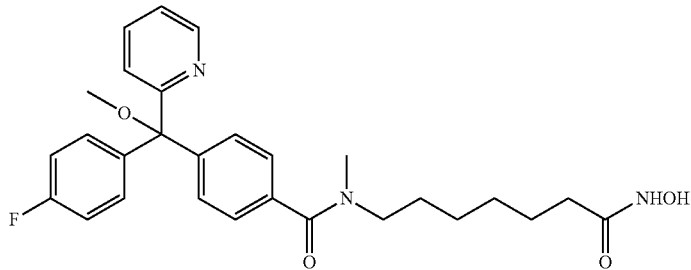

4-((4-fluorophenyl)(methoxy)(pyridin-2-
yl)methyl)-N-(7-(hydroxyamino)-7-oxoheptyl)-
N-methylbenzamide
IC$_{50}$(nM) HDAC6 = 23 HDAC3 = 361

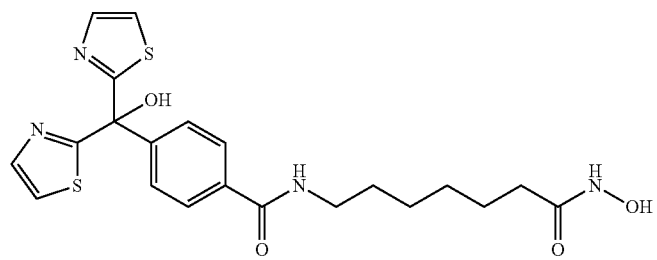

N-(7-(hydroxyamino)-7-oxoheptyl)-4-
(hydroxydithiazol-2-ylmethyl)benzamide
IC$_{50}$(nM) HDAC6 = 5 HDAC3 = 141

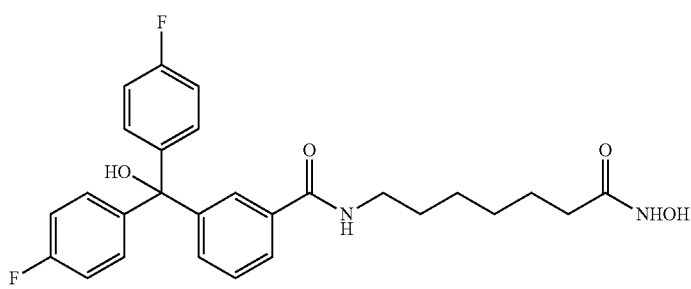

3-(bis(4-fluorophenyl)(hydroxy)methyl)-N-(7-
(hydroxyamino)-7-oxoheptyl)benzamide
IC$_{50}$(nM) HDAC6 = 18 HDAC3 = 63

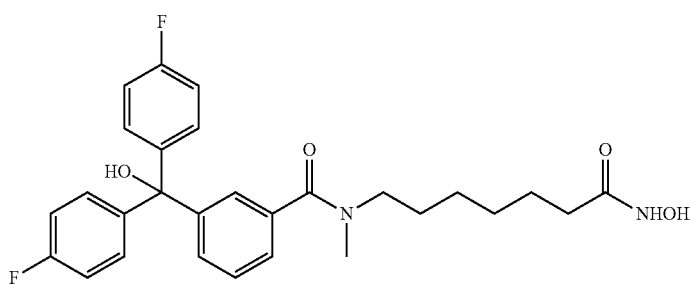

3-(bis(4-fluorophenyl)(hydroxy)methyl)-N-
(7-(hydroxyamino)-7-oxoheptyl)-N-
methylbenzamide
IC$_{50}$(nM) HDAC6 = 72 HDAC3 = 349

TABLE 2-continued

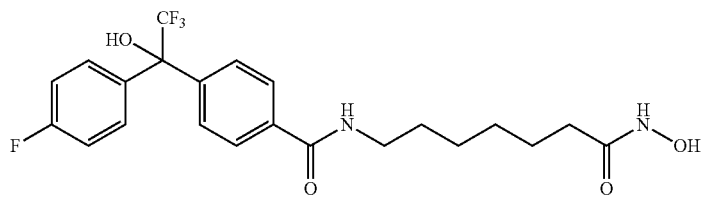

N-(7-(hydroxyamino)-7-oxoheptyl)-4-(2,2,2-
trifluoro-1-(4-fluorophenyl)-1-hydroxyethyl)
benzamide
IC$_{50}$(nM) HDAC6 = 5 HDAC3 = 50

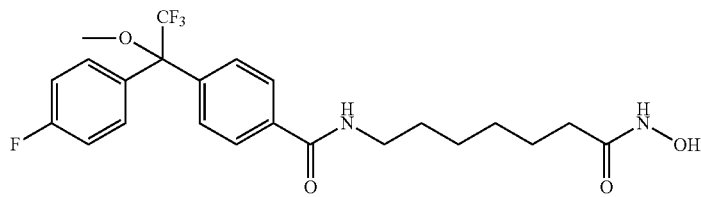

N-(7-(hydroxyamino)-7-oxoheptyl)-4-(2,2,2-
trifluoro-1-(4-fluorophenyl)-1-methoxyethyl)
benzamide
IC$_{50}$(nM) HDAC6 = 10 HDAC3 = 174

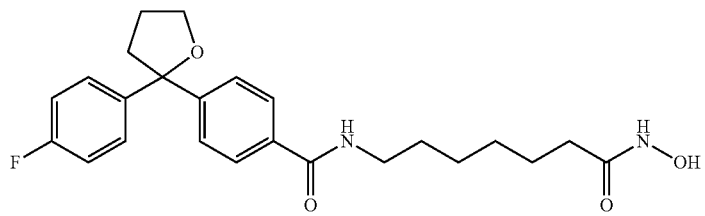

4-(2-(4-fluorophenyl)tetrahydrofuran-2-yl)-N-
(7-(hydroxyamino)-7-oxoheptyl)benzamide
IC$_{50}$(nM) HDAC6 = 3 HDAC3 = 47

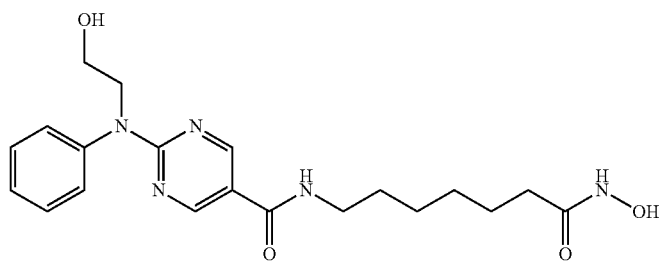

N-(7-(hydroxyamino)-7-oxoheptyl)-2-((2-
hydroxyethyl)(phenyl)amino)pyrimidine-5-
carboxamide
IC$_{50}$(nM) HDAC6 = 8 HDAC3 = 75

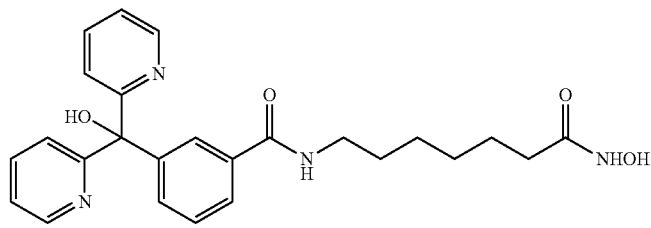

N-(7-(hydroxyamino)-7-oxoheptyl)-3-
(hydroxypyridin-2-ylmethyl)benzamide
IC$_{50}$(nM) HDAC6 = 41 HDAC3 = 285

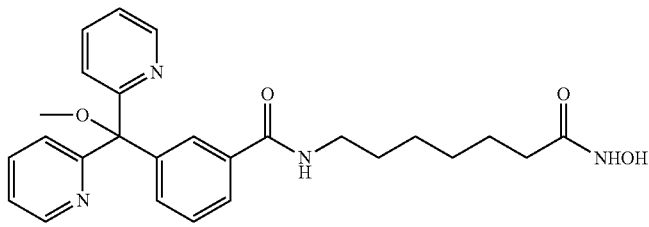

N-(7-(hydroxyamino)-7-oxoheptyl)-3-
(methoxydipyridin-2-ylmethyl)benzamide
IC$_{50}$(nM) HDAC6 = 20 HDAC3 = 217

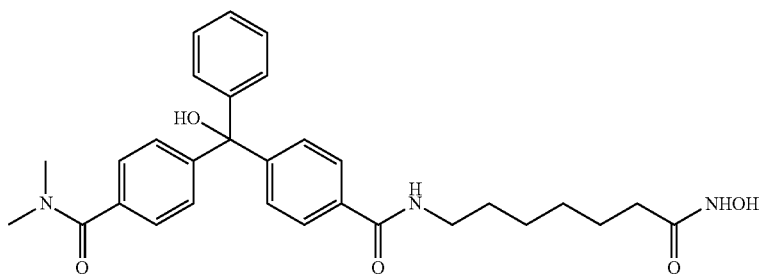

4-(hydroxy(4-(7-(hydroxyamino)-7-
oxoheptylcarbamoyl)phenyl)(phenyl)methyl)-
N,N-dimethylbenzamide
IC$_{50}$(nM) HDAC6 = 4 HDAC3 = 86

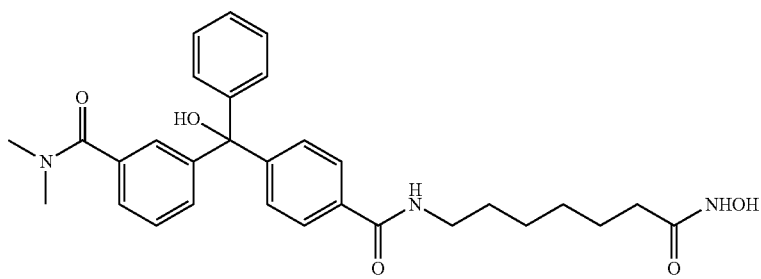

3-(hydroxy(4-(7-(hydroxyamino)-7-
oxoheptylcarbamoyl)phenyl)(phenyl)methyl)-
N,N-dimethylbenzamide
IC$_{50}$(nM) HDAC6 = 3 HDAC3 = 90

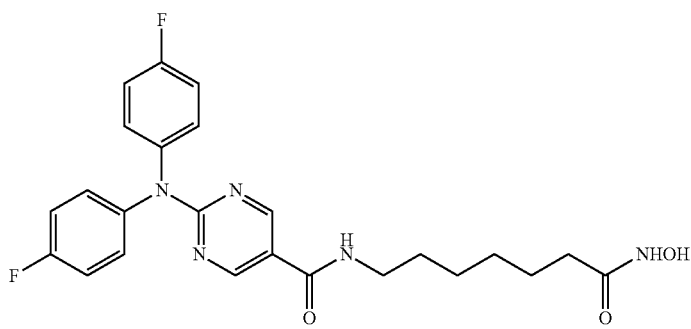

2-(bis(4-fluorophenyl)amino)-N-(7-
(hydroxyamino)-7-oxoheptyl)pyrimidine-5-
carboxamide
IC$_{50}$(nM) HDAC6 = 12 HDAC3 = 124

TABLE 2-continued

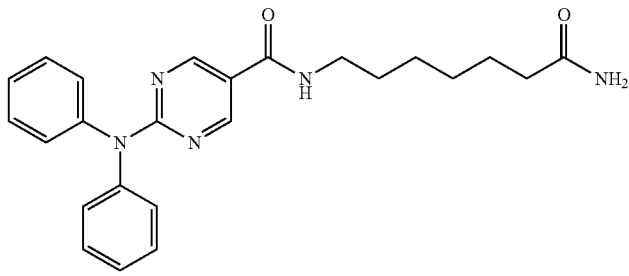

N-(7-amino-7-oxoheptyl)-2-
(diphenylamino)pyrimidine-5-carboxamide
IC$_{50}$(nM) HDAC6 = >50 μM HDAC3 =
>50 μM

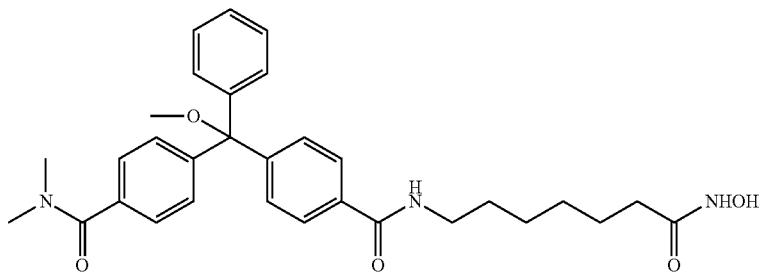

4-((4-(7-(hydroxyamino)-7-
oxoheptylcarbamoyl)phenyl)(methoxy)(phenyl)
methyl)-N,N-dimethylbenzamide
IC$_{50}$(nM) HDAC6 = 4 HDAC3 = 103

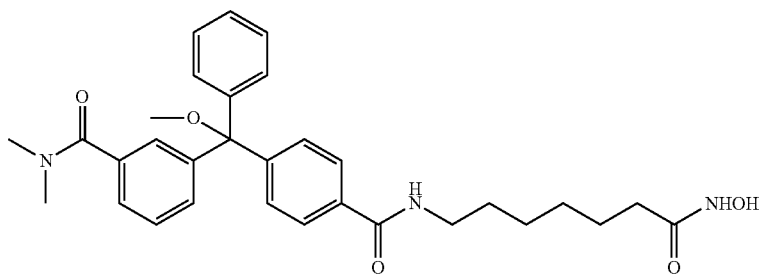

3-((4-(7-(hydroxyamino)-7-
oxoheptylcarbamoyl)phenyl)(methoxy)(phenyl)
methyl)-N,N-dimethylbenzamide
IC$_{50}$(nM) HDAC6 = 3 HDAC3 = 85

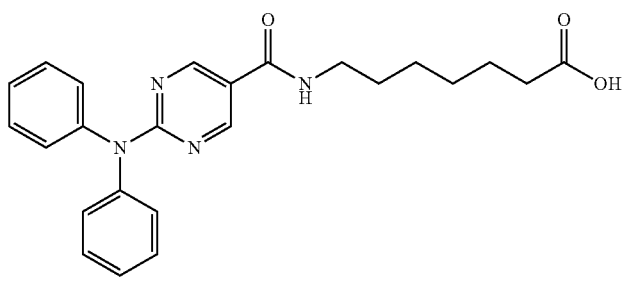

7-(2-(diphenylamino)pyrimidine-5-
carboxamido)heptanoic acid
IC$_{50}$(nM) HDAC6 = 1251 HDAC3 = 19512

TABLE 2-continued

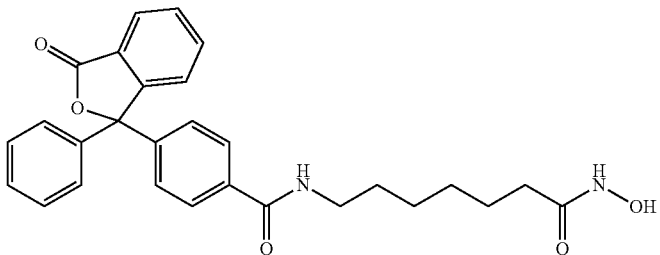

N-(7-(hydroxyamino)-7-oxoheptyl)-4-(3-oxo-1-phenyl-1,3-dihydroisobenzofuran-1-yl)benzamide
IC$_{50}$(nM) HDAC6 = 11 HDAC3 = 153

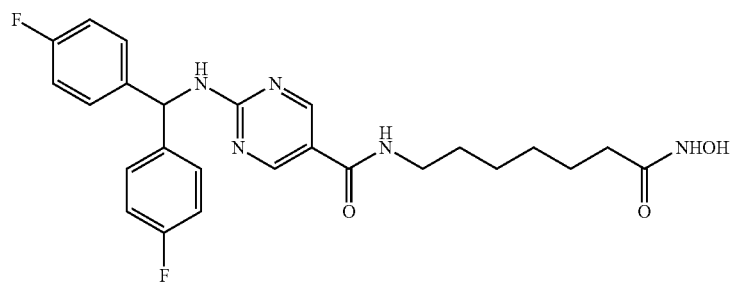

2-(bis(4-fluorophenyl)methylamino)-N-(7-(hydroxyamino)-7-oxoheptyl)pyrimidine-5-carboxamide
IC$_{50}$(nM) HDAC6 = 5 HDAC3 = 65

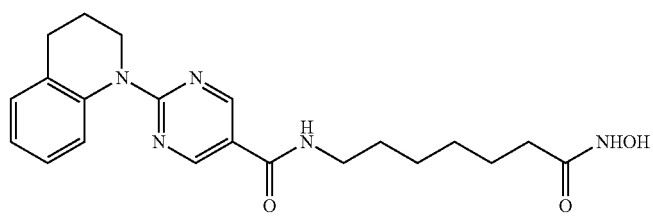

2-(3,4-dihydroquinolin-1(2H)-yl)-N-(7-(hydroxyamino)-7-oxoheptyl)pyrimidine-5-carboxamide
IC$_{50}$(nM) HDAC6 = 6 HDAC3 = 50

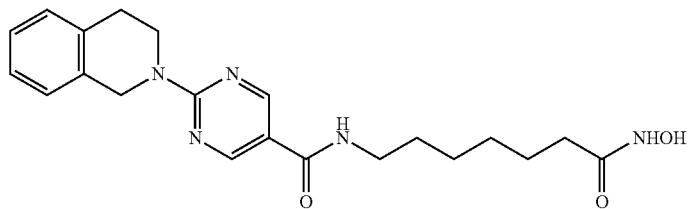

2-(3,4-dihydroisoquinolin-2(1H)-yl)-N-(7-(hydroxyamino)-7-oxoheptyl)pyrimidine-5-carboxamide
IC$_{50}$(nM) HDAC6 = 3 HDAC3 = 53

TABLE 2-continued

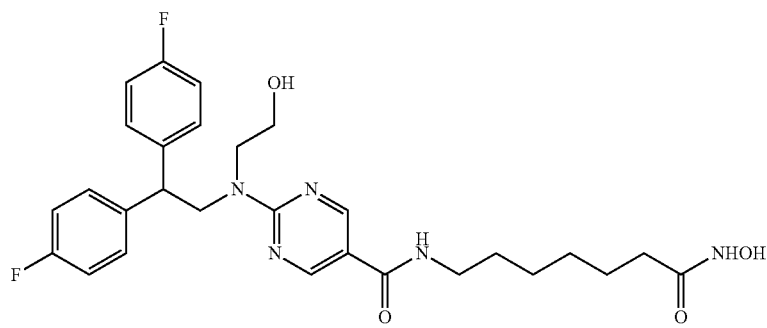

2-((2,2-(bis(4-fluorophenyl)ethyl)(2-
hydroxyethyl)amino)-N-(7-(hydroxyamino)-
7-oxoheptyl)pyrimidine-5-carboxamide
IC$_{50}$(nM) HDAC6 = 8 HDAC3 = 64

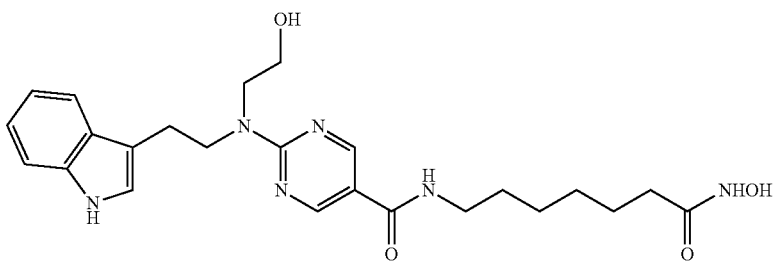

2-((2-(1H-indol-3-yl)ethyl)(2-
hydroxyethyl)amino)-N-(7-(hydroxyamino)-7-
oxoheptyl)pyrimidine-5-carboxamide
IC$_{50}$(nM) HDAC6 = 3 HDAC3 = 35

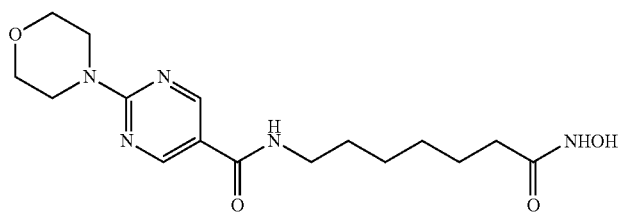

N-(7-(hydroxyamino)-7-oxoheptyl)-2-
morpholinopyrimidine-5-carboxamide
IC$_{50}$(nM) HDAC6 = 8 HDAC3 = 51

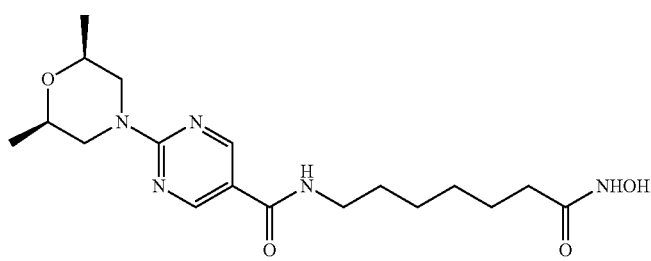

2-((2S,6R)-2,6-dimethylmorpholino)-N-(7-
(hydroxyamino)-7-oxoheptyl)pyrimidine-5-
carboxamide
IC$_{50}$(nM) HDAC6 = 7 HDAC3 = 70

TABLE 2-continued

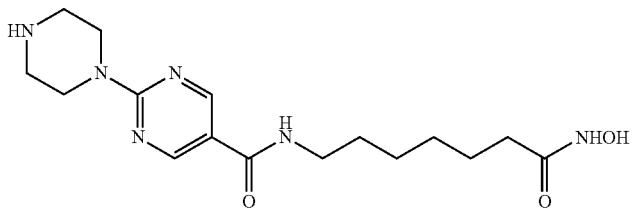

N-(7-(hydroxyamino)-7-oxoheptyl)-2-
(piperazin-1-yl)pyrimidine-5-carboxamide
IC$_{50}$(nM) HDAC6 = 21 HDAC3 = 43

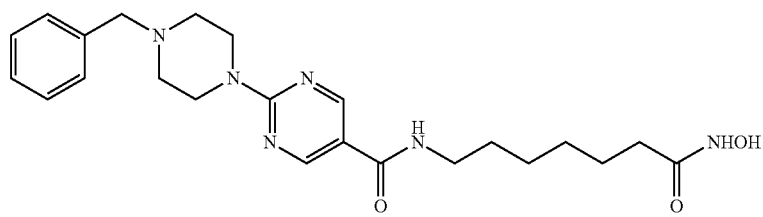

2-(4-benzylpiperazin-1-yl)-N-(7-
(hydroxyamino)-7-oxoheptyl)pyrimidine-5-
carboxamide
IC$_{50}$(nM) HDAC6 = 6 HDAC3 = 100

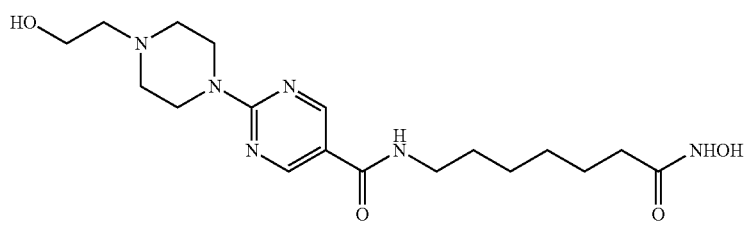

N-(7-(hydroxyamino)-7-oxoheptyl)-2-(4-(2-
hydroxyethyl)piperazin-1-yl)pyrimidine-5-
carboxamide
IC$_{50}$(nM) HDAC6 = 13 HDAC3 = 58

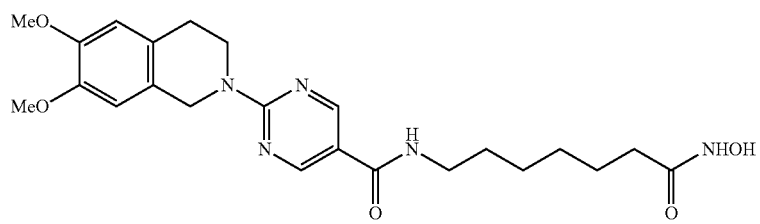

2-(6,7-dimethoxy-3,4-dihydroisoquinolin-
2(1H)-yl)-N-(7-(hydroxyamino)-7-
oxoheptyl)pyrimidine-5-carboxamide
IC$_{50}$(nM) HDAC6 = 2 HDAC3 = 46

TABLE 2-continued

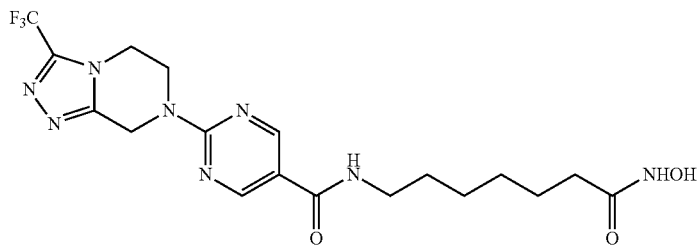

N-(7-(hydroxyamino)-7-oxoheptyl)-2-(3-
(trifluoromethyl)-5,6-dihydro-
[1,2,4]triazolo[4,3-a]pyrazin-7(8H)-
yl)pyrimidine-5-carboxamide
$IC_{50}$(nM) HDAC6 = 14 HDAC3 = 149

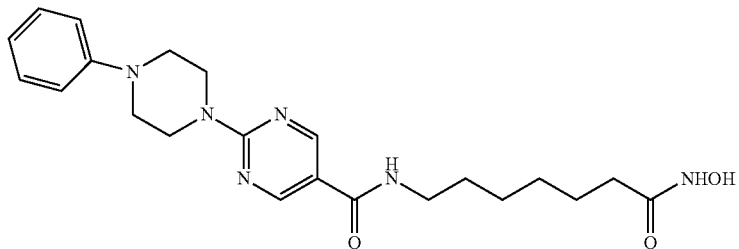

N-(7-(hydroxyamino)-7-oxoheptyl)-2-(4-
phenylpiperazin-1-yl)pyrimidine-5-carboxamide
$IC_{50}$(nM) HDAC6 = 4 HDAC3 = 57

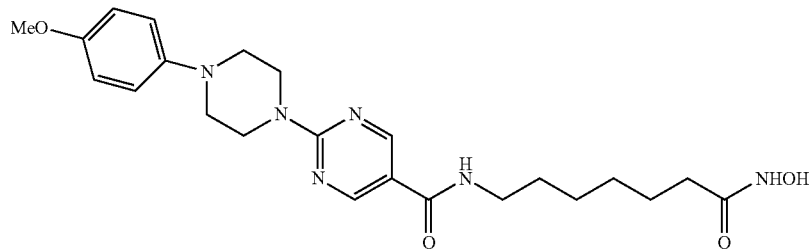

N-(7-(hydroxyamino)-7-oxoheptyl)-2-(4-(4-
methoxyphenyl)piperazin-1-yl)pyrimidine-5-
carboxamide
$IC_{50}$(nM) HDAC6 = 4 HDAC3 = 58

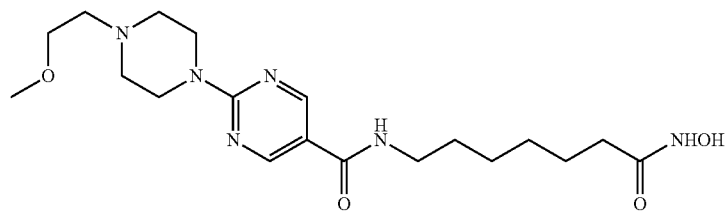

N-(7-(hydroxyamino)-7-oxoheptyl)-2-(4-(2-
methoxyethyl)piperazin-1-yl)pyrimidine-5-
carboxamide
$IC_{50}$(nM) HDAC6 = 13 HDAC3 = 133

TABLE 2-continued

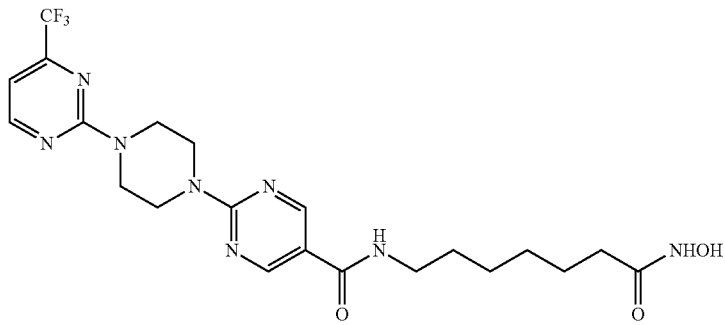

N-(7-(hydroxyamino)-7-oxoheptyl)-2-(4-(4-
(trifluoromethyl)pyrimidin-2-yl)piperazin-1-
yl)pyrimidine-5-carboxamide
IC$_{50}$(nM) HDAC6 = 7 HDAC3 = 54

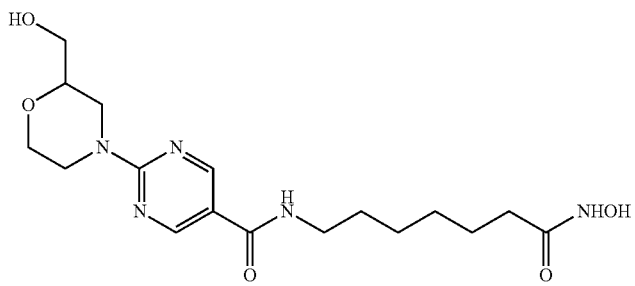

N-(7-(hydroxyamino)-7-oxoheptyl)-2-(2-
(hydroxymethyl)morpholino)pyrimidine-5-
carboxamide
IC$_{50}$(nM) HDAC6 = 7 HDAC3 = 34

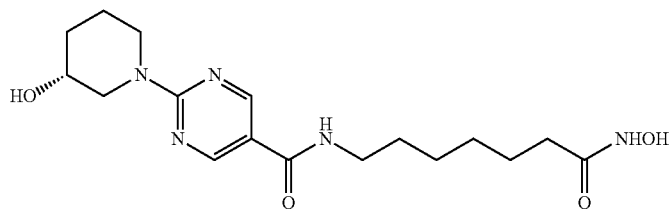

(R)-N-(7-(hydroxyamino)-7-oxoheptyl)-2-(3-
hydroxypiperidin-1-yl)pyrimidine-5-
carboxamide
IC$_{50}$(nM) HDAC6 = 7 HDAC3 = 49

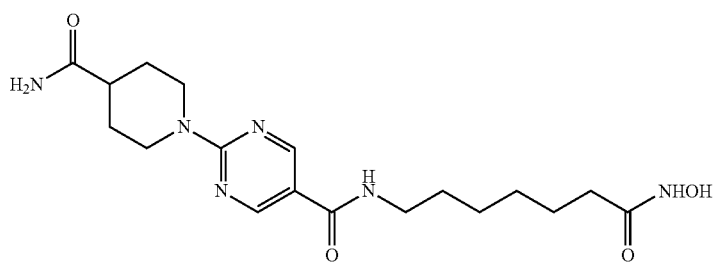

2-(4-carbamoylpiperidin-1-yl)-N-(7-
(hydroxyamino)-7-oxoheptyl)pyrimidine-5-
carboxamide
IC$_{50}$(nM) HDAC6 = 8 HDAC3 = 41

TABLE 2-continued

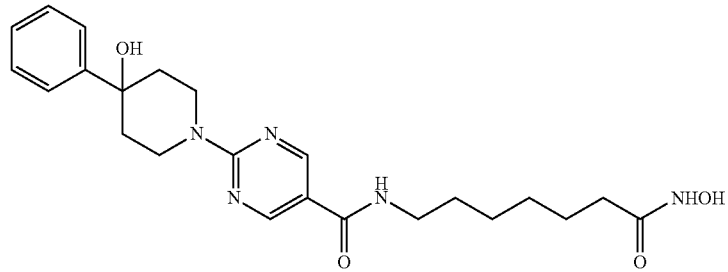

2-(4-hydroxy-4-phenylpiperidin-1-yl)-N-(7-
(hydroxyamino)-7-oxoheptyl)pyrimidine-5-
carboxamide
IC$_{50}$(nM) HDAC6 = 4 HDAC3 = 39

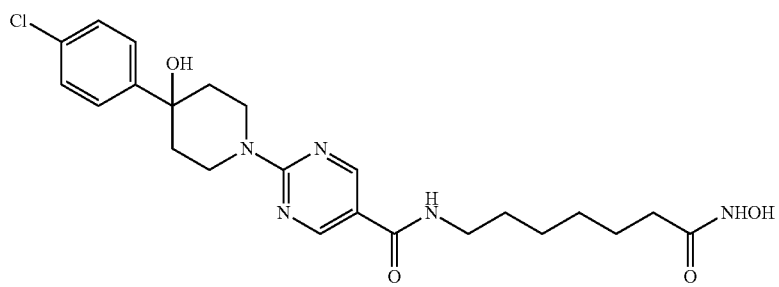

2-(4-(4-chlorophenyl)-4-hydroxypiperidin-1-
yl)-N-(7-(hydroxyamino)-7-
oxoheptyl)pyrimidine-5-carboxamide
IC$_{50}$(nM) HDAC6 = 4 HDAC3 = 53

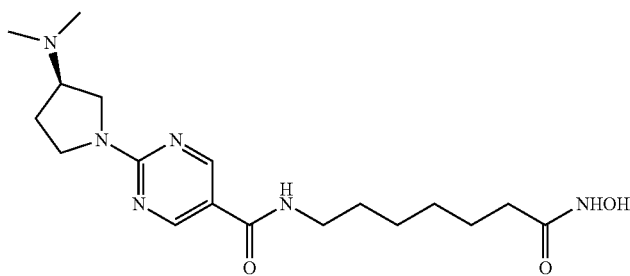

(R)-2-(3-(dimethylamino)pyrrolidin-1-yl)-N-
(7-(hydroxyamino)-7-oxoheptyl)pyrimidine-
5-carboxamide
IC$_{50}$(nM) HDAC6 = 33 HDAC3 = 80

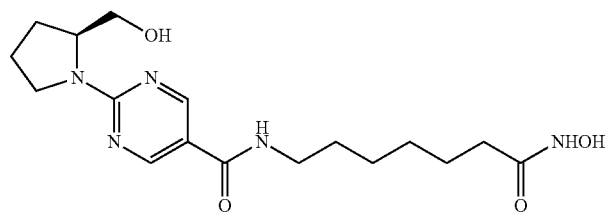

(S)-N-(7-(hydroxyamino)-7-oxoheptyl)-2-(2-
(hydroxymethyl)pyrrolidin-1-yl)pyrimidine-5-
carboxamide
IC$_{50}$(nM) HDAC6 = 7 HDAC3 = 30

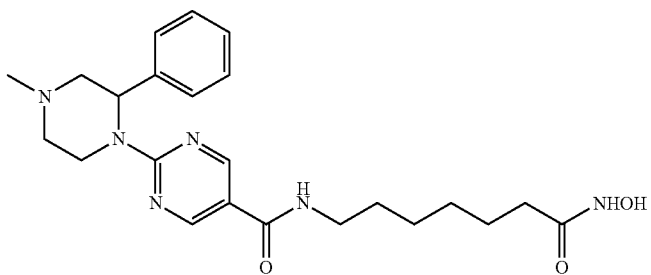

N-(7-(hydroxyamino)-7-oxoheptyl)-2-(4-methyl-2-phenylpiperazin-1-yl)pyrimidine-5-carboxamide
IC$_{50}$(nM) HDAC6 = 5 HDAC3 = 51

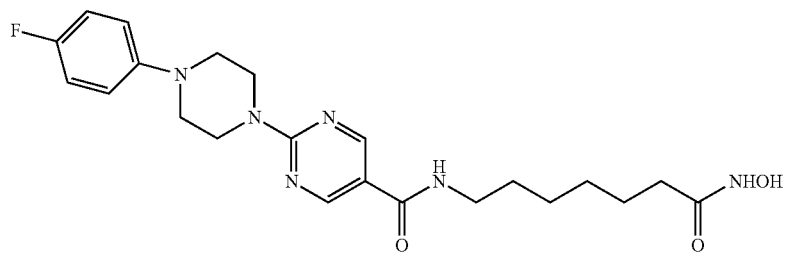

2-(4-(4-fluorophenyl)piperazin-1-yl)-N-(7-(hydroxyamino)-7-oxoheptyl)pyrimidine-5-carboxamide
IC$_{50}$(nM) HDAC6 = 5 HDAC3 = 52

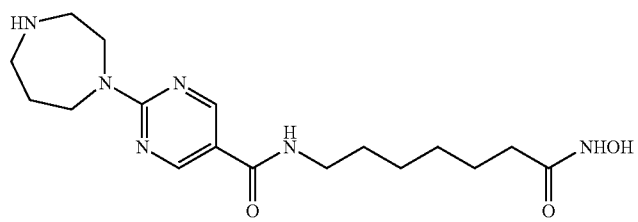

2-(1,4-diazepan-1-yl)-N-(7-(hydroxyamino)-7-oxoheptyl)pyrimidine-5-carboxamide
IC$_{50}$(nM) HDAC6 = 19 HDAC3 = 34

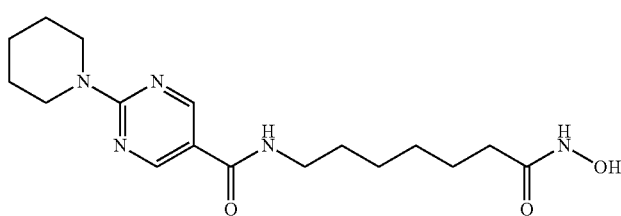

N-(7-(hydroxyamino)-7-oxoheptyl)-2-(piperidin-1-yl)pyrimidine-5-carboxamide
IC$_{50}$(nM) HDAC6 = 5 HDAC3 = 23

TABLE 2-continued

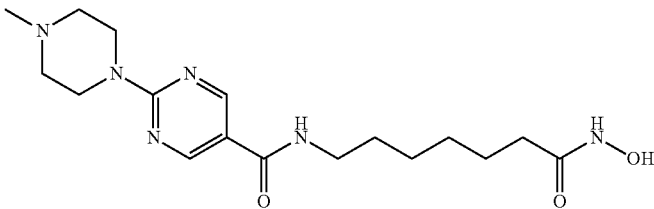

N-(7-(hydroxyamino)-7-oxoheptyl)-2-(4-
methylpiperazin-1-yl)pyrimidine-5-
carboxamide
IC$_{50}$(nM) HDAC6 = 18 HDAC3 = 87

The term "alkyl," as used herein, refers to saturated, straight- or branched-chain hydrocarbon moieties containing, in certain embodiments, between one and six, or one and eight carbon atoms, respectively. Examples of C$_1$-C$_6$ alkyl moieties include, but are not limited to, methyl, ethyl, propyl, isopropyl, n-butyl, tert-butyl, neopentyl, n-hexyl moieties; and examples of C$_1$-C$_8$ alkyl moieties include, but are not limited to, methyl, ethyl, propyl, isopropyl, n-butyl, tert-butyl, neopentyl, n-hexyl, heptyl, and octyl moieties.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl moiety.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like.

The term "aralkyl," or "arylalkyl," as used herein, refers to an alkyl residue attached to an aryl ring. Examples include, but are not limited to, benzyl, phenethyl and the like.

The term "carbocyclic," as used herein, denotes a monovalent group derived from a monocyclic or polycyclic saturated, partially unsaturated, or fully unsaturated carbocyclic ring compound. Examples of carbocyclic groups include groups found in the cycloalkyl definition and aryl definition.

The term "cycloalkyl," as used herein, denotes a monovalent group derived from a monocyclic or polycyclic saturated or partially unsaturated carbocyclic ring compound. Examples of C$_3$-C$_8$-cycloalkyl include, but not limited to, cyclopropyl, cyclobutyl, cyclopentyl, cyclohexyl, cyclopentyl and cyclooctyl; and examples of C$_3$-C$_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, moieties or ring system having at least one aromatic ring, having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH(C$_1$-C$_{12}$ alkyl) where C$_1$-C$_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the invention, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

The term "oxo" as used herein, refers to an oxygen atom that is attached to a carbon, preferably by a double bond (e.g., carbonyl).

These compounds can optionally be substituted with one or more substituents, such as are illustrated generally above, or as exemplified by particular classes, subclasses, and species described herein. It will be appreciated that the phrase "optionally substituted" is used interchangeably with the phrase "substituted or unsubstituted." In general, the term "substituted," whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted," "optionally substituted alkyl," "optionally substituted "optionally substituted alkenyl," "optionally substituted alkynyl," "optionally substituted cycloalkyl," "optionally substituted cycloalkenyl," "optionally substituted aryl," "optionally substituted heteroaryl," "optionally substituted aralkyl," "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

alkyl, alkenyl, alkynyl, cycloalkyl, aryl, heterocycloalkyl, heteroaryl, arylalkyl, heteroarylalkyl, —F, —Cl, —Br, —I, —OH, protected hydroxy, oxygen, oxo,

—NO$_2$, —CN,

—NH$_2$, protected amino, —NH—C$_1$-C$_{12}$-alkyl, —NH-aryl, -dialkylamino, —O—C$_1$-C$_{12}$-alkyl, —O-aryl,

—C(O)—, —C(O)O—, —C(O)NH—, —OC(O)—, —OC(O)O—, —OC(O)NH—, —NHC(O)—, —NHC(O)O—,

—C(O)—C$_1$-C$_{12}$-alkyl, —C(O)—C$_3$-C$_{12}$-cycloalkyl, —C(O)-aryl, —C(O)-heteroaryl, —C(O)-heterocycloalkyl, —C(O)O—C$_1$-C$_{12}$-alkyl, —C(O)O—C$_3$-C$_{12}$-cycloalkyl, —C(O)O-aryl, —C(O)O-heteroaryl, —C(O)O-heterocycloalkyl, —CONH$_2$, —CONH—C$_1$-C$_{12}$-alkyl, —CONH-aryl, —OCO$_2$—C$_1$-C$_{12}$-alkyl, —OCO$_2$-aryl, —OCONH$_2$, —OCONH—C$_1$-C$_{12}$-alkyl, —OCONH-aryl, —NHC(O)—C$_1$-C$_{12}$-alkyl, —NHC(O)-aryl, —NHCO$_2$—C$_1$-C$_{12}$-alkyl, —NHCO$_2$-aryl, —S(O)—C$_1$-C$_{12}$-alkyl, —S(O)-aryl, —SO$_2$NH—C$_1$-C$_{12}$-alkyl, —SO$_2$NH-aryl, —NHSO$_2$—C$_1$-C$_{12}$-alkyl, —NHSO$_2$-aryl, —SH, —S—C$_1$-C$_{12}$-alkyl, or —S-aryl.

In certain embodiments, the optionally substituted groups include the following: C$_1$-C$_{12}$-alkyl, C$_2$-C$_{12}$-alkenyl, C$_2$-C$_{12}$-alkynyl, C$_3$-C$_{12}$-cycloalkyl, C$_3$-C$_{12}$-aryl, C$_3$-C$_{12}$-heterocycloalkyl, C$_3$-C$_{12}$-heteroaryl, C$_4$-C$_{12}$-arylalkyl, or C$_2$-C$_{12}$-heteroarylalkyl.

It is understood that the aryls, heteroaryls, alkyls, and the like can be further substituted.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds described herein, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydro iodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug," as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating disorders through administering, pharmaceutically acceptable prodrugs of compounds described herein. For example, compounds described herein having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds described herein. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

In certain embodiments, the compound used in the methods provided herein is 2-(diphenylamino)-N-(7-(hydroxyamino)-7-oxoheptyl)pyrimidine-5-carboxamide (Compound A):

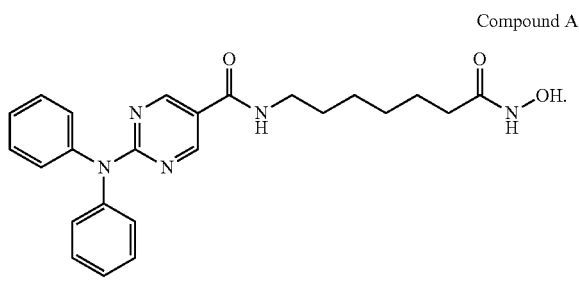 [SMILES: O=C(CCCCCCNC(=O)c1cnc(N(c2ccccc2)c2ccccc2)nc1)NO]

Compound A

In a certain embodiment, the compound used in the methods provided herein is N-(7-(hydroxyamino)-7-oxoheptyl)-2-(phenyl(o-tolyl)amino)pyrimidine-5-carboxamide (Compound B):

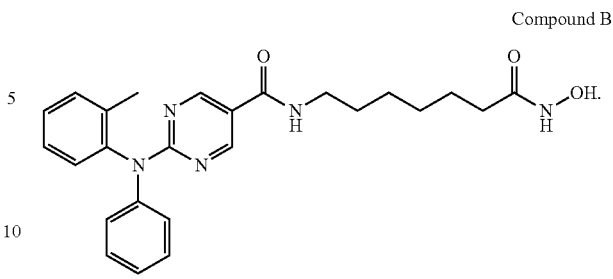

Compound B

In another certain embodiment, the compound used in the methods provided herein is 2-(2-chlorophenyl)(phenyl)amino)-N-(7-(hydroxyamino)-7-oxoheptyl)pyrimidine-5-carboxamide (Compound C):

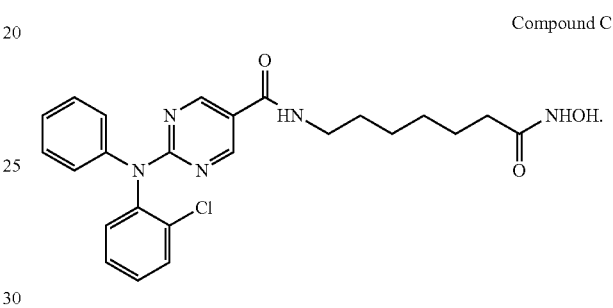

Compound C

Thus, in one embodiment, provided herein are methods of treating osteoporosis in a subject in need thereof. These methods include administering to the subject a therapeutically effective amount of a compound of formula I. In another embodiment, provided herein are methods of treating Paget's Disease in a subject in need thereof. These methods include administering to the subject a therapeutically effective amount of a compound of formula I. In still another embodiment, provided herein is a method of treating metastatic bone disease (MBD) in a subject in need thereof, comprising administering to the subject a therapeutically effective amount of a compound of formula I. In yet another embodiment, provided herein are methods of treating osteolytic bone lesions in a subject in need thereof, comprising administering to the subject a therapeutically effective amount of a compound of formula I. In another embodiment, provided herein are methods of treating osteolytic bone lesions associated with MM in a subject in need thereof, comprising administering to the subject a therapeutically effective amount of a compound of formula I. In still another embodiment, provided herein are methods of treating osteogenesis imperfecta (OI) in a subject in need thereof, comprising administering to the subject a therapeutically effective amount of a compound of formula I. In still another embodiment, provided herein are methods of treating osteopenia in a subject in need thereof, comprising administering to the subject a therapeutically effective amount of a compound of formula I.

In another embodiment, this disclosure provides methods of treating osteoporosis in a subject in need thereof, comprising administering to the subject a therapeutically effective amount of a compound of formula IV. In another embodiment, provided herein are methods of treating Paget's Disease in a subject in need thereof, comprising administering to the subject a therapeutically effective amount of a compound of formula IV. In still another embodiment, provided herein are methods of treating Metastatic bone disease (MBD) in a subject in need thereof, comprising administering to the subject a therapeutically effective amount of a compound of formula IV. In yet another embodiment, provided herein are methods of treating osteolytic bone lesions in a subject in need thereof, comprising administering to the subject a therapeutically effective amount of a compound of formula IV. In another embodiment, provided herein are methods of treating osteolytic bone lesions associated with MM in a subject in need thereof, comprising administering to the subject a therapeutically effective amount of a compound of formula IV. In still another embodiment, provided herein are methods of treating osteogenesis imperfecta (OI) in a subject in need thereof, comprising administering to the subject a therapeutically effective amount of a compound of formula IV. In still another embodiment, provided herein methods of treating osteopenia in a subject in need thereof, comprising administering to the subject a therapeutically effective amount of a compound of formula IV.

In another embodiment, this disclosure provides methods of treating osteoporosis in a subject in need thereof, comprising administering to the subject a therapeutically effective amount of a compound of formula IVa. In another embodiment, provided herein is a method of treating Paget's Disease in a subject in need thereof, comprising administering to the subject a therapeutically effective amount of a compound of formula IVa. In still another embodiment, provided herein is a method of treating Metastatic bone disease (MBD) in a subject in need thereof, comprising administering to the subject a therapeutically effective amount of a compound of formula IVa. In yet another embodiment, provided herein is a method of treating osteolytic bone lesions in a subject in need thereof, comprising administering to the subject a therapeutically effective amount of a compound of formula IVa. In another embodiment, provided herein is a method of treating osteolytic bone lesions associated with MM in a subject in need thereof, comprising administering to the subject a therapeutically effective amount of a compound of formula IVa. In still another embodiment, provided herein is a method of treating osteogenesis imperfecta (OI) in a subject in need thereof, comprising administering to the subject a therapeutically effective amount of a compound of formula IVa. In still another embodiment, provided herein is a method of treating osteopenia in a subject in need thereof, comprising administering to the subject a therapeutically effective amount of a compound of formula IVa.

In another embodiment, this disclosure provides methods of treating osteoporosis in a subject in need thereof, comprising administering to the subject a therapeutically effective amount of Compound A. In another embodiment, provided herein are methods of treating Paget's Disease in a subject in need thereof, comprising administering to the subject a therapeutically effective amount of Compound A. In still another embodiment, provided herein are methods of treating Metastatic bone disease (MBD) in a subject in need thereof, comprising administering to the subject a therapeutically effective amount of Compound A. In yet another embodiment, provided herein are methods of treating osteolytic bone lesions in a subject in need thereof, comprising administering to the subject a therapeutically effective amount of Compound A. In another embodiment, provided herein are methods of treating osteolytic bone lesions associated with MM in a subject in need thereof, comprising administering to the subject a therapeutically effective amount of Compound A. In still another embodiment, provided herein are methods of treating osteogenesis imperfecta (OI) in a subject in need thereof, comprising administering to the subject a therapeutically effective amount of Compound A. In still another embodiment, provided herein are methods of treating osteopenia in a subject in need thereof, comprising administering to the subject a therapeutically effective amount of Compound A.

In another embodiment, this disclosure provides methods of treating osteoporosis in a subject in need thereof, comprising administering to the subject a therapeutically effective amount of Compound B. In another embodiment, provided herein is a method of treating Paget's Disease in a subject in need thereof, comprising administering to the subject a therapeutically effective amount of Compound B. In still another embodiment, provided herein is a method of treating Metastatic bone disease (MBD) in a subject in need thereof, comprising administering to the subject a therapeutically effective amount of Compound B. In yet another embodiment, provided herein is a method of treating osteolytic bone lesions in a subject in need thereof, comprising administering to the subject a therapeutically effective amount of Compound B. In another embodiment, provided herein is a method of treating osteolytic bone lesions associated with MM in a subject in need thereof, comprising administering to the subject a therapeutically effective amount of Compound B. In still another embodiment, provided herein is a method of treating osteogenesis imperfecta (OI) in a subject in need thereof, comprising administering to the subject a therapeutically effective amount of Compound B. In still another embodiment, provided herein is a method of treating osteopenia in a subject in need thereof, comprising administering to the subject a therapeutically effective amount of Compound B.

In another embodiment, this disclosure provides methods of treating osteoporosis in a subject in need thereof, comprising administering to the subject a therapeutically effective amount of Compound C. In another embodiment, provided herein is are methods of treating Paget's Disease in a subject in need thereof, comprising administering to the subject a therapeutically effective amount of Compound C. In still another embodiment, provided herein is a method of treating Metastatic bone disease (MBD) in a subject in need thereof, comprising administering to the subject a therapeutically effective amount of Compound C. In yet another embodiment, provided herein is a method of treating osteolytic bone lesions in a subject in need thereof, comprising administering to the subject a therapeutically effective amount of Compound C. In another embodiment, provided herein is a method of treating osteolytic bone lesions associated with MM in a subject in need thereof, comprising administering to the subject a therapeutically effective amount of Compound C. In still another embodiment, provided herein is a method of treating osteogenesis imperfecta (OI) in a subject in need thereof, comprising administering to the subject a therapeutically effective amount of Compound C. In still another embodiment, provided herein is a method of treating osteopenia in a subject in need thereof, comprising administering to the subject a therapeutically effective amount of Compound C.

Pharmaceutical Compositions and Methods of Administration

The methods described herein include the administration of pharmaceutical compositions that include HDAC6-selective inhibitory compounds described herein as active ingredients.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., calcium.

Pharmaceutical compositions are typically formulated to be compatible with their intended route of administration.

Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Combination Therapies

The methods described herein can also include the administration of additional active agents to improve treatment efficacy, in combination with an HDAC6 inhibitor, e.g., a reverse amide HDAC6 inhibitor as described herein, e.g., Compound A. For example, for the treatment or reducing risk of a condition described herein, e.g., bone loss, e.g., bone lesions associated with multiple myeloma, the methods described herein can also include administration of one or more of VELCADE® (bortezomib), Carfilzomib, ONX 0912 (an oral proteosome inhibitor), MLN9708 (an oral proteosome inhibitor), REVLIMID (lenalidomide), Pomalidomide; MLN3897 (a CCR inhibitor); LY2127399 (a BAFF-neutralizing antibody); RAP011/ACE011 (a decoy receptor for neutralizing activin A); and/or BHQ880 (a DKK1-neutralizing antibody). The methods described herein can also include the administration of bisphosphonates, which are pyrophosphate analogues characterized by high affinity for hydroxyapatitite that act by inhibiting bone resorption via actions on osteoclasts or on osteoclast precursors leading to decreases in the rate of bone resorption and an indirect increase in bone mineral density (e.g., alendronate (FOSAMAX), etidronate (DIDRONEL); ibandronate (BONIVA), pamidronate (AREDIA), risedronate (ACTONEL), tiludronate (SKELID), and/or zoledronic acid (ZOMETA); see Fleisch, Breast Cancer Res 4:30-4 (2002)); calcitonin; hormone replacement therapy; teriparatide (FORTEO); and raloxifene (EVISTA). For treating or reducing risk of a condition described herein, e.g., bone loss, e.g., associated with osteoporosis, Paget's disease, or osteogenesis imperfecta, the methods can further include the administration of bisphosphonates. For treating or reducing risk of a condition described herein, e.g., bone loss associated with bone metastasis, e.g., from breast, lung, or prostate cancer, or with hormone therapies for breast or prostate cancers, the methods can include the administration of bisphosphonates, or RANK ligands, e.g., denosumab (a humanized RANKL-neutralizing monoclonal antibody), or other therapies as known in the art, e.g., as described in Sturge et al., Nat. Rev. Clin. Oncol. 8:357-368 (2011). In some embodiments, the methods further include the administration of cathepsin K inhibitors, e.g., balicatib or odanacatib (see, e.g., Bromme and Lecaille, Expert Opin. Investig Drugs 18, 585-600 (2009)).

In some embodiments, these additional agents can be administered substantially concurrently with (e.g., in separate or the same dose form) or can be administered concurrently.

In a particular embodiment, a combination of VELCADE® (bortezomib) and a compound of Formula I is used in the methods of treatment provided herein. In another embodiment, a combination of VELCADE® (bortezomib) and Compound A is used in the methods of treatment provided herein.

In another embodiment, provided herein is a method of treating osteoporosis in a subject in need thereof, comprising administering to the subject Compound A and bortezomib. In another embodiment, provided herein is a method of treating Paget's Disease in a subject in need thereof, comprising administering to the subject Compound A and bortezomib. In still another embodiment, provided herein is a method of treating Metastatic bone disease (MBD) in a subject in need thereof, comprising administering to the subject Compound A and bortezomib. In yet another embodiment, provided herein is a method of treating osteolytic bone lesions in a subject in need thereof, comprising administering to the subject compound A and bortezomib. In another embodiment, provided herein is a method of treating osteolytic bone lesions associated with MM in a subject in need thereof, comprising administering to the subject Compound A and bortezomib. In still another embodiment, provided herein is a method of treating osteogenesis imperfecta (OI) in a subject in need thereof, comprising administering to the subject Compound A and bortezomib. In still another embodiment, provided herein is a method of treating osteopenia in a subject in need thereof, comprising administering to the subject Compound A and bortezomib.

EXAMPLES

The invention is further described in the following examples, which do not limit the scope of the invention described in the claims.

Example 1

Synthesis of 2-(diphenylamino)-N-(7-(hydroxyamino)-7-oxoheptyl) pyrimidine-5-carboxamide (Compound A)

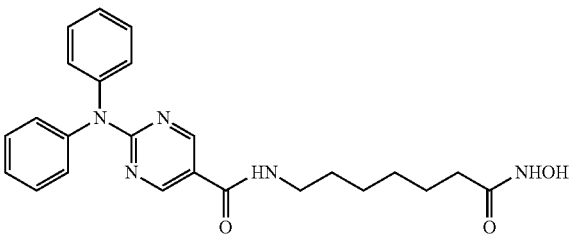

Compound A

Reaction Scheme

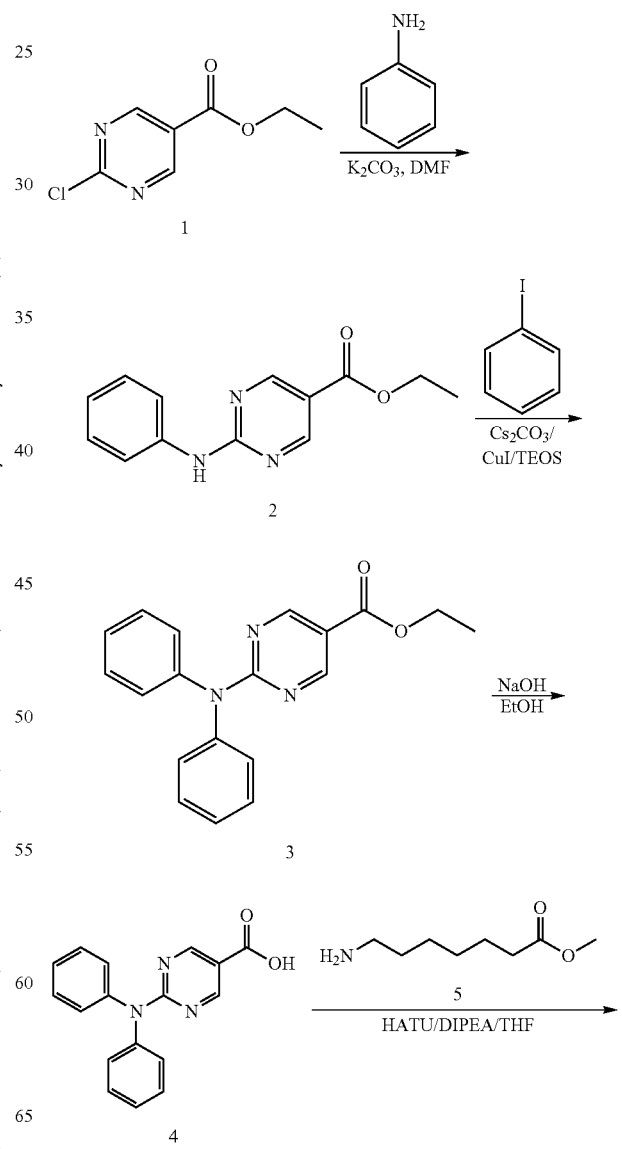

-continued

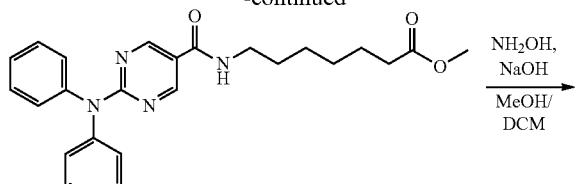

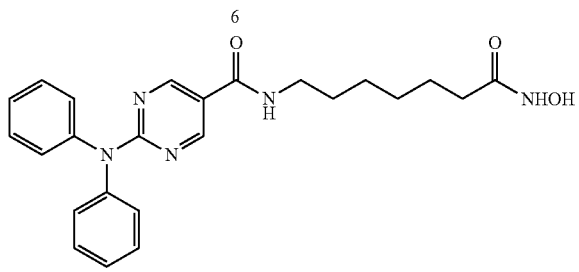

Synthesis of Intermediate 2

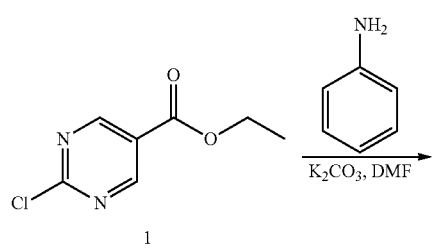

A mixture of aniline (3.7 g, 40 mmol), ethyl 2-chloropyrimidine-5-carboxylate 1 (7.5 g, 40 mmol), $K_2CO_3$ (11 g, 80 mmol) in DMF (100 ml) was degassed and stirred at 120° C. under $N_2$ overnight. The reaction mixture was cooled to room temperature and diluted with EtOAc (200 ml), then washed with saturated brine (200 ml×3). The organic layer was separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3

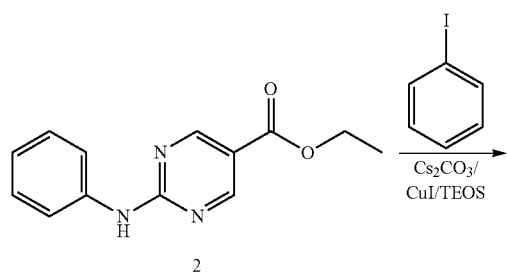

-continued

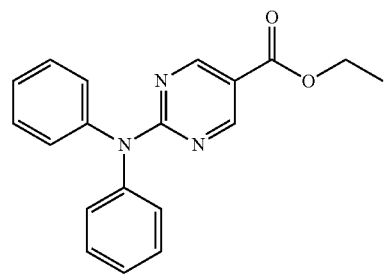

A mixture of the compound 2 (6.2 g, 25 mmol), iodobenzene (6.12 g, 30 mmol), CuI (955 mg, 5.0 mmol), $Cs_2CO_3$ (16.3 g, 50 mmol) in tetraethyl orthosilicate (TEOS) (200 ml) was degassed and purged with nitrogen. The resulting mixture was stirred at 140° C. for 14 h. After cooling to rt, the residue was diluted with EtOAc (200 ml) and 95% EtOH (200 ml), $NH_4F$—$H_2O$ on silica gel [50 g, pre-prepared by the addition of $NH_4F$ (100 g) in water (1500 ml) to silica gel (500 g, 100-200 mesh)] was added, and the resulting mixture was kept at room temperature for 2 h, the solidified materials was filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4

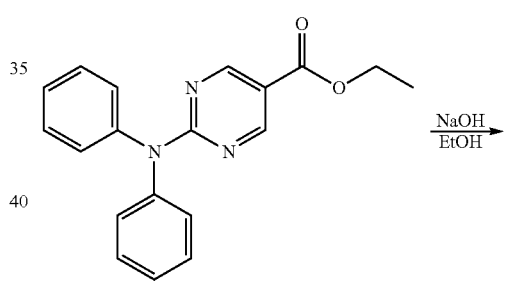

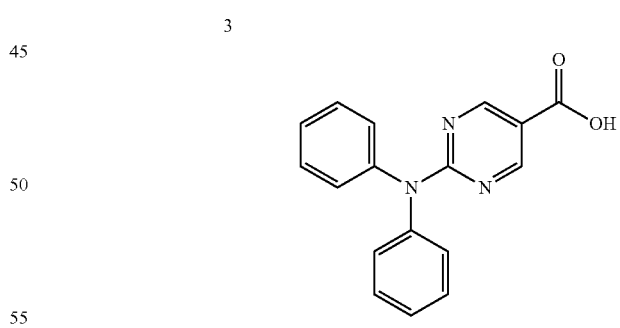

2N NaOH (200 ml) was added to a solution of the compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over $Na_2SO_4$. Removal of solvent gave a brown solid (2.5 g, 92%).

Synthesis of Intermediate 6

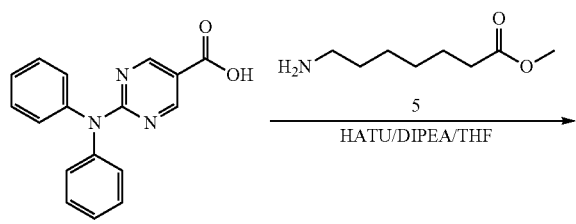

4

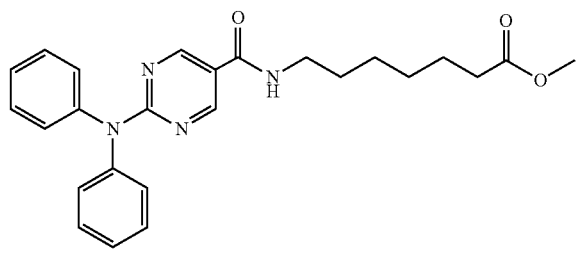

6

A mixture of compound 4 (2.5 g, 8.58 mmol), aminoheptanoate 5 (2.52 g, 12.87 mmol), O-(7-Azabenzotriazol-1-yl)-N,N,N',N'-tetramethyluronium hexafluorophosphate (HATU) (3.91 g, 10.30 mmol), N,N-Diisopropylethylamine (DIPEA) (4.43 g, 34.32 mmol) was stirred at room temperature overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide

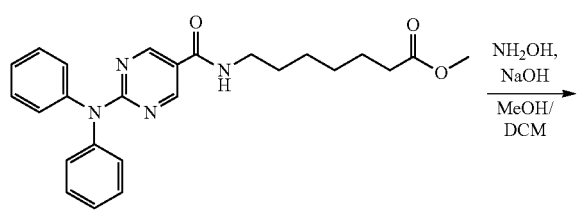

6

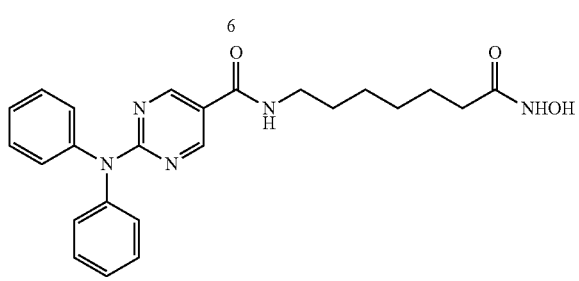

A mixture of the compound 6 (2.0 g, 4.6 mmol), sodium hydroxide (2N, 20 mL) in MeOH (50 ml) and dichloromethane (DCM (25 ml) was stirred at 0° C. for 10 min. Hydroxylamine (50%) (10 ml) was cooled to 0° C. and added to the mixture. The resulting mixture was stirred at room temperature for 20 min. After removal of the solvent, the mixture was neutralized with 1M HCl to give a white precipitate. The crude product was filtered and purified by pre-HPLC to give a white solid (950 mg, 48%).

Example 2

Synthesis of 4-(2,6-dimethylphenylamino)-N-(7-(hydroxyamino)-7-oxoheptyl)-N-methylbenzamide

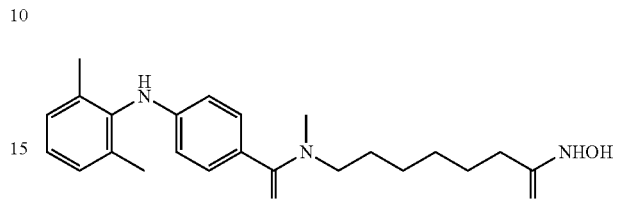

Reaction Scheme:

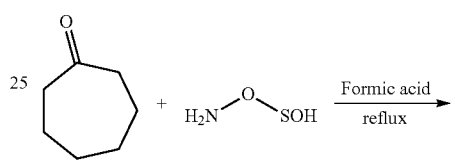

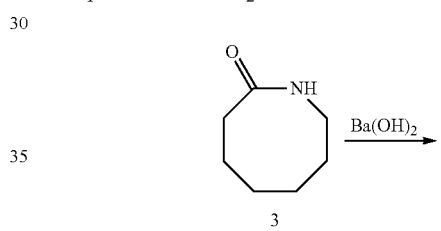

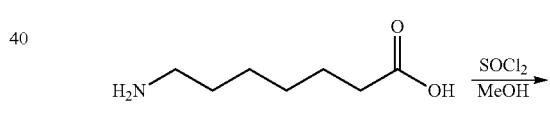

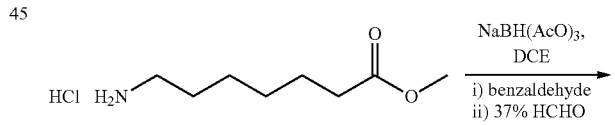

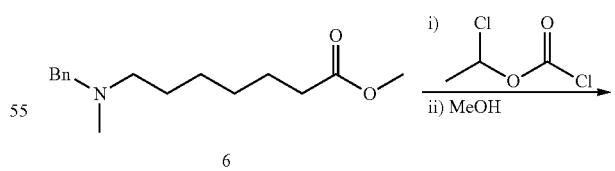

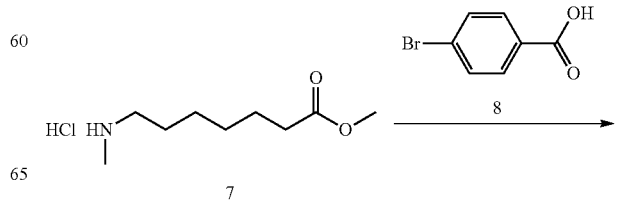

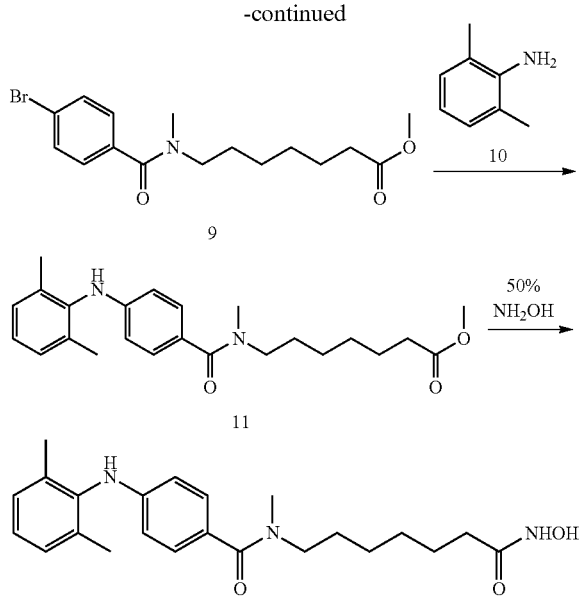

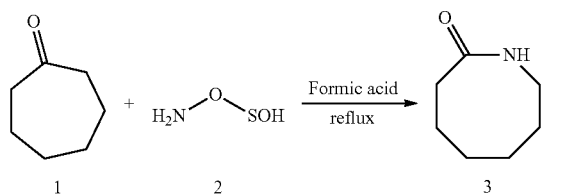

Synthesis of Intermediate 3:

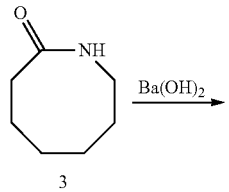

A 100-mL, three-necked flask was equipped with a magnetic stirring bar, a pressure-equalizing dropping funnel, and a reflux condenser connected to a nitrogen flow line. The system was dried with a heat gun while it was flushed with dry nitrogen. The reaction vessel was then cooled in a water bath while a light positive pressure of nitrogen was maintained. The flask was charged with hydroxylamine-O-sulfonic acid 2 (8.48 g, 0.075 mol) and 95-97% formic acid (45 ml). A solution of cycloheptanone (5.61 g, 0.05 mol) (Note 3) in 15 ml of 95-97% formic acid was added with stirring over a 3-min period. After addition was complete, the reaction mixture was heated under reflux for 5 hr and then cooled to room temperature. The reaction mixture was quenched with 75 ml of ice-water. The aqueous solution was slowly neutralized to pH 7 with 6 N sodium hydroxide and extracted with three 100-ml portions of chloroform. The combined organic layers were dried with anhydrous magnesium sulfate. After removal of the solvent on a rotary evaporator, the product hexahydroazocinone was purified by distillation to give 3 (4.6 g 72%), 133-135° C./4 mmHg.

Synthesis of Intermediate 4:

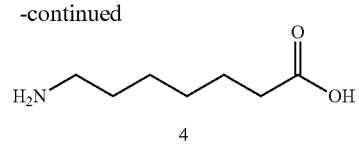

3 (5.6 g, 44.1 mmol) was combined with barium hydroxide (3.8 g, 26.95 mmol) and water (55 ml). The suspension was heated to 110° C. for 6 hours then cooled over an ice bath. Gaseous carbon dioxide was bubbled through the solution for 20 minutes. The suspension was filtered through a celite pad and the filtrate was concentrated to dryness. The residue was triturated with acetonitrile, collected, rinsed with ether and dried in vacuo to yield 4 as a white solid (6.0 g, 93%).

Synthesis of Intermediate 5:

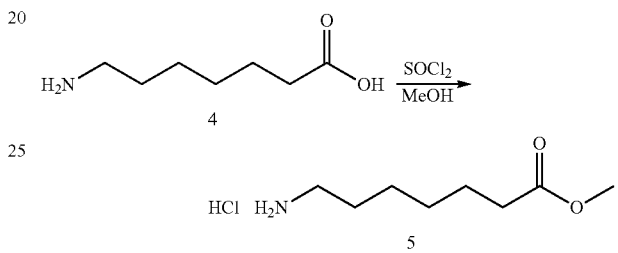

Thionyl chloride (1.81 ml, 24.8 mmol) was added dropwise with stirring to a cold suspension of 4 (1.8 g, 12.4 mmol) in methanol (30 ml.) at a rate so as to maintain the reaction temperature between −5° C. and −10° C. After addition of all the thionyl chloride, the mixture was allowed to warm to room temperature and was left to stir overnight. The mixture was then concentrated in vacuo to give a white solid which was triturated in ether (twice) to yield 2.38 g of 7-aminoheptanoic acid, methyl ester, hydrochloride (1:1) 5 as a white solid (4.8 g, 100%).

Synthesis of Intermediate 6:

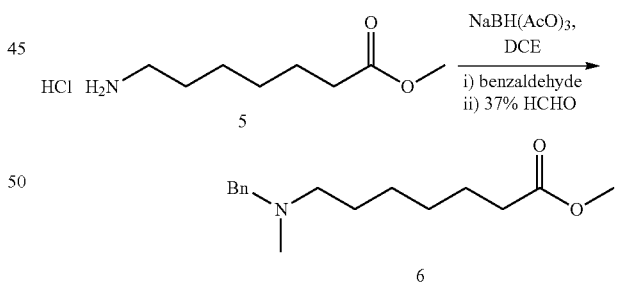

To a stirred mixture of 5 (1.67 g, 8.54 mmol), NaBH(AcO)$_3$ (10.8 g, 51.2 mmol) in 1,2 dichloroethane (DCE) (50 ml) was added benzaldehyde (1.00 g, 9.40 mmol) at ambient temperature. The resulting solution was stirred at ambient temperature for 4 hr. 37% HCHO (513 mg, 17.0 mmol) was added dropwise within 1 minute. The resulting solution was stirred at ambient temperature overnight. The solution was filtered through celite pad, and the solid cake was washed with DCM (100 ml). The combined organic layers were evaporated to dryness, and the residue was purified by silica gel column chromatography (EtOAc) to afford 6 (1.41 g, 62.8%) as colorless oil.

Synthesis of Intermediate 7:

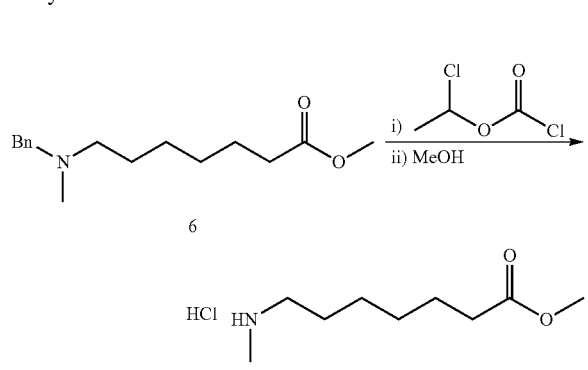

To a stirred solution of 6 (1.50 g, 5.69 mmol) in 1,2-dichloroethane (20 ml) was added 1-chloroethyl carbonochloridate (1.0 g, 6.8 mmol) dropwise at 0° C. within 2 minutes. The resulting solution was stirred at reflux for 10 hr. The solution was evaporated in vacuo, and to the residue was added MeOH (20 ml). The resulting mixture was stirred at reflux for 1 hr. The solution was then evaporated to dryness to afford crude 7 (1.3 g) as a solid which was used directly for next reaction without further purification.

Synthesis of Intermediate 9:

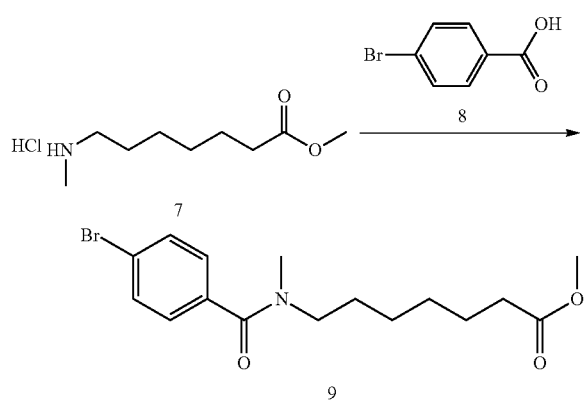

A mixture of acid 8 (2.01 g, 10 mmol), amine 7 (2.52 g, 12 mmol), DIPEA (5.17 g, 40 mmol) and HATU (4.561 g, 12 mmol) in DCM (30 ml) was stirred at room temperature for 4 hr. After the reaction mixture was evaporated to dryness, the residue was purified by silica gel column chromatography (petroleum ethers/EtOAc=1/1) to afford 9 (2.4 g, 66%) as a white solid.

Synthesis of Intermediate 11:

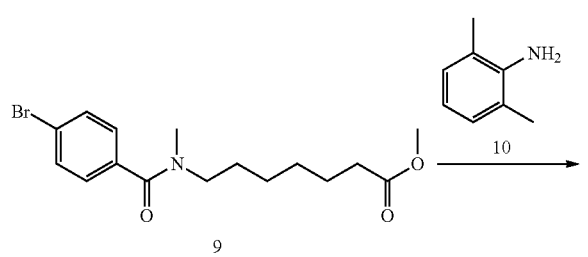

-continued

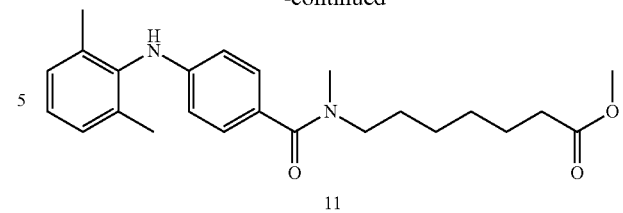

A mixture of amine 10 (0.84 g, 6.94 mmol), bromide 9 (2.06 g, 5.78 mmol), $Cs_2CO_3$ (4.52 g, 13.8 mmol), $Pd_2(dba)_3$ (64 mg, 0.069 mmol) and Xantphos (81 mg, 0.14 mmol) in toluene (20 ml) was degassed and stirred at 100° C. overnight. The reaction mixture was cooled to rt and filtered through Celite. The filtrate was evaporated to dryness and the residue was purified by silica gel chromatography (petroleum ethers/EtOAc=1/1) to afford 11 (2.21 g, 96%) as pale yellow oil.

Synthesis of 4-(2,6-dimethylphenylamino)-N-(7-(hydroxyamino)-7-oxoheptyl)-N-methylbenzamide

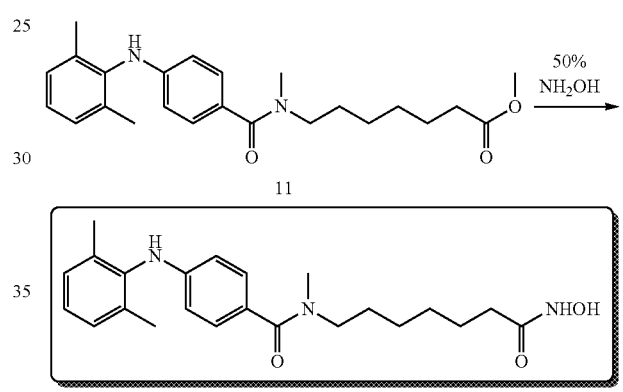

A mixture of the compound 11 (1.58 g, 4.00 mmol), 2N sodium hydroxide (10 ml, 20 mmol) in MeOH (8 ml) and DCM (60 ml) was stirred at 0° C. for 10 minutes. 50% aq. hydroxylamine (7.93 g, 120 mmol) was cooled to 0° C. and added to the mixture. And the resulting mixture was stirred at 0° C. for about 2 hour. The reaction mixture was neutralized with 2 N HCl to pH 7. After removal of solvent, the residue was extracted with EtOAc (10 ml). The organic layer was washed with water (20 ml), and brine (20 ml), dried over $Na_2SO_4$, evaporated in vacuo to afford the title compound (1.55 g, 98%) as a white solid.

Example 3

Synthesis of 2-(2,6-dimethylphenylamino)-N-(7-(hydroxyamino)-7-oxoheptyl)-N-methylpyrimidine-5-carboxamide

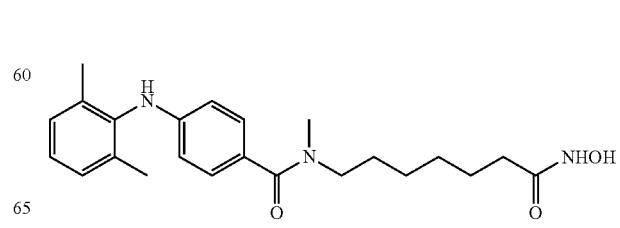

Reaction Scheme

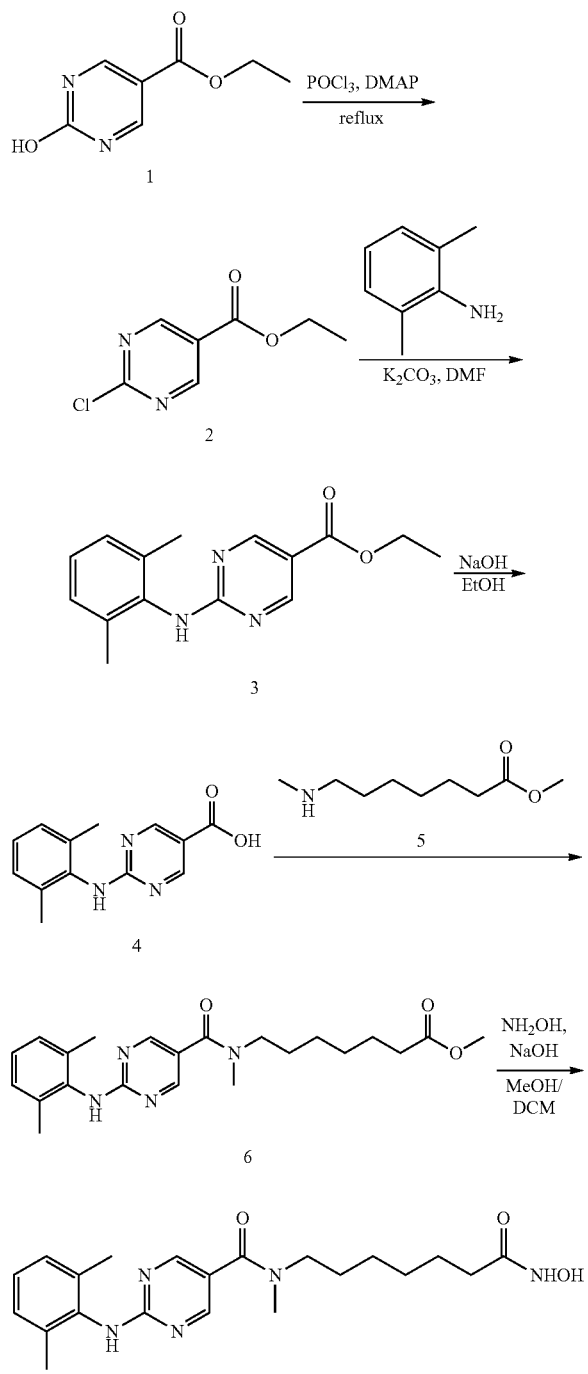

Synthesis of Intermediate 2

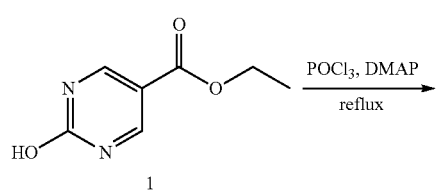

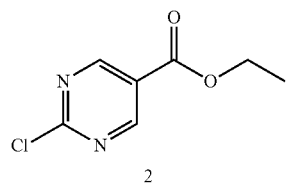

A mixture of the compound 1 (2 g, 12 mmol), N,N'-dimethylaminopyridine (DMAP) (1.32 g, 11 mmol) and POCl₃ (20 mL) was heated at reflux for 1.5 h. After removal of the solvent, EA was added to the residual. The pH of the mixture was adjusted to 7 with aq. NaOH (2M), the organic layer was then separated, washed with brine. After removal of the solvent, the residual was extracted with PE and dried over Na₂SO₄, evaporation of the solvent gave a light yellow solid (1 g, 45%).

Synthesis of Intermediate 3

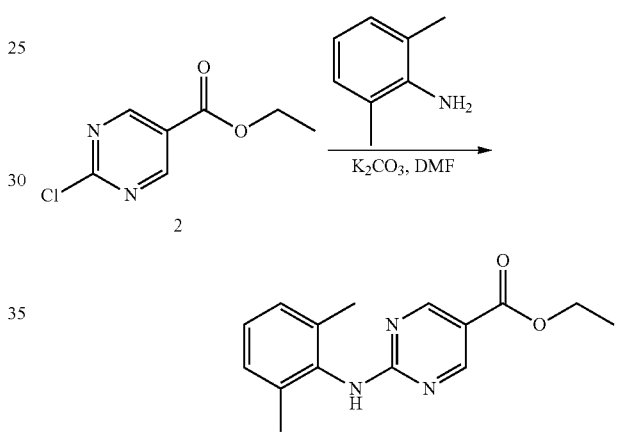

A mixture of aniline (325 mg, 2.68 mmol), compound 2 (500 mg, 2.68 mmol), K₂CO₃ (370 mg, 2.68 mmol) in N,N'-dimethylformamide (DMF) (10 mL) was degassed and stirred at 140° C. overnight. The reaction mixture was cooled to room temperature and filtered. The filtrate washed with water (2×20 mL) and brine (2×20 mL), extracted with EA. The organic layer was dried over Na₂SO₄, and evaporated to dryness. The residue was purified by silica gel chromatography (PE/EA=5/1) to give the crude product as a brown oil (320 mg, 44%).

Synthesis of Intermediate 4

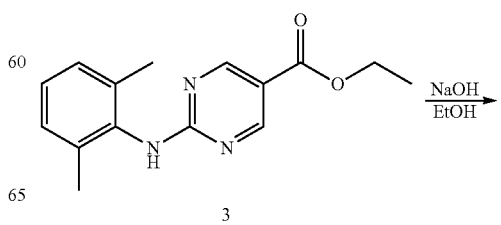

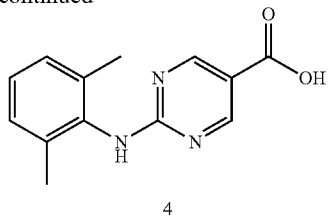

2M NaOH (15 mL) was added to a solution of the compound 3 (320 mg, 1.18 mmol) in EtOH (15 mL). The mixture was stirred at 60° C. for 10 minutes. The solution was neutralized with 2M HCl and extracted with EA (2×60 mL). The organic layer was washed with water (2×20 mL), brine (2×20 mL), and dried over $Na_2SO_4$. Evaporation of the solvent left a white solid (270 mg, 94%).

Synthesis of Intermediate 6

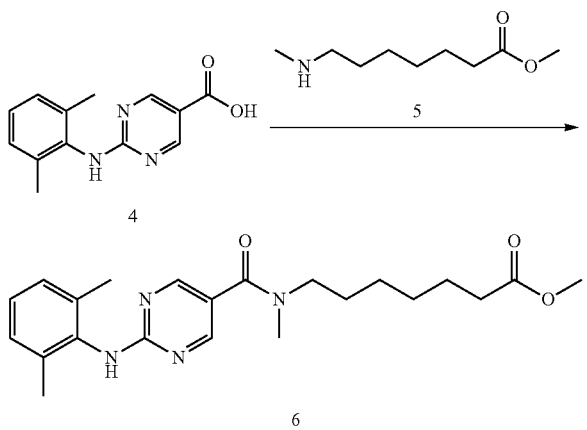

A mixture of compound 4 (270 mg, 1.11 mmol), compound 5 (231 mg, 1.33 mmol), HATU (506 mg, 1.33 mmol), DIPEA (574 mg, 4.44 mmol) in THF (30 mL) was stirred at room temperature overnight. The reaction mixture was filtered. The filtrate was evaporated to dryness and the residue was purified by pre-TLC (PE/EA=1/2) to give a brown oil (320 mg, 72%).

Synthesis of 2-(2,6-dimethylphenylamino)-N-(7-(hydroxyamino)-7-oxoheptyl)-N-methylpyrimidine-5-carboxamide

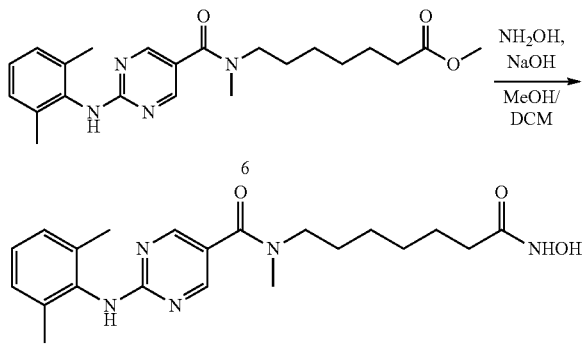

A mixture of the compound 6 (200 mg, 0.50 mmol), NaOH (2 M, 2 mL) in MeOH (8 mL) and DCM (4 mL) was stirred at 0° C. for 10 minutes. Hydroxylamine (0.4 mL) was cooled to 0° C. and added to the mixture. After the resulting mixture was stirred at room temperature for 20 min, the organic solvent was removed in vacuo. The residue was acidified with 1M HCl to pH 7 and extracted with EA. The organic layer was washed with water (2×20 mL), brine (2×20 mL), and dried over $Na_2SO_4$, evaporated to dryness, and the residue was purified by pre-TLC (DCM/MeOH=5/1) to give a brown solid (106 mg, 53%).

Example 4

Synthesis of N-(7-(hydroxyamino)-7-oxoheptyl)-4-(hydroxydiphenylmethyl)benzamide Reaction Scheme

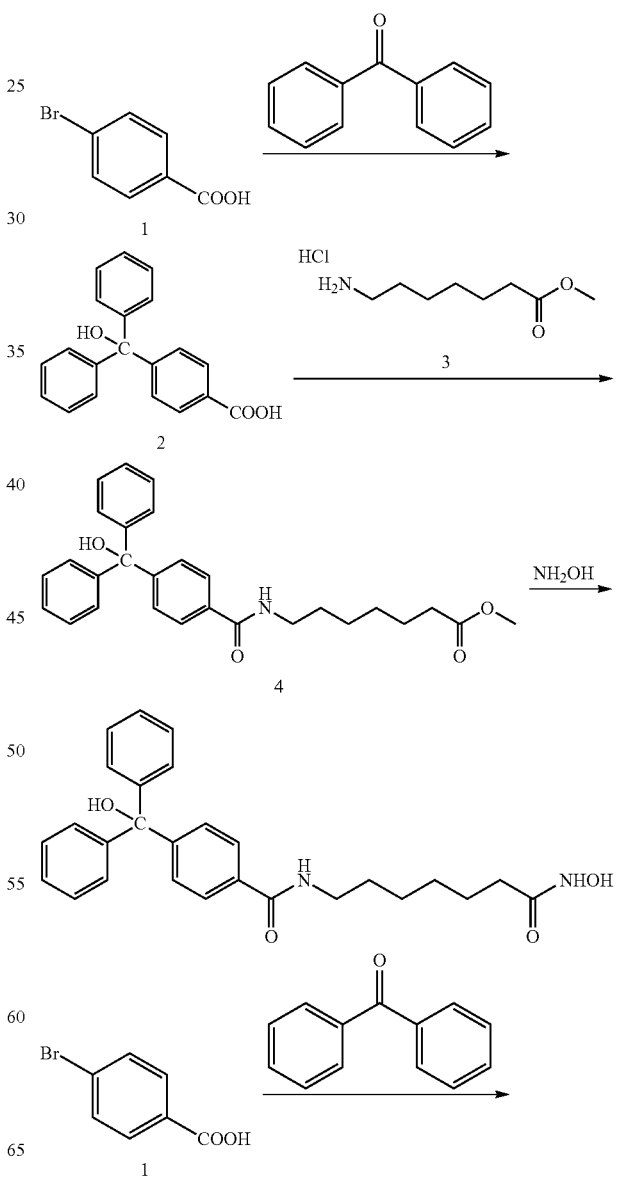

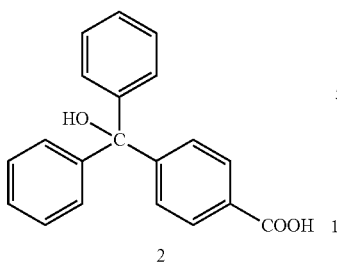

2

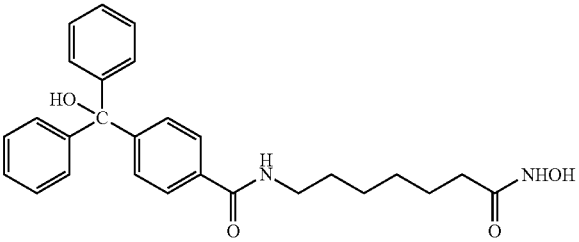

To a solution of 1 (201 mg, 1 mmol) in dry THF (5 ml), n-butyllithium solution (1.6 M in hexane, 1.5 ml) was added dropwise at −65° C. After 5 minutes, a solution of benzophenone (182 mg in 5 ml dry THF) was added over 10 minutes (exothermic). The mixture was stirred for further 30 minutes at −65° C. and overnight at r.t. The reaction mixture was quenched with sat. NH₄Cl (10 ml) and concentrated under reduced pressure. The mixture was acidified to pH 4 with 2N HCl, extracted with ethyl acetate (2×10 ml). The organic layer was separated, dried over Na2SO4 and concentrated to dryness. The residue was purified with prep-TLC (DCM/MeOH=10:1) to give compound 2 as a white solid (205 mg, 67%).

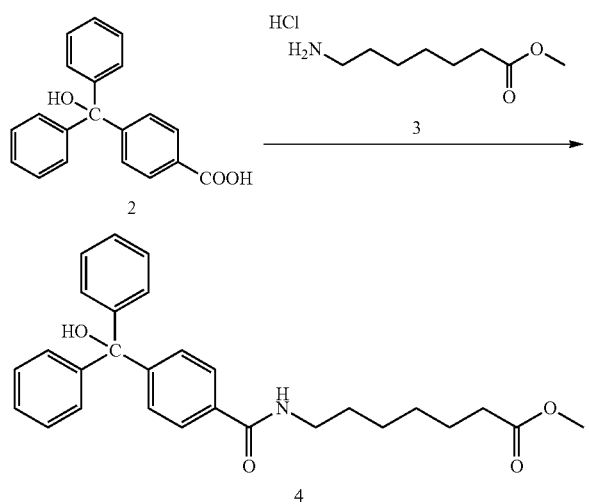

A solution of 2 (150 mg, 0.49 mmol), EDCI (190 mg, 0.98 mmol), HOBt (132 mg, 0.98 mmol) and 3 (190 mg, 0.98 mmol) in THF (10 mL) was stirred at room temperature for 2 hours. The reaction mixture was concentrated under reduced pressure and the residue was purified by prep-TLC to give compound 4 as an yellow oil (124 mg, 56%).

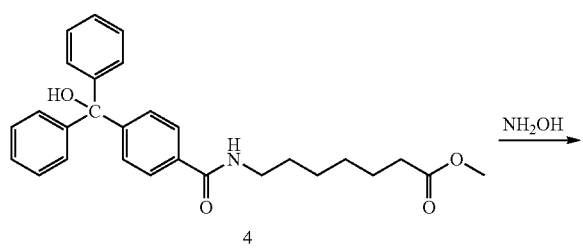

A solution of 4 (124 mg, 0.27 mmol) in MeOH (5 mL) was treated with NaOH (sat. in MeOH, 1.0 ml) and aq. NH₂OH (50 wt %, 0.55 ml) sequentially and was stirred at room temperature for 30 min. The reaction mixture was slowly acidified to pH 6-7 with 2N HCl, and extracted with ethyl acetate (2×5 ml). The organic layer was separated, dried over Na₂SO⁴ and concentrated under reduced pressure to afford the titled compound as a yellow solid (111 mg, 90%).

Example 5

HDAC Enzyme Assays

Compound A was diluted in DMSO to 50-fold the final concentration and a 10-point, 3-fold dilution series was prepared. Compound A was subsequently diluted in assay buffer (50 mM HEPES, pH 7.4, 100 mM KCl, 0.001% Tween-20, 0.05% bovine serum albumin (BSA), 20 µM tris(2-carboxyethyl)phosphine) to 6-fold the final concentration. HDAC enzymes were diluted to 1.5-fold of the final concentration in assay buffer and pre-incubated with Compound A for 10 minutes prior to the addition of the substrate. The amount of fluorophore tripeptide substrate (FTS) or the amount of the Class IIa tripeptide substrate MAZ-1675 used for each enzyme was equal to the Km as determined by a FTS titration curve. The enzyme and FTS concentrations used for HDAC1, HDAC2, HDAC3, and HDAC6 were 3.5, 0.2, 0.08 and 0.25 ng/µL and 3.8, 2.3, 3.9 and 2.8 µM, respectively. The amount of enzyme and MAZ-1675 used for HDAC 4, HDAC5, HDAC7, HDAC8 and HDAC9 were 0.2, 0.1, 0.01, 0.033, and 0.4 ng/µl and 34.5, 84, 42.5, 111, and 49.4 µM, respectively.

FTS or MAZ-1675 was diluted in assay buffer to 6-fold the final concentration with 0.304 sequencing grade trypsin (Sigma). The substrate/trypsin mix was added to the enzyme/compound mix, and the plate was shaken for 60 seconds and then placed into a SpectraMax® M5 microtiter plate reader. Deacetylation of the lysine side chain on the substrate peptides allows trypsin to cleave the substrate to produce a 7 amino-4-methoxy-coumarin AMC group that can be measured by fluorescence. The enzymatic reaction was monitored for 30 min and the linear rate of the reaction was calculated. The IC$_{50}$ was determined using Graph Pad Prism with a 4 parameter curve fit.

Compound A demonstrated potent and selective inhibitory activity against HDAC6 with an enzymatic IC$_{50}$ value of 5 nM. Compound A is 12-, 10-, and 11-fold less active against HDACs 1, 2, and 3 (Class I HDAC), respectively (Table 3). Compound A has minimal activity (IC$_{50}$>1 µM) against HDACs 4, 5, 7, 9, 11, and sirtuin 1 and 2 and slight activity against HDAC8 IC$_{50}$ 0.1 µM.

TABLE 3

| Inhibition of HDAC Enzymes | | |
|---|---|---|
| Enzyme | $IC_{50}$ (nM) | Fold Potency vs HDAC6 |
| HDAC1 | 58 | 12 |
| HDAC2 | 48 | 10 |
| HDAC3 | 51 | 11 |
| HDAC4 | 7,000 | 1500 |
| HDAC5 | 5,000 | 1100 |
| HDAC6 | 4.7 | — |
| HDAC7 | 1,400 | 300 |
| HDAC8 | 100 | 21 |
| HDAC9 | >10,000 | >2100 |
| HDAC11 | >10,000 | >2100 |
| Sirtuin 1 | >10,000 | >2100 |
| Sirtuin 2 | >10,000 | >2100 |

To confirm the specific inhibitory effect of Compound A on HDAC6 activity its effect on the acetylation of α-tubulin was evaluated. MM.1S cells were cultured with increasing doses of Compound A for 18 hours. A dose dependent significant increase in the acetylated α-tubulin was observed even in the presence of low doses (0.04 μM) of Compound A. Importantly, Compound A induced less potent acetylation of lysine on Histone H3 and Histone H4 compared to SAHA, confirming its more specific inhibitory effect on HDAC6 activity. Similar acetylation selectivity for α-tubulin was observed in other MM cell lines such as MM.1R and RPMI. The specific inhibitory effect of Compound A on HDAC6 activity on acetylation of α-tubulin in primary MM cells was next evaluated. CD138+ MM patient cells were treated with and without Compound A at 2 μM for 4 hours. Western blot analysis showed a significant increase of ac-α-tubulin in treated compared to control cells. To further evaluate the inhibitory effect of Compound A on HDAC6 activity, its effect on acetylation of α-tubulin versus Histone H3 was analyzed in CD138+ MM patient cells by immunohistochemistry (IHC). CD138+ MM patient cells were fixed and double stained with anti-human CD138 and with anti-ac-α-tubulin or anti-acetyl-Histone H3. A significant increase of ac-α-tubulin was observed in treated compared to control cells, without any significant increase in acetyl-Histone H3.

These results confirm the selective inhibitory effect of Compound A on HDAC6 activity.

Examples Relating to Bone Metabolism

Example 6

Compound A Effects on Viability and Function of OBLs

To evaluate effects of Compound A on osteoblast (OBL) viability and function, osteoblasts were differentiated from bone marrow stromal cells (BMSCs) derived from MM patients and treated with Compound A (1 μM) bortezomib (2.5 nM) or a combination of Compound A and bortezomib (1 μM and 2.5 nM, respectively) for 10-14 and 21 days (Mallet et al., Proc Natl Acad Sci USA. 2010 Mar. 16; 107(11):5124-9).

AlamarBlue Assay

Alamarblue was added to the wells to a final concentration of 10% alamar blue and the plates were incubated at 370 C and 5% CO2 for 1 to 4 hours. The plates were read at absorbance (OD) of 530 nm and 600 nm. The delta OD was recorded and the date were plotted as percentage of control.

Alkaline Phosphatase (ALP) Activity Assay

Following the AlamarBlue cell viability assay, the wells were then washed twice with PBS fixed for 5 minutes and washed again with distilled water and Alkaline Phosphatase Yellow (pNPP) Liquid Substrate System for ELISA (sigma-aldrich) was added to the wells. The plates were read at OD of 405 nm after 5 minutes of incubation.

Alizarin Red Staining

To evaluate calcium deposition, osteoblasts were washed with PBS and fixed after 23 days of treatment and assayed by alizarin red staining (Alizarin red solution, Millipore) that specifically stains mineralization area. The mineralization areas were visualized using Nikon Labophot-2 microscope with 10×/0.25 lens equipped with SPOT-insight QE camera.

Figure 1C:
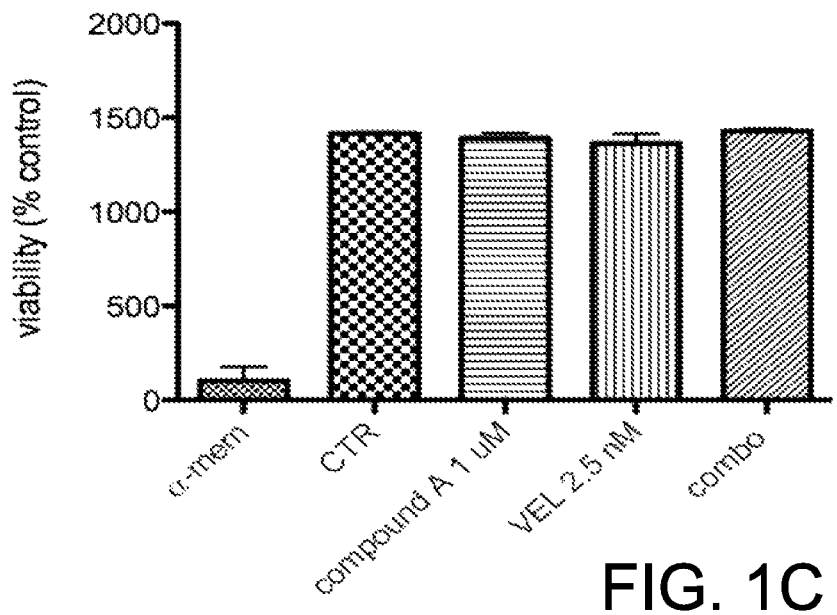
Figure 1D:
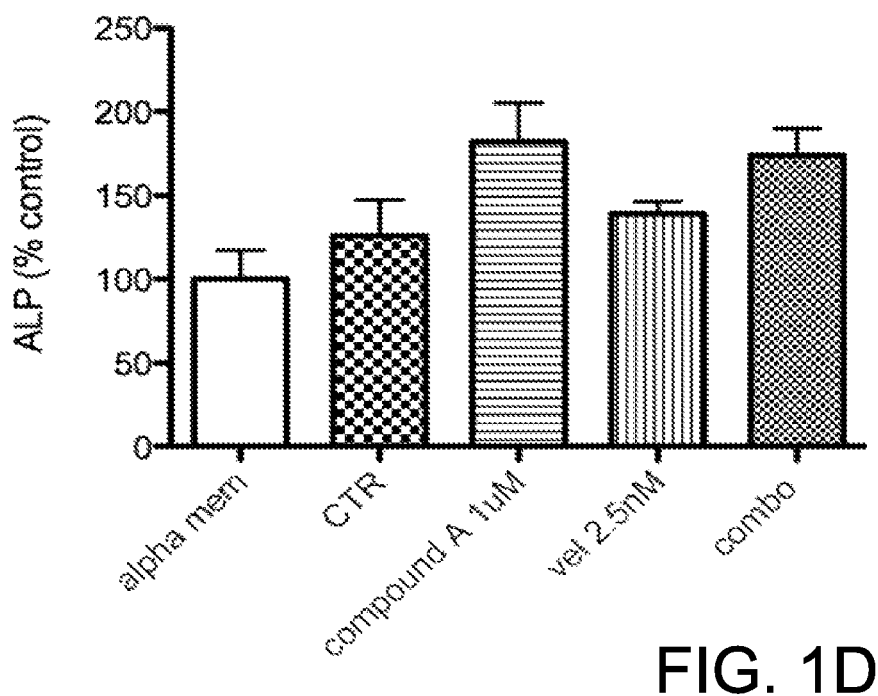
Figure 2A:
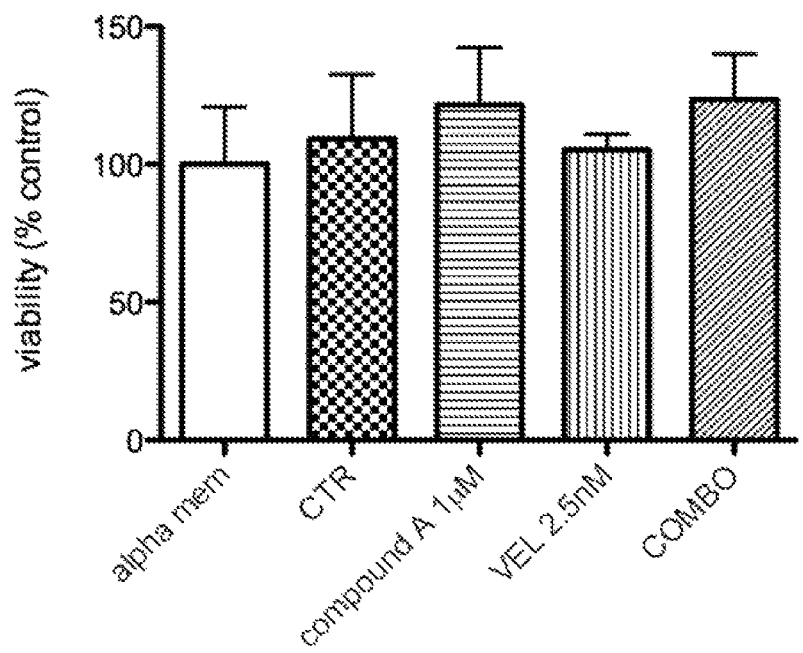
FIGS. 2 A-D are four bar graphs showing that Compound A alone and in combination with bortezomib does not affect the viability of OBLs (2A and 2C, AlamarBlue) and increases OBLs function (2B and 2D), alkaline phosphatase (ALP) activity).
Figure 2B:
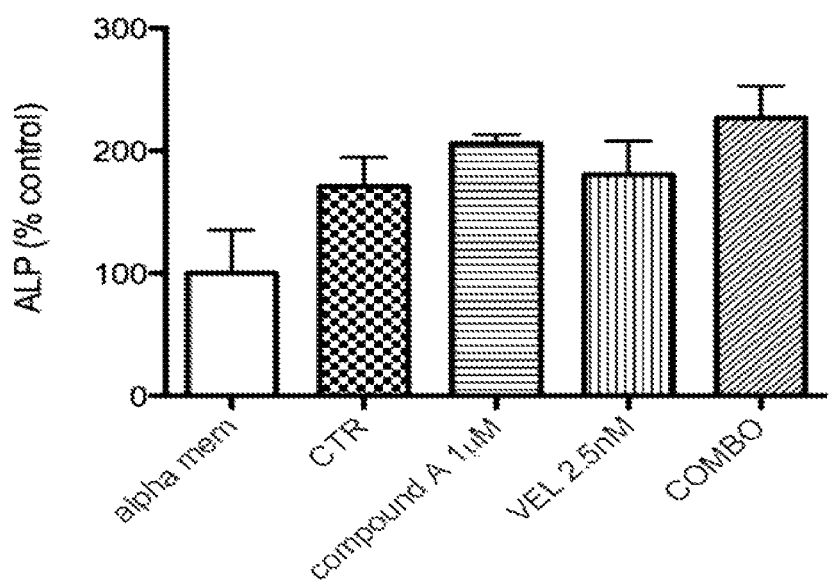
Figure 2C:
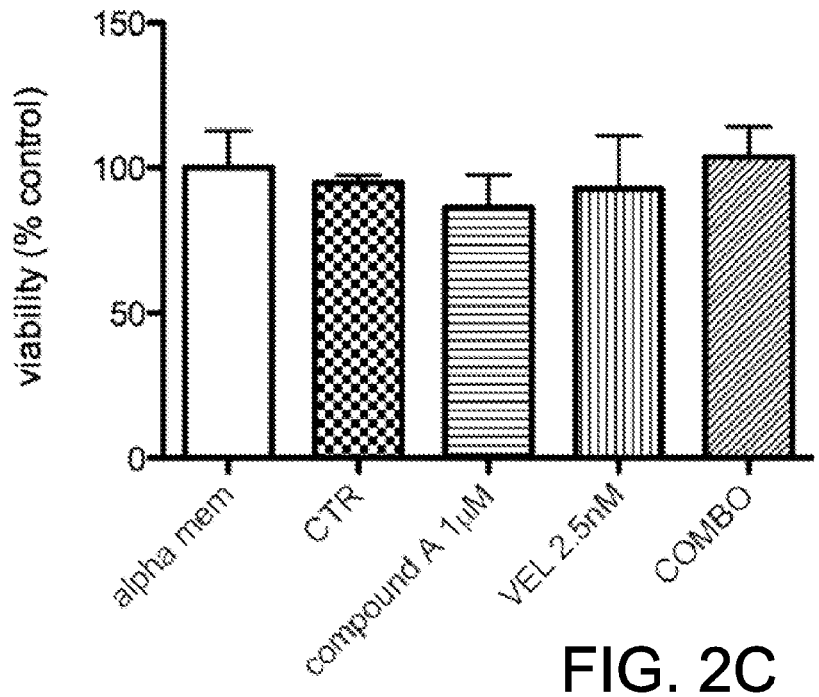
Figure 2D:
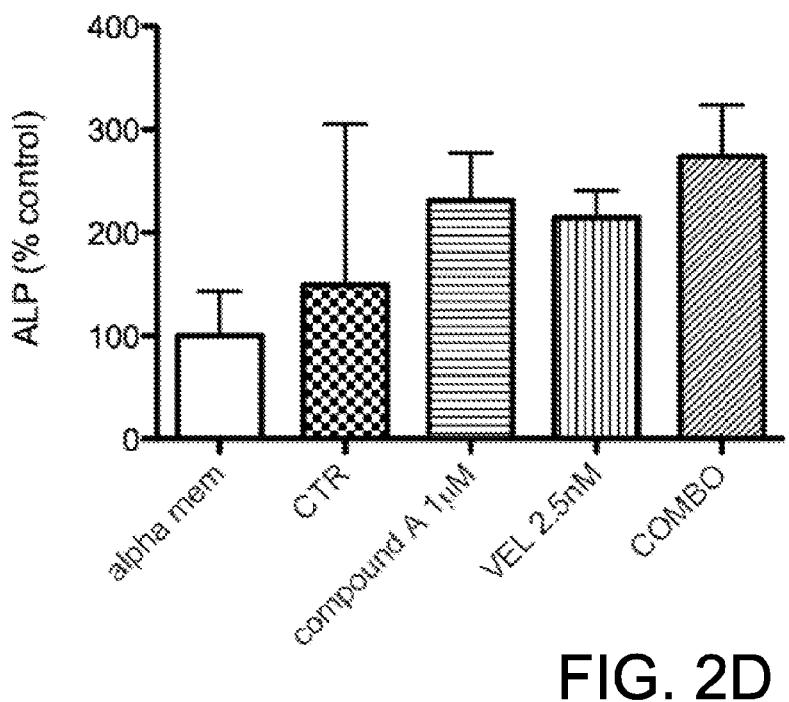
Figure 3A:
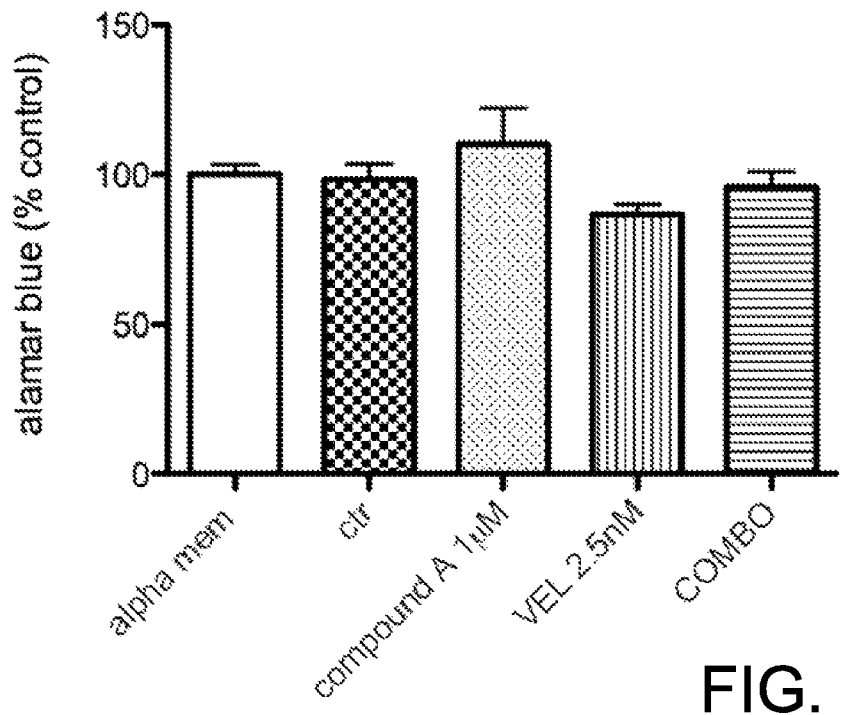
FIGS. 3A-B are bar graphs showing that Compound A alone and in combination with bortezomib does not affect the viability of OBLs (3A, AlamarBlue) and increases OBLs function (3B, alkaline phosphatase (ALP) activity).
Figure 3B:
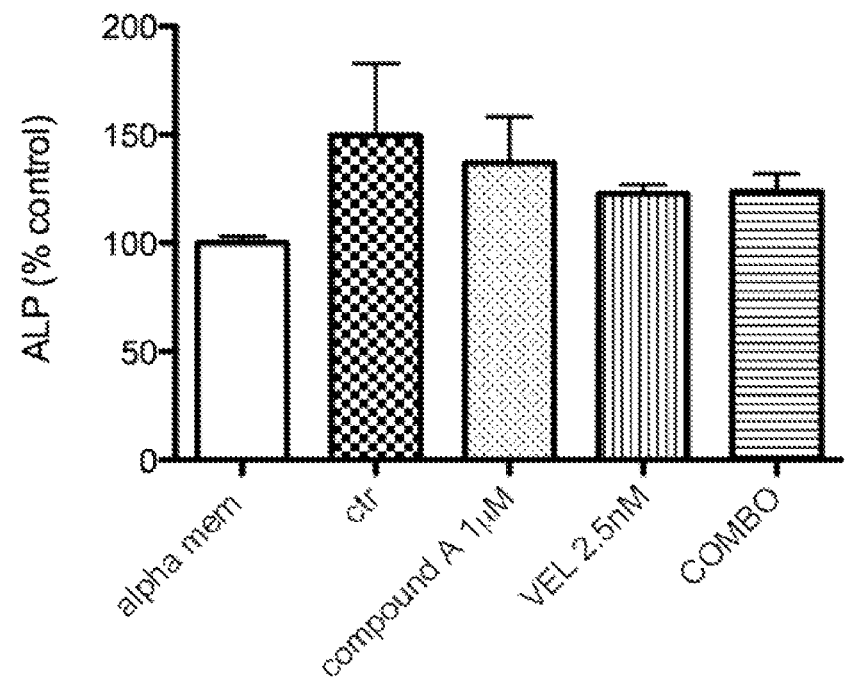

BMSCs from MM patients (indicated as alpha-mem in FIGS. 1-6) were differentiated in OBL and treated with compound A (1 μM and/or Bortezomib 2.5 nM) for 10-14 and 21 days. The control (ctr) represents the OBL without any treatment. Cell viability was assessed by Alamarblue assay (a redox indicator that yields a colorimetric change and a fluorescent signal in a response to a metabolic activity) (Invitrogen, Carlsbad, Calif.). The results, shown in FIGS. 1A-D, 2A-D, and 3A-B, demonstrated that Compound A alone and in combination with bortezomib does not affect the viability of OBLs and increases OBLs function. (FIG. 1A alarm blue after 14 days of differentiation in BMSC derived from patient 1, FIG. 1C alarm blue after 21 days of differentiation in BMSC derived from the same patient, FIG. 2A alarm blue after 14 days of differentiation in BMSC derived from patient 2, FIG. 2C alarm blue after 21 days of differentiation in BMSC derived from patient 2, FIG. 3A alarm blue after 10 days of differentiation in BMSC derived from patient 3).

Following cell viability analysis, wells were washed, fixed and stained with alkaline phosphatase staining that showed increased osteoblast functions. (FIG. 1B ALP after 14 days of differentiation in BMSC derived from patient 1, FIG. 1D ALP after 21 days of differentiation in BMSC derived from the same patient, FIG. 2B ALP after 14 days of differentiation in BMSC derived from patient 2, FIG. 2D ALP after 21 days of differentiation in BMSC derived from patient 2, FIG. 3B ALP after 10 days of differentiation in BMSC derived from patient 3). These results show that compound A does not induce cytotoxicity on OBL cells and it increases the alkaline phosphate activity, a marker of OBL function, at day 14 and 21.

The effect on the osteoblast differentiation was confirmed by Alizarin Red staining OBLs were differentiated in the presence of Compound A and/or bortezomib for 23 days. The results, shown in FIGS. 4C and 4E, demonstrated that Compound A alone and in combination with bortezomib increases calcium deposits in OBL cells, as determined Alizarin Red staining. The results shown in FIG. 4A "CTR alpha-mem" represent the BMSCs that have not been differentiated in OBL. The results shown in FIG. 4B "CRT OBL medium" represent the OBL without any treatment.

Example 7

Compound A Effects on Osteoclastogenesis and OCL Function

To evaluate the effects of Compound A on osteoclastogenesis, osteoclasts were differentiated from peripheral blood mononucleated cells (PBMCs) from MM patients as follows. PBMCs were separated by Ficoll-Paque gradient and cultured in 6-well or 96-well plates (0.5×106 cells/cm2). Osteoclasts (OCLs) were generated by culturing cells in α-MEM containing 10% fetal bovine serum (FBS), 1% penicillin-streptomycin (Mediatech Inc., Herndon, Va., USA), as well as 50 ng/ml of M-CSF (R&D Systems, Minneapolis, Minn., USA) and RANKL (PeproTech, Rocky Hill, N.J., USA). The cells were cultured with Compound A and/or bortezomib for 7 and 14 days.

The effects on OCLs were evaluated by TRAP staining using an acid phosphatase leucocyte staining kit (Sigma Chemical, Saint Louis, Mo., USA), according to the manufacturer's instructions.

Figure 5A:
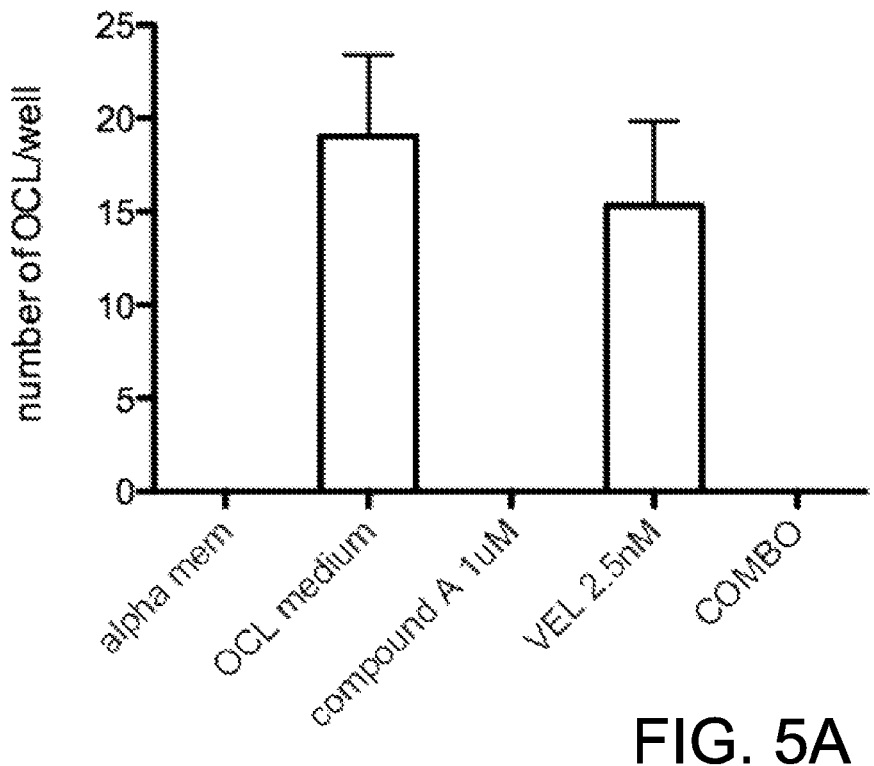
FIGS. 5A-5B are bar graphs showing that Compound A alone and in combination with bortezomib inhibits osteoclastogenesis.
Figure 5B:
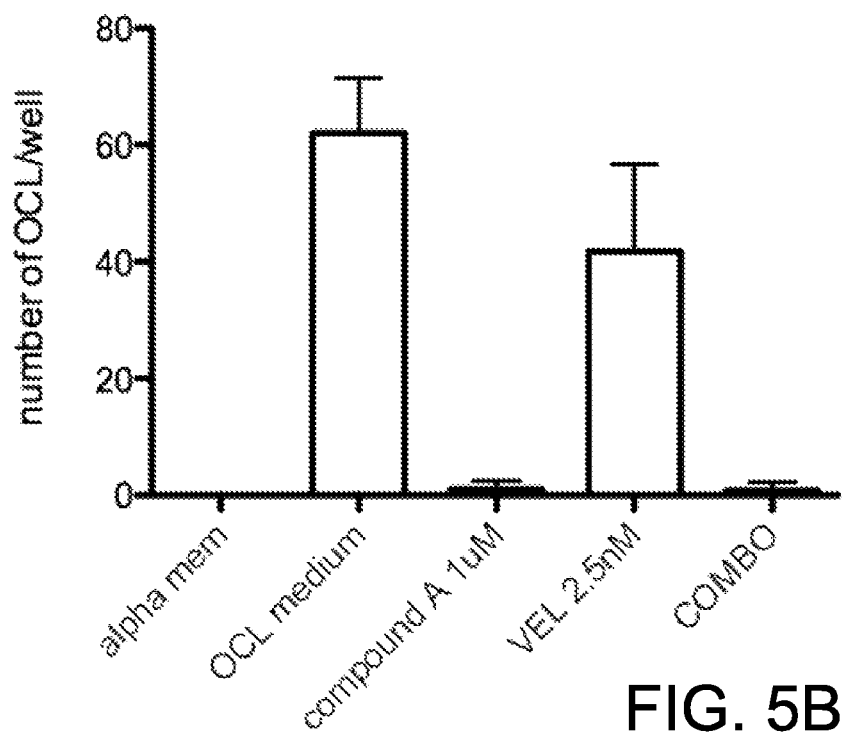
Figure 6A:
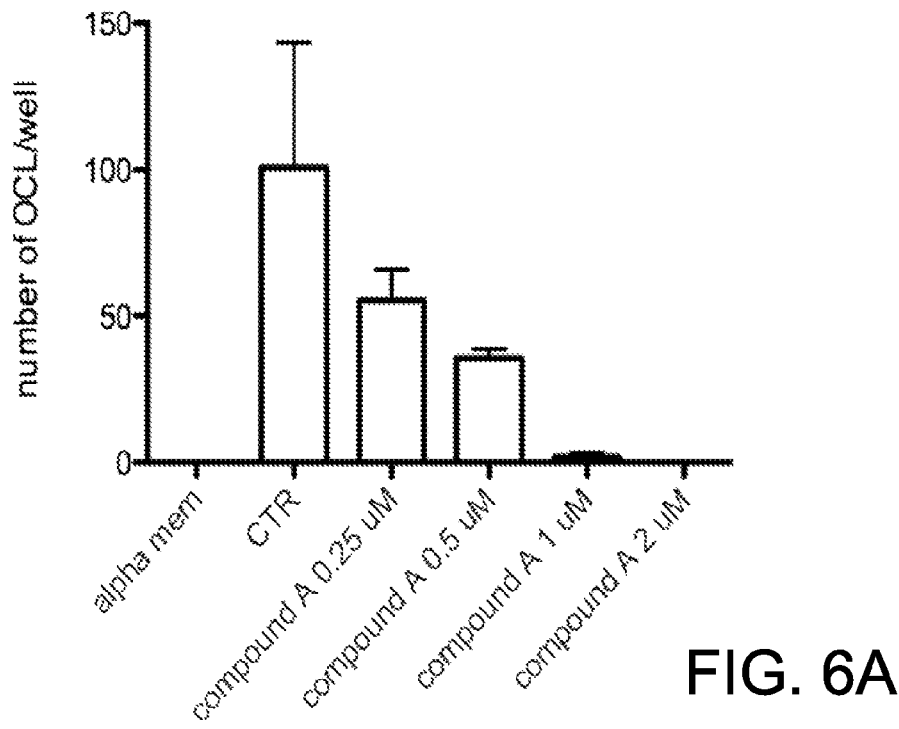
FIGS. 6A-6B are bar graphs showing that Compound A inhibits osteoclastogenesis in a dose-dependent manner at days 7 and 14 of osteoclast differentiation, respectively.
Figure 6B:
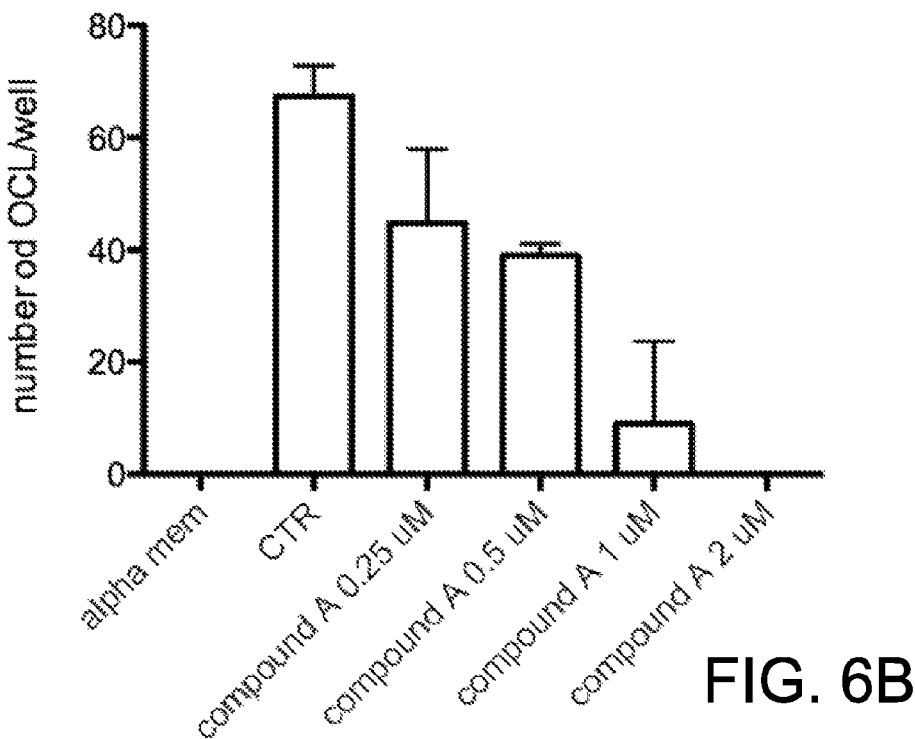

The results, shown in FIGS. 5A-5B, show that Compound A alone and/or in combination with bortezomib significantly decreases the number of OCLs (multinucleated TRAP-positive cells) per well compared with bortezomib or untreated control wells. As seen in FIGS. 6A-6B, compound A decreases the number of OCLs (multinucleated TRAP-positive cells) per well in a dose dependent manner.

Figure 7:
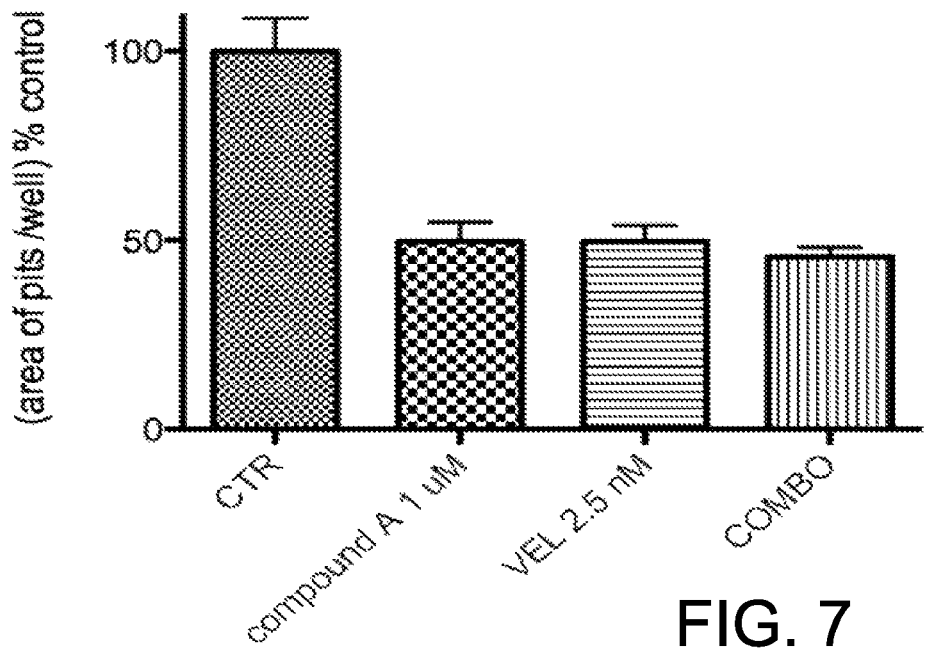
FIG. 7 is a bar graph showing the effects of Compound A alone and in combination with bortezomib on pit formation quantified using image analysis software.

In order to evaluate the effect of Compound A on osteoclasts function a PIT formation assay was performed. Osteoclasts were differentiated from MM patient bone marrow and cultured with 1 μM Compound A and/or 2.5 nM bortezomib for 7 days as described above. OC activity was assayed by bone resorption enumerating resorption pits. Briefly, mononuclear cells ($1.8 \times 10^6$ cell/well) from MM patient bone marrow were cultured in a 24-well plate coated with a synthetic carbonate apatite (CaP) (Cosmo Bio Co., Ltd, Tokio, Japan) and stimulated with RANKL (25 ng/ml) and M-CSF (25 ng/ml). Compound A 1 μM and/or bortezomib 2.5 nM were added for 7 days. On day 7 the conditioned medium was removed from each well and the wells were treated with 5% sodium hypochlorite for five minutes. After washing and drying, resorption pits were photographed by light microscopy and quantified by Image J software. Each pit area assay was performed at least 3 times with BM from different donors. As shown in FIG. 7, Compound A alone and in combination significantly arrested PIT formation, confirming its inhibitory effect on osteoclast activity.

To delineate the molecular mechanism of this inhibition, the effect of Compound A on the signaling pathway involved in OCL survival and differentiation was investigated. OCLs were differentiated for 10 days and then treated with Compound A and or bortezomib for 24 hours. Samples were then subjected to sodium dodecyl sulfate-polyacrylamide gel electrophoresis, transferred to PVDF membrane, and immunoblotted with antibodies against pAkt, Akt, and c-fos (Cell Signaling Technology, Beverly, Mass.) or phosphorylated extracellular signal-regulated kinase (pERK). Antigen-antibody complexes were detected by enhanced chemiluminescence (Amersham, Arlington Heights, Ill.). The membrane was stripped and reprobed with antitubulin antibody to ensure equal protein loading. Films were scanned and densitometric analysis performed.

Figure 8:
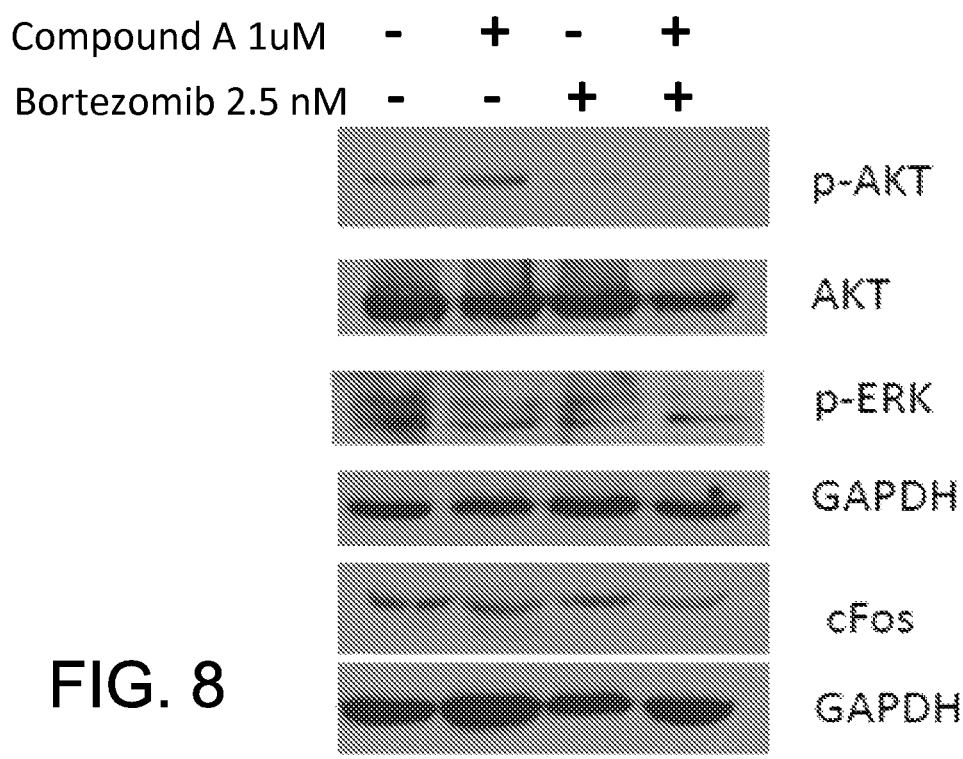
FIG. 8 is a blot showing the effect of Compound A alone and in combination with bortezomib on expression of p-AKT, AKT, p-ERK, GAPDH, and cFos in osteoclasts (OCLs) 10 days after differentiation.

The multinucleation step in OCL differentiation is regulated by c-fos (Ishida et al., J Biol Chem. 277:41147-41156 (2002); Grigoriadis et al., Science. 266:443-448 (1994)). In particular, osteoclastogenesis depends on stable c-fos expression maintained by sustained ERK signaling (Coronella-Wood et al., J. Biol Chem. 279:33567-33574 (2004)). The results, shown in FIG. 8, indicated a downregulation of pERK, pEKT and cFOS expression, which is associated with inhibition of multinucleated cell formation.

Thus, Compound A alone and in combination with bortezomib inhibits osteoclastogenesis and osteoclast function.

Example 8

Effects of Compound A on Bone Turnover In Vivo

To characterize the effect of Compound A and bortezomib combination on bone modeling focusing on bone structure, OBL and OCL activity is evaluated in an in vivo mouse model, a previously established MM xenograft model in severe combined immunodeficient (SCID) mice (Santo et al., Clin Cancer Res. 2011 May 15; 17(10):3259-71). Briefly, 40 male (10 mice in control group, 10 mice in Compound A 50 mg/kg treatment, 10 mice in bortezomib 0.5 mg/kg treatment and 10 mice for the combination therapy) CB17-SCID mice from Jackson Laboratories (Charles River Laboratories, USA) are irradiated and injected 24 hours after irradiation subcutaneously with MM1.S cells. Blood is collected at baseline and every week. After 3 weeks of treatment mice are sacrificed and bone from femurs and tibias is evaluated. Bone mineral density is evaluated after sacrifice using dual-energy X-ray absorptiometry. Trabecular bone morphology and cortical bone morphology is evaluated as previously described (Pozzi et al., Clinical Cancer Research. 15:5829-39 (2009)). RNA is extracted from tibias, converted to cDNA and expression levels of mRNAs associated with OBL maturation are evaluated by RT-PCR. Serum from blood is used to evaluate the levels of osteocalcin and TRAcP5b, markers of bone formation and bone resorption.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating, or reducing risk of, osteoporosis associated with abnormally high bone catabolism in a subject, the method comprising administering to the subject a therapeutically effective amount of a reverse amide compound of formula IVa:

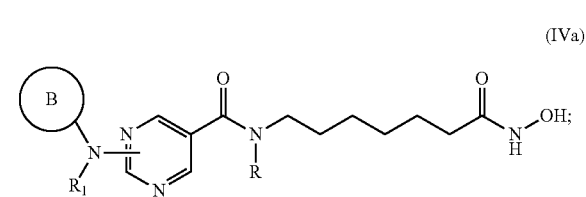

or a pharmaceutically acceptable salt thereof, wherein, ring B is phenyl;
$R_1$ is phenyl, which may be optionally substituted by OH or halo; and
R is H or C1-8-alkyl.

2. The method of claim 1, wherein the reverse amide compound is 2-(diphenylamino)-N-(7-(hydroxyamino)-7-oxoheptyl)pyrimidine-5-carboxamide, (Compound A):

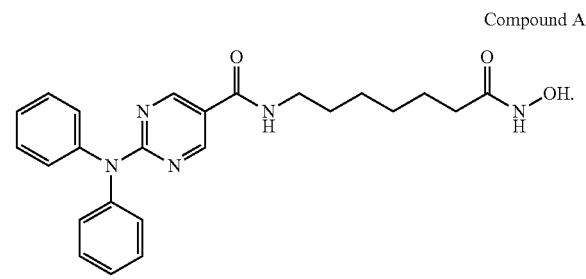 [SMILES: O=C(CCCCCCNC(=O)c1cnc(N(c2ccccc2)c2ccccc2)nc1)NO]

Compound A

3. The method of claim 1, wherein the abnormally high bone catabolism is associated with increased osteoclastogenesis in the subject, decreased osteoblastogenesis in the subject, increased osteoclast activity in the subject, decreased osteoblast activity in the subject, an imbalance of osteoclastogenesis and osteoblastogenesis in the subject, or an imbalance of osteoclast and osteoblast activity in the subject.

4. The method of claim 1, further comprising administering an additional active agent selected from the group consisting of bisphosphates, RANK ligands, bortezomib, Carfilzomib, lenalidomide, and Pomalidomide.

5. The method of claim 1, wherein the methods further include administering a bisphosphate.

6. The method of claim 1, wherein the reverse amide compound is 2-((2-chlorophenyl)(phenyl)amino)-N-(7-(hydroxyamino)-7-oxoheptyl)pyrimidine-5-carboxamide, (Compound C):

Compound C

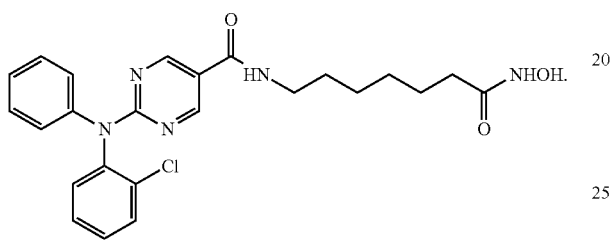

* * * * *

UNITED STATES PATENT AND TRADEMARK OFFICE
CERTIFICATE OF CORRECTION

| | | |
|---|---|---|
| PATENT NO. | : 9,512,083 B2 | Page 1 of 1 |
| APPLICATION NO. | : 14/233228 | |
| DATED | : December 6, 2016 | |
| INVENTOR(S) | : Raje et al. | |

It is certified that error appears in the above-identified patent and that said Letters Patent is hereby corrected as shown below:

On the Title Page

Insert item [60]:

--Related U.S. Application Data

Provisional application no. 61/509,857, filed on July 20, 2011.--

Signed and Sealed this
Twenty-eighth Day of February, 2017

Michelle K. Lee
*Director of the United States Patent and Trademark Office*